US011406721B2

(12) United States Patent
Tsien et al.

(10) Patent No.: US 11,406,721 B2
(45) Date of Patent: Aug. 9, 2022

(54) COMPOSITIONS AND METHODS FOR IMAGING CELL POPULATIONS

(71) Applicant: The Regents of the University of California, Oakland, CA (US)

(72) Inventors: Roger Y. Tsien, Eugene, OR (US); Eric T. Ahrens, Encinitas, CA (US); Alexander A. Kislukhin, Englewood, CO (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 719 days.

(21) Appl. No.: 15/999,690

(22) PCT Filed: Feb. 22, 2017

(86) PCT No.: PCT/US2017/018988
§ 371 (c)(1),
(2) Date: Aug. 20, 2018

(87) PCT Pub. No.: WO2017/147212
PCT Pub. Date: Aug. 31, 2017

(65) Prior Publication Data
US 2021/0205479 A1 Jul. 8, 2021

Related U.S. Application Data

(60) Provisional application No. 62/298,430, filed on Feb. 22, 2016.

(51) Int. Cl.
*A61K 49/10* (2006.01)
*A61K 49/18* (2006.01)
*B82Y 5/00* (2011.01)

(52) U.S. Cl.
CPC .......... *A61K 49/10* (2013.01); *A61K 49/1806* (2013.01); *B82Y 5/00* (2013.01)

(58) Field of Classification Search
CPC ... A61K 49/10; A61K 49/401806; B82Y 5/00
See application file for complete search history.

(56) References Cited

U.S. PATENT DOCUMENTS

| | | |
|---|---|---|
| 4,714,680 A | 12/1987 | Civin |
| 4,897,355 A | 1/1990 | Eppstein et al. |
| 4,993,415 A | 2/1991 | Long |
| 5,061,620 A | 10/1991 | Tsukamoto et al. |
| 5,279,833 A | 1/1994 | Rose |
| 5,283,185 A | 2/1994 | Epand et al. |
| 5,327,735 A | 7/1994 | Hatton |
| 5,334,761 A | 8/1994 | Gebeyehu et al. |
| 5,437,994 A | 8/1995 | Emerson et al. |
| 5,486,350 A | 1/1996 | Norfleet et al. |
| 5,527,928 A | 6/1996 | Nantz et al. |
| 5,552,155 A | 9/1996 | Bailey et al. |
| 5,578,475 A | 11/1996 | Jessee |
| 5,589,376 A | 12/1996 | Anderson et al. |
| 5,603,917 A | 2/1997 | Tweedle et al. |
| 5,643,741 A | 7/1997 | Tsukamoto et al. |
| 5,703,197 A | 12/1997 | Gordon et al. |
| 5,716,827 A | 2/1998 | Tsukamoto et al. |
| 5,750,397 A | 5/1998 | Tsukamoto et al. |
| 5,753,506 A | 5/1998 | Johe |
| 5,766,948 A | 6/1998 | Gage et al. |
| 5,824,489 A | 10/1998 | Anderson et al. |
| 5,851,832 A | 12/1998 | Weiss et al. |
| 5,914,108 A | 6/1999 | Tsukamoto et al. |
| 5,925,567 A | 7/1999 | Kraus et al. |
| 5,942,235 A | 8/1999 | Paoletti |
| 5,972,703 A | 10/1999 | Long et al. |
| 6,040,180 A | 3/2000 | Johe |
| 6,171,610 B1 | 1/2001 | Vacanti et al. |
| 6,190,910 B1 | 2/2001 | Kusakabe et al. |
| 6,361,996 B1 | 3/2002 | Rao et al. |
| 6,468,794 B1 | 10/2002 | Uchida et al. |
| 9,352,057 B2 | 5/2016 | Ahrens et al. |
| 2002/0016002 A1 | 2/2002 | Toma et al. |
| 2002/0123143 A1 | 9/2002 | Toma et al. |
| 2003/0003579 A1 | 1/2003 | Kadowaki et al. |
| 2007/0258886 A1 | 11/2007 | Ahrens et al. |
| 2011/0110863 A1* | 5/2011 | Ahrens .................. A61P 35/00 424/9.3 |

(Continued)

FOREIGN PATENT DOCUMENTS

| | | |
|---|---|---|
| EP | 0673655 A1 | 9/1995 |
| WO | WO 98/20907 | 5/1998 |

(Continued)

OTHER PUBLICATIONS

Ahrens, E.T. & Bulte, J.W.M., "Tracking immune cells in vivo using magnetic resonance imaging," Nat Rev Immunol, 13, 755-763 (2013).
Ahrens, E.T., Flores, R., Xu, H.Y. & Morel, P.A., "In vivo imaging platform for tracking immunotherapeutic cells," Nat Biotechnol, 23, 983-987, (2005).
Ahrens, E.T., Helfer, B.M., O'Hanlon, C.F., Schirda, C., "Clinical cell therapy imaging using a perfluorocarbon tracer and fluorine-19 MRI," Magn Reson Med, 72, 1696-1701 (2014).
Aime, S. et al., "Relaxometric evaluation of novel manganese(II) complexes for application as contrast agents in magnetic resonance imaging," J Bio Inorg Chem, 7, 58-67 (2002).
Awate, S P., et al., "Nonparametric Neighborhood Statistics for MRI Denoising," Information Processing in Medical Imaging Proceedings, 3565: 677-688 (2005).

(Continued)

*Primary Examiner* — Michael G. Hartley
*Assistant Examiner* — Jagadishwar R Samala
(74) *Attorney, Agent, or Firm* — Morgan, Lewis & Bockius, LLP; Christina A. MacDougall

(57) ABSTRACT

This disclosure provides compositions of metal-binding fluorinated compounds and associated methods for producing cellular labels for tracking cells by magnetic resonance imaging (MRI), computed tomography (CT), positron emission tomography (PET), and related methods.

11 Claims, 36 Drawing Sheets

(56) References Cited

U.S. PATENT DOCUMENTS

| | | | |
|---|---|---|---|
| 2013/0022990 A1 | 1/2013 | Ahrens | |
| 2013/0343999 A1 | 12/2013 | Ahrens et al. | |

FOREIGN PATENT DOCUMENTS

| | | | |
|---|---|---|---|
| WO | WO 00/02654 | | 1/2000 |
| WO | WO 00/53705 A1 | | 7/2003 |

OTHER PUBLICATIONS

Bansal et al., "Novel 89Zr cell labeling approach for PET-based cell trafficking studies," EJNMMI Research, 5:19, 1-11, Springer (2015).
Bao, P., et al., "Noise Reduction for Magnetic Resonance Images via Adaptive Multiscale Products Thresholding," IEEE Transactions on Medical Imaging, 22(9): 1089-1099 (Sep. 2003).
Barkley, L.B. & Levine, R., "The synthesis of Certain Ketones and α-Substituted β-Diketones Containing Perfluoroalkyl Groups," J Am Chem Soc, 75, 2059-2063 (1953).
Bertini, I., Galas, O., Luchinat, C., Messori, L. & Parigi, G., "A Theoretical Analysis of the 1H Nuclear Magnetic Relaxation Dispersion Profiles of Diferric Transferrin," J Phys Chem, 99, 14217-14222 (1995).
Betzer et al., "Nanoparticle-Based CT Imaging Technique for Longitudinal and Quantitative Stem Cell Tracking within the Brain: Application in Neuropsychiatric Disorders," ACS Nano, 8(9):9274-85 (2014).
Bharti, S. et al., "Improved quantification from $^1$H-NMR spectra using reduced repetition times," Metabolomics, 4, 367-376 (2008).
Binnemans, K., "Rare-Earth Beta-Diketonates," Handbook on the Physics and Chemistry of Rare Earths, vol. 35., (Eds. J.-C.G.B. Karl A. Gschneidner & K.P. Vitalij), 107-272 (Elsevier, 2005).
Bloembergen, N., "Proton Relaxation Times In Paramagnetic Solutions," J Chem Phys, 27(2), 572-573 (1957).
Bonitatibus et al., "Preclinical Assessment of a Zwitterionic Tantalum Oxide Nanoparticle X-ray Contrast Agent," ACS Nano, 6(8), 6650-6658 (2012).
Brown, R.W., Cheng, Y.C.N., Haacke, E.M., Thompson, M.R. & Venkatesan, R., "Magnetic Resonance Imaging: Physical Prinicples and Sequence Design," 2nd Edition. (John Wiley & Sons, Hoboken, NJ; 2014).
Comode et al., "Nanoparticle Contrast Agents for Computed Tomography: A Focus on Micelles," Contrast Media Mol Imaging, 9(1), 37-52 (Jan. 2014).
Cruz-Enriquez, H., et al., "Wavelet-Based Methods for Improving Signal-to-Noise Ratio in Phase Images," Image Analysis and Recognition, 3656: 247-254 (2005).
De Luca, E. et al., "Characterisation and evaluation of paramagnetic fluorine labelled glycol chitosan conjugates for $^{19}$F and $^1$H magnetic resonance imaging," J Biol Inorg Chem, 19, 215-227(2014).
De Vries, A. et al. Relaxometric studies of gadolinium-functionalized perfluorocarbon nanoparticles for MR imaging. Contrast Media Mol I 9, 83-91 (2014).
Derossi et al, "Cell Internalization of the Third Helix of the Antennapedia Homeodomain is Receptor-independent," J Biol Chem, 271(30),18188-18193 (1996).
Derossi et al, "The Third Helix of the Antennapedia Homeodomain Translocates through Biological Membranes," J Biol Chem, 269(14),10444-10450 (1994).
Feigner et al., "Lipofection: A highly efficient, lipid-mediated DNA-transfection procedure," Proc. Natl. Acad. Sci. USA, 84, 7413-7417 (Nov. 1987).
Ferrauto, G., Castelli, D.D., Terreno, E. & Aime, S., "In vivo MRI visualization of different cell populations labeled with PARACEST agents," Magn Reson Med, 69, 1703-1711 (2013).
Frankel and Pabo, "Cellular Uptake of the Tat Protein from Human Immunodeficiency Virus," Cell 55,1189-1193 (1988).

Freire, M.G., Ferreira, A.G.M., Fonseca, I.M.A., Marrucho, I.M. & Coutinho, J.A.P., "Viscosities of liquid fluorocompounds," J Chem Eng Data, 53, 538-542 (2008).
G. Friedrich, P. Soriano, "Promoter traps in embryonic stem cells: a genetic screen to identify and mutate developmental genes in mice," Genes Dev, 5, 1513-1523 (1991).
Funk, A.M., Fries, P.H., Harvey, P., Kenwright, A.M. & Parker, D., "Experimental measurement and theoretical assessment of fast lanthanide electronic relaxation in solution with four series of isostructural complexes," J Phys Chem A, 117, 905-917 (2013).
Ganesan. R.; et al., "Wavelet-based multiscale statistical process monitoring: A literature review," IIE Transactions, 36, 787-806 (Sep. 2004).
Gerhardt, G.E. & Lagow, R.J., "Synthesis of the perfluoropoly (ethylene glycol) ethers by direct fluorination," J Org Chem, 43(23), 4505-4509 (1978).
Ghugre, N R., "Superiority of 3D wavelet-packet denoising in MR microscopy," Magnetic Resonance Imaging, 21, 913-921 (Oct. 2003).
Gillis, P., Roch, A. & Brooks, R.A., "Corrected equations for susceptibility-induced $T_2$-shortening," J Magn Reason, 137, 402-407 (1999).
Graves et al., "Novel Preparation Methods of $^{52}$Mn for ImmunoPET Imaging," Bioconjug Chem., 26(10), 2118-2124 (Oct. 21, 2015).
Green and Loewenstein, "Mutational Analysis of HIV-1 Tat Minimal Domain Peptides: Identification of Trans-Dominant Mutants That Suppress HIV-LTR-Driven Gene Expression," Cell, 58, 215-223 (1989).
Gritti et al. 2002 J Neurosci 22 (2):437-45.
Gueron, M. Nuclear relaxation in macromolecules by paramagnetic ions: A novel mechanism. J Magn Reson (1969) 19, 58-66 (1975).
Haase, A., Frahm, J. & Matthaei, D. FLASH imaging: Rapid NMR imaging using low flip-angle pulses. J. Magn Reson. 67, 258 (1986).
Harvey, P., Kuprov, I. & Parker, D. Lanthanide complexes as paramagnetic probes for 19F magnetic resonance. Eur J Inorg Chem, 2015-2022 (2012).
Healy, D M., et al., Annals of Biomedical Engineering, 23 (5): 637-665 Sep.-Oct. 1995.
Hu, L., Zhang, L., Chen, J., Lanza, G.M. & Wickline, S.A. Diffusional mechanisms augment the fluorine MR relaxation in paramagnetic perfluorocarbon nanoparticles that provides a "relaxation switch" for detecting cellular endosomal activation. J Magn Reson Imaging 34, 653-661 (2011).
Janjic, J.M. & Ahrens, E.T. Fluorine-containing nanoemulsions for MRI cell tracking. Wiley Interdisciplinary Reviews. Nanomedicine and Nanobiotechnology 1, 492-501 (2009).
Janjic, J.M., Srinivas, M., Kadayakkara, D.K.K. & Ahrens, E.T. Self-delivering nanoemulsions for dual fluorine-19 MRI and fluorescence detection. J Am Chem Soc 130, 2832-2841 (2008).
Janjie et al., JACS, 2008, 130 (9), 2832-2841.
Kadayakkara, D.K., Damodaran, K., Hitchens, T.K., Bulte, J.W.M. & Ahrens, E.T. F-19 spin-lattice relaxation of perfluoropolyethers: Dependence on temperature and magnetic field strength (7.0-14.1 T). J Magn Reson 242, 18-22 (2014).
Khare, A., et al., International Journal of Wavelets Multiresolution and Information Processing, 3 (4): 477-406 Dec. 2005.
Kim et al., ACS Med Chem Lett, Apr. 7, 2015, 6(5):528-30; Greissinger et al., Proc Natl Acad Sci USA, Jan. 27, 2015, 112(4):1161-6.
Kimura et al., 1994, J. Biol. Chem. 269: 1896-67.
Kislukhin et al., Nat. Mater., Jun. 2016, 15(6): 662-668.
Kislukhin, A. A. et al. Paramagnetic fluorinated nanoemulsions for sensitive cellular fluorine-19 magnetic resonance imaging. Nat. Mater. (2016).
Kok, M.B. et al. Quantitative H-1 MRI, F-19 MRI, and F-19 MRS of cell-internalized perfluorocarbon paramagnetic nanoparticles. Contrast Media Mol Imaging 6, 19-27 (2011).
Krause et al., 2001, Cell 105: 360-77.
Kuppuswamy et al. (1989) Nucl. Acids Res. 17:3551-3561.
LaConte, S M., et al., Magnetic Resonance in Medicine, 44 (5): 746-757 Nov. 2000.
Lagasse et al., 2000 Nat Med 6: 1229-34.

(56) References Cited

OTHER PUBLICATIONS

Lai, C.-Z., Reardon, M.E., Boswell, P.G. & Bühlmann, P. Cation-coordinating properties of perfluoro-15-crown-5. J Fluor Chem 131, 42-46 (2010).
Laine, A F., Annual Review of Biomedical Engineering, 2: 511-550 2000.
Lintvedt, R.L. & Kernitsky, L.K. Ligand field information from charge-transfer spectra of substituted tris(1,3-diketonato)iron(III) chelates. Spectrochemical series for 1,3-diketones. Inorg Chem 9, 491-494 (1970).
Lo, J.C., Gui, J., Yabe, Y., Pan, C.-M. & Baran, P.S. Functionalized olefin cross-coupling to construct carbon-carbon bonds. Nature 516, 343-348 (2014).
Lusic and Grinstaff, Chem Rev, Mar. 13, 2013, 113(3):1641-66.
M. Qiu et al., Genes Dev 9, 2523 (1995).
Marchionni, G., Ajroldi, G., Righetti, M.C. & Pezzin, G. Molecular interactions in perfluorinated and hydrogenated compounds: Linear paraffins and ethers. Macromolecules 26, 1751-1757 (1993).
Meri et al., ACS Nano, Jun. 23, 2015, 9(6):6363-72.
Nash, K.L., Brigham, D., Shehee, T.C. & Martin, A. The kinetics of lanthanide complexation by EDTA and DTPA in lactate media. Dalton T 41, 14547-14556 (2012).
Neubauer, A.M. et al. Gadolinium-modulated F-19 signals from perfluorocarbon nanoparticles as a new strategy for molecular imaging. Magn Reson Med 60, 1066-1072 (2008).
Normandin et al., "Heat Induced Radiolabeled Nanoparticles Allow PET-derived Monocyte Tracking," Angew Chem Int Ed Engl., Oct. 26, 2015, pp. 1-12, 54(44): 13002-13006.
Nowak, R D., IEEE Transactions on Image Processing, 8 (10): 1408-1419 Oct. 1999.
Perez et al. (1992) J Cell Sci 102:717-722.
Pittenger et al., 1999 Science 284: 143-7.
Powell, D.H. et al. Magnetic-field-dependent electronic relaxation of Gd3+ in aqueous solutions of the complexes [Gd(H2O)8]3+, [Gd(propane-1,3-diamine-N,N,N',N'-tetraacetate)(H2O)2]-, and [Gd(N,N'-bis[(N-methylcarbamoyl)methyl]-3-azapentane-1,5-diamine-3,N,N'-triacetate)(H2O)] of interest in magnetic-resonance imaging. Helv Chim Acta 76, 2129-2146 (1993).
Qie et al., Nanoscale, Feb. 14, 2015, 7(6):2480-8.
Ruben et al., (1989) J. Virol 63:1-8.
Rubinstein, M., Baram, A. & Luz, Z. Electronic and nuclear relaxation in solutions of transition metal ions with spin S=3/2 and 5/2. Molecul Phys 20, 67-80 (1971).
Sanchez et al., Journal of Fluorine Chemistry, Aug. 1995, 73(2):259-264.
Sanders, J.K.M., Hanson, S.W. & Williams, D.H. Paramagnetic shift reagents. Nature of the interactions. J Am Chem Soc 94, 5325-5335 (1972).
Schmid, F., Höltke, C., Parker, D. & Faber, C. Boosting 19F MRI-SNR efficient detection of paramagnetic contrast agents using ultrafast sequences. Magn Reson Med 69, 1056-1062 (2013).
Schmidt, R. et al. Highly shifted proton MR imaging: Cell tracking by using direct detection of paramagnetic compounds. Radiology 272, 785-795 (2014).
Seheunders, P., IEEE Transactions on Image Processing, 13 (4): 475-485 Apr. 2004.
Shibata, S., Onuma, S. & Inoue, H. Crystal and molecular structure of trimeric bis(acetylacetonato)manganese(II). Inorg Chem 24, 1723-1725 (1985).
Solomon, I. Relaxation processes in a system of two spins. Phys Rev 99, 559-565 (1955).
Srinivas, M. et al. In vivo cytometry of antigen-specific T cells using 19F MRI. Magn Reson Med 62, 747-753 (2009).
Srinivas, M., Morel, P.A., Ernst, L.A., Laidlaw, D.H. & Ahrens, E.T. Fluorine-19 MRI for visualization and quantification of cell migration in a diabetes model. Magn Reson Med 58, 725-734 (2007).
Sur, S.K. & Bryant, R.G. Nuclear- and electron-spin relaxation rates in symmetrical iron, manganese, and gadolinium ions. J Phys Chem 99, 6301-6308 (1995).
Tavaré et al., Cancer Res, Jan. 1, 2016;76(1):73-82; Sato et al., Radiology. May 2015, 275(2):490-500.
Vigouroux, C., Bardet, M., Belorizky, E., Fries, P.H. & Guillermo, A. Nuclear and electronic relaxation in lanthanide solutions: (CH3)4N+/Gd3+ repulsive ion pair in D2O. Chem Phys Lett 286, 93-100 (1998).
Wu, Z Q., et al., Electronics Letters, 39 (7): 603-605 Apr. 3, 2003.
Yang et al., Radiology, May 2016, 279(2):513-22.
Yi et al., Nanoscale, Jan. 14, 2015;7(2):542-50.
Zhang, W. & Curran, D. P. Synthetic applications of fluorous solid-phase extraction (F-SPE). Tetrahedron 62, 11837-11865, doi:10.1016/j.tet.2006.08.051 (2006).
Zhao et al., 2002 Exp Neurol 174: 11-20.
Zuroubi, S., et al., Magnetic Resonance Imaging, 18 (1): 59-68 Jan. 2000.

* cited by examiner

| metal (M) | none | Fe | Gd |
|---|---|---|---|
| $R_1$ (s$^{-1}$) | 2.28±0.01 | 27.0±0.1 | 12.8±0.2 |
| $R_2$ (s$^{-1}$) | 4.01±0.03 | 85.6±0.2 | 285±3 |
| $R_2/R_1$ | 1.8 | 3.2 | 22 |

*Fig. 21*
Fluorine-19 MRI
- high sensitivity (83% rel. to $^1$H)
- quantitative, no background signal
- safe, biologically inert tracer molecules
- first clinical use: tracking therapeutic DCs in colorectal cancer patients
[Ahrens et al. Magn. Reson. Med. 2014, 72, 1696 PMID 25241945]
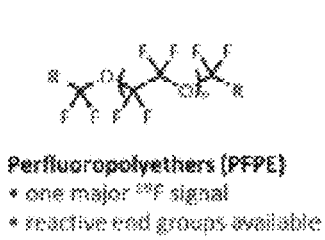
Perfluoropolyethers (PFPE)
- one major $^{19}$F signal
- reactive end groups available
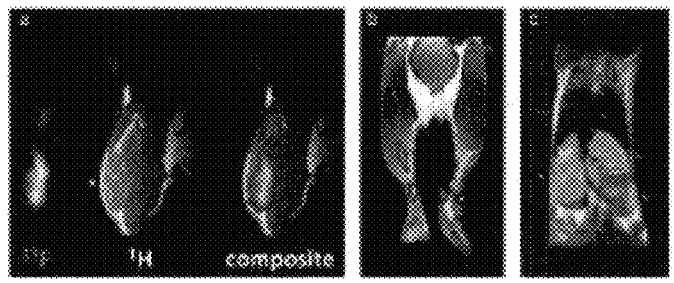

Choosing the metal $^{19}$F NMR lineshape of main PFPE peak (~91 ppm)
before and after metalation $Fe^{3+}$ is the best $R_1$ agent
$Gd^{3+}$ and $Mn^{2+}$ cause severe line broadening

Variable field and temperature relaxometry

Fig. 28
MRI
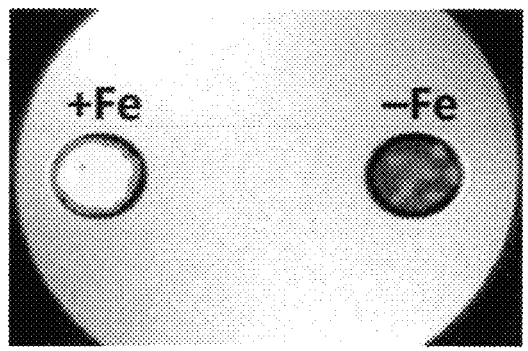 
$^1H/^{19}F$ (grayscale/pseudocolor) composite image of PFPE phantoms with and without Fe. $^{19}F$ SNR were 8.6 and 1.7, respectively.
Mouse glioma cells ($5 \times 10^6$) labeled with FETRIS ex vivo and injected into mouse flanks. After 24 hrs a cell 'hotspot' is seen on the right flank. Cells labeled with metal-free PFC and injected on the contralateral side could not be detected.

COMPOSITIONS AND METHODS FOR IMAGING CELL POPULATIONS

CROSS-REFERENCE TO RELATED APPLICATIONS

This application claims the benefit of U.S. Provisional Application No. 62/298,430, filed Feb. 22, 2016, the disclosure of which is hereby incorporated herein by reference in its entirety for all purposes.

STATEMENT AS TO RIGHTS TO INVENTIONS MADE UNDER FEDERALLY SPONSORED RESEARCH OR DEVELOPMENT

This invention was made with Government support under contracts EB017271, CA158448, and CA121938 awarded by the National Institutes of Health. The Government has certain rights in the invention.

BACKGROUND OF THE INVENTION

Clinical non-invasive imaging techniques are widely used as diagnostics and to track medical procedures. Magnetic resonance imaging (MRI) is a widely used clinical diagnostic tool because it is non-invasive, allows views into optically opaque subjects, and provides contrast among soft tissues at reasonably high spatial resolution. Conventional MRI mostly focuses on visualizing anatomy and lesions and has no specificity for any particular cell type. The 'probe' used by conventional MRI is the ubiquitous proton (H) in mobile water molecules. Cells are the fundamental building blocks of any organ system. An exogenous MRI probe or reagent to specifically tag cells is needed to facilitate cell-specific imaging in living subjects. For small animal studies, there are many options available for tracking cells in their native environment, especially using various fluorescent and bioluminescent probes and reporters. However, there remains a great unmet need for cell tracking technologies that have the potential for clinical translation. There are several non-invasive diagnostic imaging modalities that are routinely used in humans including various radioisotope methods, MRI, computed tomography, and ultrasound. Adopting existing diagnostic imaging modalities to visualize cells in the body is a complex problem. Non-invasive imaging of the dynamic trafficking patterns of populations of immune cells can play an important role in elucidating the basic pathogenesis of major diseases such as cancer and autoimmune disorders. Other cell populations, such as tumor or stem cells, can be tracked using MRI to provide insight into metastatic processes, cell engraftment and differentiation, and tissue renewal. Moreover, cells are increasingly being used as therapeutic agents to treat genetic and neurological disorders, as well as chronic conditions such as autoimmunity and cancer. A common need for virtually all cell therapies, particularly at the development stage, is a non-invasive way to detect and quantify the cell biodistribution (e.g, the distribution or location of the cell in the body) following injection. Non-invasive imaging of cell trafficking is capable of providing critical feedback regarding modes of action of the cells, optimal routes of delivery and therapeutic doses for individuals. On the regulatory side, emerging new therapies, such as those using immunotherapeutic and stem cells, are slow to gain regulatory approvals partly because clinical researchers are challenged to verify where the cells go immediately after inoculation and where they migrate to days and weeks later. Cell tracking can potentially provide this information and may help in lowering regulatory approval barriers.

Intimately related to cell trafficking is inflammation and the inflammatory response. Prevalent inflammatory diseases include, for example, arthritis, asthma, atherosclerosis, cancer, diabetes, chronic obstructive pulmonary disease (COPD), inflammatory bowel disease (IBD), infection, multiple sclerosis, and organ transplant rejection. The progression of these diseases can often be slow, and the effectiveness of treatment can be observed only after days, weeks or months. Thus, there is a strong unmet need for inflammation-specific diagnostics, as well as inflammation surrogate biomarkers that permit therapeutic developers to determine efficacy quickly, quantitatively, and in a longitudinal fashion. A related need entails pharmacological safety profiling to detect 'off target' inflammatory side effects in pre/clinical drug trials. A non-invasive, image-based biomarker could potentially fill these unmet needs. Vital imaging can accelerate the 'go/no go' decision making process at the preclinical and clinical trial stages, and can facilitate smaller, less costly trials by enrolling fewer patients. Imaging can potentially yield quantitative data about inflammation severity and time course in the anatomical context. The highest value imaging biomarker would have broad utility for multiple diseases and be applicable from mouse-to-man, thereby minimizing validation studies.

Fluorine-19 ($^{19}$F) 'tracer' agents are an emerging approach to intracellularly label cells of interest, either ex vivo or in situ, to enable cell detection via $^{19}$F MRI {Ahrens, 2013; Ahrens, 2013}. The $^{19}$F label yields positive-signal 'hot-spot' images, with no background signal due to negligible fluorine concentration in tissues. Images can be quantified to measure fluorine content in regions of interest yielding a measure of cell numbers at sites of accumulation. Tracer agent compositions have mostly focused on nontoxic perfluorocarbons (PFC). Fluorine-19 is an alternate nucleus that can be imaged using many of today's MRI installations, and this ability is well known in the art.

Often a key limitation of $^{19}$F MRI using various types of probes is sensitivity. Improving the sensitivity of $^{19}$F cell detection could lower the barriers for using these technologies in a much wider range of biomedical applications. Unlike conventional $^1$H MRI, where the probe (water) concentration (>100 Molar $^1$H) and thus sensitivity is high, $^{19}$F MRI is limited by the total amount and distribution of fluorine atoms introduced into the subject's tissue. In cell tracking and inflammation imaging applications, most often the amount of $^{19}$F in a region of interest is limited by the amount of tracer agent that can be safely internalized into cells of interest. Thus, to improve sensitivity and overall detectability of sparse cell numbers in tissue, one must somehow improve the intrinsic MRI sensitivity of the PFC molecule (or other type of $^{19}$F probe molecule).

A key approach for boosting intrinsic sensitivity of PFC is by decreasing the intrinsically-high $^{19}$F spin-lattice relaxation time ($T_1$) of PFC molecules. The $T_1$ parameterizes the characteristic time constant for the time that it takes for $^{19}$F nuclei to align along the field direction of the MRI magnet, i.e., the equilibrium alignment direction or longitudinal direction, or alternatively $T_1$ is the time constant for the nuclei to align along the field direction after it has been knocked out of equilibrium. The $T_1$ value ultimately limits the rate of $^{19}$F MRI data acquisitions. Generally, $^{19}$F images require summation of multiple acquisitions (i.e., signal averaging) to generate a sufficient signal-to-noise ratio (SNR) for confident interpretation. High $^{19}$F $T_1$ values require a long repetition time (TR) to allow for longitudinal signal recovery, thus limiting the number of signal acquisitions attainable during a fixed total imaging time ($t_i$). As $t_i$ is constrained when scanning patients, the key parameter to maximize is $SNR/t_i$. Shortening $T_1$ can increase $SNR/t_i$, sensitivity, and decrease the minimum number of detectable cells per voxel. Overall, the creation of stable and cytocompatible $^{19}F$ agents with 'ultra-fast' $T_1$, as well as a high $^{19}F$ density on the molecule, has been an open challenge that can greatly impact the MRI field, enabling accelerated MRI acquisitions and the detection of sparser cell populations in vivo.

The relaxation times $T_1$ and $T_2$ can be profoundly altered by high-spin paramagnetic metal ions (e.g., $Mn^{2+}$, $Fe^{3+}$, $Gd^{3+}$). Prior studies have attached $Gd^{3+}$ to the outer surface of the PFC nanoemulsion droplet resulting in modest reductions in $T_1$. With increasing distance (r), the steep fall-off ($\sim r^{-6}$) of paramagnetic relaxation rate enhancement from paramagnetic centers limit the efficacy of relaxation agents bound to the surface of PFC nanoparticles.[8, 10] Thus, effective relaxation enhancement necessitates introduction of metal ions into the fluorous phase, i.e., within the nanoemulsion droplets, to achieve a short $T_1$ using a minimum amount of a paramagnetic additive. This presents a significant challenge due to very disparate properties of fluorocarbons (extremely hydrophobic) and common MRI contrast agents (hydrophilic, multidentate chelates). A key innovation of the present disclosure was achieved by devising a material that permits combining metal ions with bulk fluorocarbons, while retaining the high fluorination and sensitivity as well as biological inertness typical of fluorocarbons.

It should be noted that fluorinated lanthanide chelates have been proposed for MRI cell tracking applications, but these have not been shown to be particularly useful for this purpose. Most importantly, these molecules would not provide any improvement in sensitivity for cell tracking applications over previous perfluorocarbon emulsions that have been used in the past, and in fact they would have inferior sensitivity in these applications. This is due to the fact that it is infeasible to get sufficiently high levels of fluorinated lanthanide complexes into cells, where even under the best loading conditions, the cellular loading level is at least 10 times smaller than what is widely reported with PFC nanoemulsions, which achieve up to $10^{12}$ $^{19}F/cell$ for "normal" cell and $10^{13}$ $^{19}F/cell$ for larger cells (e.g., antigen presenting cells). Importantly, minimum cell detectability scales linearly with intracellular loading. Thus, far greater intracellular loadings of $^{19}F$ can be achieved by labeling with emulsified liquid fluorocarbons than with osmotically active hydrophilic chelates with relatively low fluorine content. See, U.S. Pat. No. 9,352,057 is incorporated by reference herein in its entirety The present invention meets this need.

BRIEF SUMMARY OF THE INVENTION

The present invention provides non-invasive imaging methods, comprising (a) administering to a subject a cellular labelling composition comprising a compound comprising fluorine-19 ($^{19}F$), wherein said compound comprising fluorine-19 ($^{19}F$) associates with one or more cells; and (b) detecting said association using an imaging modality, wherein said association can include cellular binding and/or cellular uptake. In some embodiments, the method is used for cytotherapy, e.g., cell-based therapy.

In some embodiments, the imaging modality is selected from the group consisting of magnetic resonance imaging (MRI), positron emission tomography (PET), single-photon emission coherent tomography (SPECT), ultrasonograpy (US), and computed tomography (CT).

In some embodiments, the compound comprising fluorine-19 ($^{19}F$) comprises a perfluorinated compound. In certain embodiments, the compound comprising fluorine-19 ($^{19}F$) comprises a metalated perfluorinated compound.

In some embodiments, the perfluorinated compound binds and tightly retains metal ions in the fluorous phase. The metal ions can be selected from the group consisting of $VO^{2+}$, $Cr^{3+}$, $Mn^{2+}$, $Mn^{3+}$, $Fe^{3+}$, $Ni^{2+}$, $Cu^{2+}$, $Ce^{3+}$, $Pr^{3+}$, $Nd^{3+}$, $Sm^{3+}$, $Eu^{3+}$, $Gd^{3+}$, $Tb^{3+}$, $Dy^{3+}$, $Ho^{3+}$, $Er^{3+}$, $Tm^{3+}$, $Yb^{3+}$, $^{44}Sc^{3+}$, $^{52}Mn^{2+}$, $^{61}Cu^{2+}$, $^{64}Cu^{2+}$, $^{66}Ga^{3+}$, $^{68}Ga^{3+}$, $^{86}Y^{3+}$, $^{89}Zr^{4+}$, $^{67}Ga^{3+}$, $^{99m}Tc^{4+}$, $^{111}In^{3+}$ and $^{177}L^{3+}$.

In some embodiments, the perfluorinated compound is formulated as a nanoemulsion. The nanoemulsion can further comprise a perfluorocarbon.

In some embodiments, the perfluorocarbon is a compound of any one of formulas (ii)-(vi):

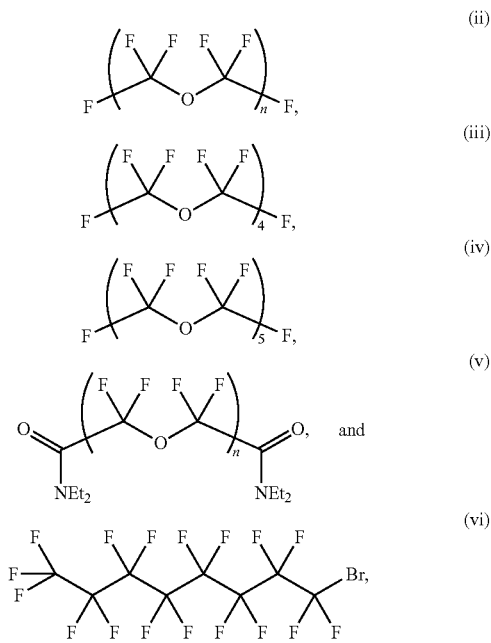

wherein n is 4 to 20, or 4 to 16.

In some embodiments, the perfluorinated compound is formula (i):

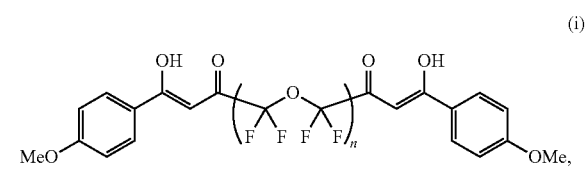

wherein n is 4 to 20, or 4 to 16.

In some embodiments, said composition comprises
(a) said perfluorinated compound is formula (i):

(i)

[Chemical structure: MeO-C6H4-CH=C(OH)-C(=O)-CF2-(CF2)n-O-(CF2)n-CF2-C(=O)-C(OH)=CH-C6H4-OMe]

and (b) a perfluorocarbon of any one of formulas (ii)-(vi):

(ii)

[Chemical structure with F substituents and O, subscript n]

(iii)

[Chemical structure with F substituents and O, subscript 4]

(iv)

[Chemical structure with F substituents and O, subscript 5]

(v)

[Chemical structure with NEt2 groups, F substituents, O, subscript n]

(vi)

[Chemical structure with F substituents and Br terminus]

wherein n is 4 to 20, or 4 to 16.

In some embodiments, the composition comprises:
(a) said perfluorinated compound is formula (i):

(i)

[Chemical structure: MeO-C6H4-CH=C(OH)-C(=O)-CF2-(CF2)n-O-(CF2)n-CF2-C(=O)-C(OH)=CH-C6H4-OMe]

and (b) a perfluorocarbon of any one of formulas (ii)-(vi):

(ii)

[Chemical structure with F substituents and O, subscript n]

wherein n is 4 to 20, or 4 to 16.

In some embodiments, composition allows tracking cells by MRI, wherein the method comprises detecting the cells bound to at least one component of the composition comprising fluorine-19 ($^{19}$F).

In some embodiments, the one or more cells are immune cells that accumulate at tissue sites as part of an inflammatory response. In certain embodiments, the method is a diagnostic detection method.

In some embodiments, the one or more cells are cells that are grafted into the body in order to treat a disease or condition.

In some embodiments, the method is cytotherapy.

In some embodiments, the one or more cells comprise endogenous cells in the body of the subject.

In some embodiments, the one or more cells are selected from the group consisting of T cells, B cells, macrophages, NK cells, dendritic cells (DCs), stem cells, progenitor cells, and cancer cells.

In some embodiments, the one or more cells comprise engineered cells.

In some embodiments, the compound comprising fluorine-19 ($^{19}$F) is a dual-mode agent and is capable of being detected by more than one imaging modality.

In some embodiments, the compound comprising fluorine-19 ($^{19}$F) is a dual-mode agent and is capable of being detected by two or more imaging modalities. In some embodiments, the compound is used for MRI and PET, MRI and SPECT, MRI and US, and MRI and CT. In some embodiments, MRI or MRS (magnetic resonance spectroscopy) is used. Optionally, one or more additional imaging modalities are used.

The present invention provides in vivo imaging method, comprising (a) ex vivo labeling cells with a cellular labelling composition comprising a compound comprising fluorine-19 ($^{19}$F) under such conditions that said compound comprising fluorine-19 ($^{19}$F) is internalized by the cells; (b) administering the labeled cells to a subject; (c) detecting said labeled cells in said subject using an imaging modality, and (d) assaying for the degree of labeled cell accumulation in one or more tissues in said subject. The labeled cells can be administered (e.g., introduced, grafted, transplanted, injected, and the like) into the subject. In some instances, the method can be used for inflammation imaging, e.g., non-invasive, in vivo imaging of inflammatory cells or sites of inflammation in the subject.

In some embodiments, the method includes detecting the labeled cells in an excised tissue obtained from the subject after administering the labeled cells to the subject, and assaying for the degree of labeled cell accumulation in the excised tissue from the subject. In other words, the method can include measuring or quantitating the labeled cells that are located in the excised tissue. Detailed descriptions for quantitating the cell labeling (e.g., the labeled cells) are provided herein.

In some embodiments, assaying comprises quantitating the average total intracellular probe mass at sites of accumulation of said labeled cells.

In some embodiments, the cells are autologous cells. In certain embodiments, the cells are allogeneic cells.

In some embodiments, the imaging modality is selected from the group consisting of magnetic resonance imaging (MRI), positron emission tomography (PET), single-photon emission coherent tomography (SPECT), ultrasonography (US), and computed tomography (CT). In certain embodiments, the imaging modality is magnetic resonance imaging (MRI). In certain embodiments, the imaging modality is magnetic resonance spectroscopy (MRS).

In some embodiments, the cells are selected from the group consisting of T cells, B cells, macrophages, natural killer (NK) cells, dendritic cells (DCs), stem cells, progenitor cells, and cancer cells. The cells can be engineered cells.

In some embodiments, the compound comprising fluorine-19 ($^{19}F$) comprises a perfluorinated compound. The perfluorinated compound can comprise a metal-binding β-diketone conjugated to a linear perfluorocarbon. In some cases, the perfluorinated compound binds and tightly retains metal ions in the fluorous phase. In the other words, the perfluorinated compound can be metalated, for example, metalated by a transition metal or lanthanide. In some embodiments, the metal ions are selected from the group consisting of $VO^{2+}$, $Cr^{3+}$, $Mn^{2+}$, $Mn^{3+}$, $Fe^{3+}$, $Ni^{2+}$, $Cu^{2+}$, $Ce^{3+}$, $Pr^{3+}$, $Nd^{3+}$, $Sm^{3+}$, $Eu^{3+}$, $Gd^{3+}$, $Tb^{3+}$, $Dy^{3+}$, $Ho^{3+}$, $Er^{3+}$, $Tm^{3+}$, $Yb^{3+}$, $^{44}Sc^{3+}$, $^{52}Mn^{2+}$, $^{61}Cu^{2+}$, $^{64}Cu^{2+}$, $^{66}Ga^{3+}$, $^{68}Ga^{3+}$, $^{86}Y^{3+}$, $^{89}Zr^{4+}$, $^{67}Ga^{3+}$, $^{99m}Tc^{4+}$, $^{111}In^{3+}$ and $^{177}L^{3+}$.

In some embodiments, the perfluorinated compound is formulated as a nanoemulsion. In some instances, the nanoemulsion further comprises a perfluorocarbon.

In some embodiments, the perfluorocarbon is a compound of any one of formulas (ii)-(vi):

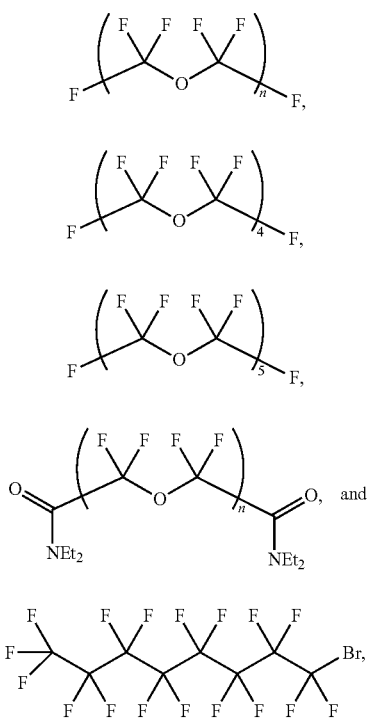

wherein n is 4 to 20, or 4 to 16.

In some embodiments, the perfluorinated compound is formula (i):

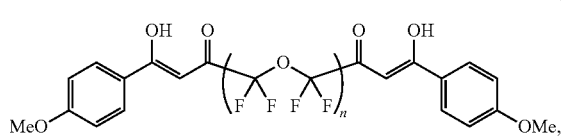

wherein n is 4 to 20, or 4 to 16.

In certain embodiments, said nanoemulsion comprises:
(a) said perfluorinated compound is formula (i):

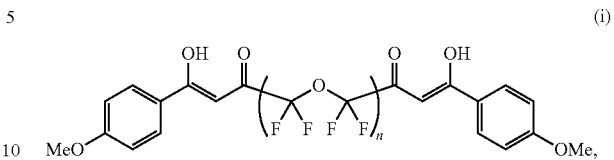

and
(b) a perfluorocarbon of formulas (ii):

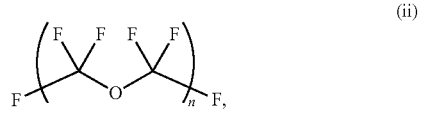

wherein n is 4 to 20, or 4 to 16.

The present invention provides compound of formula (i):

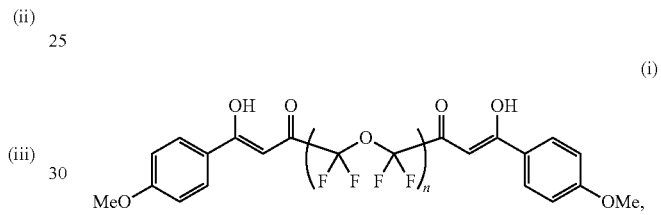

wherein n is 4 to 20, or 4 to 16.

Also, provided herein is a nanoemulsion formulation comprising a compound of formula (i):

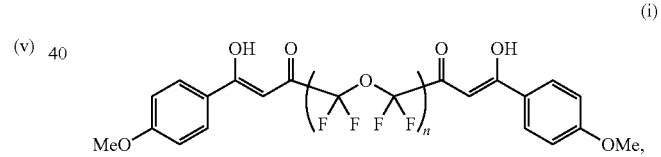

wherein n is 4 to 20, or 4 to 16 in an oil-in-water colloidal suspension or emulsion.

In some embodiments, the nanoemulsion formulation further comprises a compound of any one of formulas (ii)-(vi):

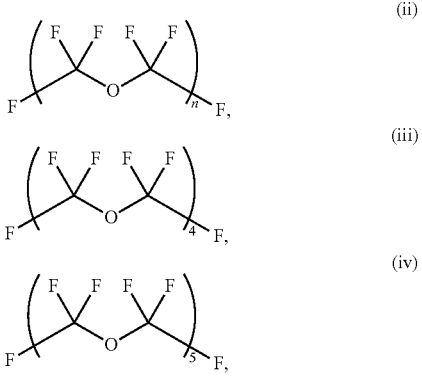

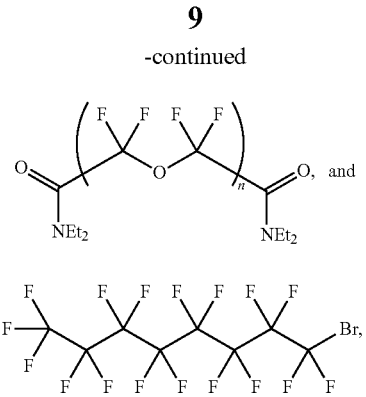

wherein n is 4 to 20, or 4 to 16.

In some embodiments, the compound of the nanoemulsion formulation is metalated and the nanoemulsion further comprises metal ions. The metal ions can be selected from the group consisting of $VO^{2+}$, $Cr^{3+}$, $Mn^{2+}$, $Mn^{3+}$, $Fe^{3+}$, $Ni^{2+}$, $Cu^{2+}$, $Ce^{3+}$, $Pr^{3+}$, $Nd^{3+}$, $Sm^{3+}$, $Eu^{3+}$, $Gd^{3+}$, $Tb^{3+}$, $Dy^{3+}$, $Ho^{3+}$, $Er^{3+}$, $Tm^{3+}$, $Yb^{3+}$, $^{44}Sc^{3+}$, $^{52}Mn^{2+}$, $^{61}Cu^{2+}$, $^{64}Cu^{2+}$, $^{66}Ga^{3+}$, $^{68}Ga^{3+}$, $^{86}Y^{3+}$, $^{89}Zr^{4+}$, $^{67}Ga^{3+}$, $^{99m}Tc^{4+}$, $^{111}In^{3+}$ and $^{177}L^{3+}$.

The present invention also provides for pharmaceutical and/or diagnostic compositions comprising a nanoemulsion formulation comprising a compound comprising fluorine-19 ($^{19}F$), wherein the compound comprising fluorine-19 ($^{19}F$) associates with one or more cells and said association is capable of being detected using an imaging modality.

In some embodiments, the compound comprising fluorine-19 ($^{19}F$) is a metalated perfluorinated compound. The metalated perfluorinated compound can comprise a metal-binding β-diketone conjugated to a linear perfluorocarbon. In certain embodiments, the metalated perfluorinated compound binds and tightly retains metal ions in the fluorous phase.

In some embodiments, the composition further comprises a perfluorocarbon. In some instances, the perfluorocarbon is a compound of any one of formulas (ii)-(vi):

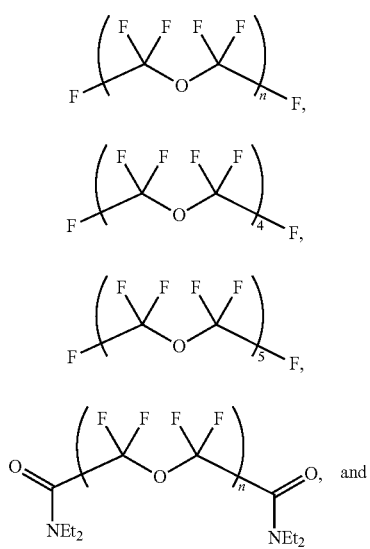

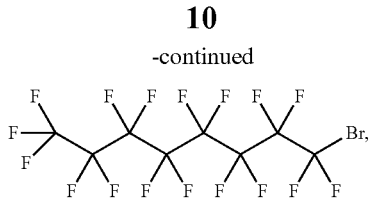

wherein n is 4 to 20, or 4 to 16.

In some embodiments, pharmaceutical and/or diagnostic composition comprises: (a) said perfluorinated compound is formula (i):

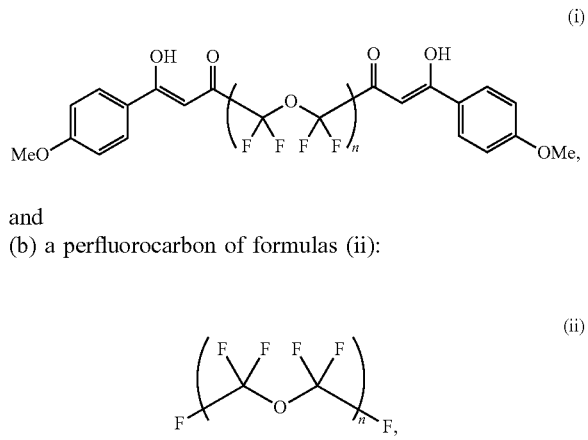

and
(b) a perfluorocarbon of formulas (ii):

(ii)

wherein n is 4 to 20, or 4 to 16

In some embodiments, the pharmaceutical and/or diagnostic composition is metalated and the nanoemulsion further comprises metal ions. The metal ions can be selected from the group consisting of $VO^{2+}$, $Cr^{3+}$, $Mn^{2+}$, $Mn^{3+}$, $Fe^{3+}$, $Ni^{2+}$, $Cu^{2+}$, $Ce^{3+}$, $Pr^{3+}$, $Nd^{3+}$, $Sm^{3+}$, $Eu^{3+}$, $Gd^{3+}$, $Tb^{3+}$, $Dy^{3+}$, $Ho^{3+}$, $Er^{3+}$, $Tm^{3+}$, $Yb^{3+}$, $^{44}Sc^{3+}$, $^{52}Mn^{2+}$, $^{61}Cu^{2+}$, $^{64}Cu^{2+}$, $^{66}Ga^{3+}$, $^{68}Ga^{3+}$, $^{86}Y^{3+}$, $^{89}Zr^{4+}$, $^{67}Ga^{3+}$, $^{99m}Tc^{4+}$, $^{111}In^{3+}$ and $^{177}L^{3+}$.

In some embodiments, the nanoemulsion is selected from the group consisting of an oil-in-water colloidal suspension and emulsion, comprising an encapsulated fluorinated liquid comprising said compound comprising fluorine-19 ($^{19}F$).

In some embodiments, the perfluorinated compound comprising fluorine-19 ($^{19}F$) can be an imaging probe compatible with in vivo applications. Such applications can include, but are not limited to, detecting and/or assaying cells associated with the compound in a subject. In certain embodiments, the perfluorinated compound comprising fluorine-19 ($^{19}F$) can be an imaging probe compatible with in vitro or ex vivo applications. The perfluorinated compound comprising fluorine-19 ($^{19}F$) can further comprise a targeting moiety. The targeting moiety is selected from the group consisting of antibodies and fragments thereof, peptides, arginine-rich domains, cationic lipids, and aptamers.

In some embodiments, the composition comprises at least two compounds comprising fluorine-19 ($^{19}F$), wherein the at least two compounds provide at least two distinct signatures when detected using an imaging modality capable of individual detection. The imaging modality is selected from the group consisting of magnetic resonance imaging (MRI), positron emission tomography (PET), single-photon emission coherent tomography (SPECT), ultrasonography (US), and computed tomography (CT).

In some embodiments, the distinct signatures correspond to multiple cell types, the same cell type at different time points, or multiple molecular epitopes within a single subject.

In some embodiments, the compound comprising fluorine-19 ($^{19}F$) is a theranostic agent.

In some embodiments, the theranostic agent functions as both a therapeutic agent and an imaging probe.

In some embodiments, the theranostic agent allows for visualizing the accurate delivery and dose of the therapy within the subject.

In some embodiments, the pharmaceutical composition is an oil-in-water colloidal suspension or emulsion comprising an encapsulated fluorinated liquid.

BRIEF DESCRIPTION OF THE DRAWINGS

FIG. 2A, Synthesis of metal-binding fluorinated diketones (FDK) from PFPE-OMe (denoted as $R_FCO_2Me$). FIG. 2B, Structures of fluorocarbons used for $^{19}F$ MRI. FIG. 2C, Composition and preparation of various metal-binding (A, B, D, F, G) and control (C, E) fluorocarbon nanoemulsions. FIG. 2D, $^{19}F$ NMR spectra (11.7 T) of emulsions A-C (4.5 g/L $^{19}F$, 90% $D_2O$). Signals from terminal $CF_2$ of diketone ligands are well separated from other peaks and are used to determine ligand concentration. The peak at −76 ppm is the reference ($CF_3CO_2Na$, TFA). FIG. 2E, Addition of aqueous metal chlorides to FDK emulsions yields metalated emulsions; Ar=pAn. FIG. 2F, Absorption spectra of metal-binding emulsion B (70 µM diketone, 0.09 g/L $^{19}F$) (color) and control emulsion C (0.09 g/L) (---) in the presence of $Fe^{3+}$. Increasing [$Fe^{3+}$] causes the appearance of ferric tris-diketonate charge transfer bands at 395 and 500 nm that grow linearly in intensity until the ca. 3:1 ligand:Fe ratio is reached at 25 µM $Fe^{3+}$.

FIG. 3A, $R_1$ and $^{19}F$ NMR spectra of iron(III) tris-β-diketonate nanoemulsion (4.5 g/L $^{19}F$, 3.5 mM diketone) in the presence of 0.5 mM metal ions, 15 mM HEPES, and at pH 7.4. The peaks from different $^{19}F$ spectra are scaled to the same absolute intensity. The term "FETRIS" (FEric TRIS-diketonate) refers to pAn-FDK blended with PFPE and metalated with $Fe^{3+}$. FIG. 3B, Relaxometric analysis of $Fe^{3+}$ and $Gd^{3+}$ binding capacity. Shown are measurements of $R_1$ for both PFPE (fluorous phase) and trifluoroacetate reference (TFA) added to the aqueous phase. FIG. 3C, Magnetic field dependence at T=295 K and FIG. 3D, temperature ($B_0$=9.4 T) dependence of observed relaxation rates $R_1$ (•) and $R_2$ (x) in FETRIS nanoemulsion (22.5 g/L $^{19}F$, 17.5 mM diketone, 2.8 mM $Fe^{3+}$) and predicted $R_1$ (-) values using Eqs. S1-S4. Predicted $R_1$ values represent best fit to SBM equations, with r=1.19 nm, $\tau_F$ (295 K)=0.80 ns, $\tau_v$ (295 K)=3.59 ps, the Arrhenius temperature dependence with activation energies of 3.6 kcal/mol for $\tau_F$ and 4.5 kcal/mol for $\tau_v$. The diamagnetic contributions to $R_1$ are presumed to be negligible and Δ fixed at 0.2 $cm^{-1}$. $R_1$ values increase, while $R_2$ values decrease, at lower magnetic field strengths, suggesting that there will be no degradation of SNR at clinical fields due to line broadening.

FIG. 5A, Cell viability. FIG. 5B, Cell uptake of FETRIS as measured by $^{19}F$ NMR. FIG. 5C, Correlation of uptake determined by $^{19}F$ NMR with optical absorbance of cell lysate at 390 nm due to FETRIS. Error bars are standard deviations from three independent replicates.

FIG. 6A, Phantom comprised of two agarose-embedded NMR tubes containing FETRIS nanoemulsion (4.5 g/L $^{19}F$) with 0.5 mM $Fe^{3+}$ ($R_1/R_2$=32.5/170 $s^{-1}$) and nanoemulsion without metal ($R_1/R_2$ 2.2/3.7 $s^{-1}$), denoted +Fe and −Fe, respectively. The top panel shows unthresholded $^{19}F$ images, and below, the $^{19}F$ image is thresholded, rendered in hot-iron pseudo-color (scale bar), and overlaid onto the grayscale $^1H$ image. The $^{19}F/^1H$ MRI data were acquired using a GRE sequence. FIG. 6B, Displays mouse GL261 glioma cells (5×10⁶) labeled with FETRIS nanoemulsion ex vivo and injected subcutaneously into mouse flank. The $^{19}F$ data is rendered in pseudo-color and placed on a grayscale slice from the $^1H$ data. After 24 hours, mice were imaged, and a cell 'hot-spot' is seen on the right flank in the axial view. Cells labeled with metal-free nanoemulsion and injected on the contralateral side could not be detected. Asterisk is adjacent chemical shift displacement artifact from hyperintense subcutaneous fat at 11.7 T. The $^{19}F$ and $^1H$ images were acquired using ZTE and GRE pulse sequences, respectively. For display, a co-registered 2D GRE slice was embedded into a 3D rendering of the $^{19}F$ data FIG. 7. Cellular imaging using fluorinated and metalated nanoemulsions.

FIG. 19A displays cell yields (using CellTiter-Glo assay, Promega, Madison, Wis.) after labeling with emulsion B with and without Fe$^{3+}$ (2:1 diketone:Fe molar ratio). FIG. 19B displays uptake of PFPE from emulsion B under the same conditions. FIG. 19C shows $R_1$ (at 11.7 T) of emulsions B and C before (measured in DMEM+10% FBS) and after 24 hours (measured in cell lysates) labeling with 4 g/L PFPE from emulsion B or C. FIG. 19D is R (11.7 T) of emulsion B (4.5 g/L, 3.5 mM diketone) with 0.5 mM GdCl$_3$, measured before (15 mM HEPES, pH 7.4) and 24 hours after labeling. FIG. 19E displays fluorescence microscopy images of cells labeled with nanoemulsion containing europium. The 9L cells were labeled in 6-well dishes with emulsion B (left) or emulsion C (right) in 2% FBS/DMEM (1 mL) for 2 hours, excess labeling reagent was washed off, and the cells were allowed to recover in complete media (10% FBS/DMEM) overnight. Cells were imaged on Zeiss Axiovert 200M with 20× air objective. These composite images are comprised of differential interference contrast (DIC) and fluorescent (375/36 nm excitation and 595/50 nm emission filters) images. Intracellular europium fluorescence was observed with metal-binding emulsion B but not with the control emulsion C. The scale bar is 20 μm. detectability scales linearly with sensitivity gains.

FIG. 21. Fluorine-19 MRI.

FIG. 28. MRI FETRIS images.

FIG. 36A shows pAn-FDK sample after MeOH washing, but prior to fluorous SPE purification. FIG. 36B displays the same sample after fluorous SPE. Overall, GC-MS data shows that fluorous SPE is an effective method for purifying pAn-FDK by removing p-acetanisole (pAcAn).

DETAILED DESCRIPTION OF THE INVENTION

Summary

Figure 1:
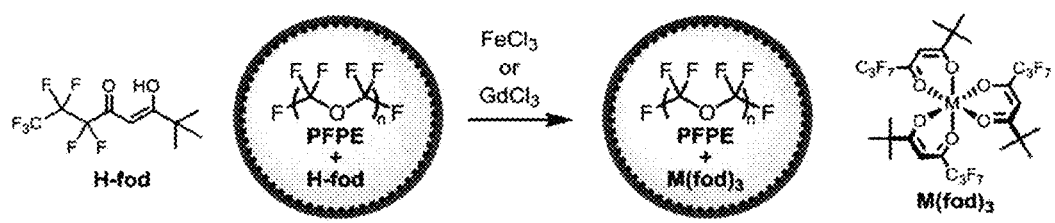
FIG. 1. Comparison of iron and gadolinium diketonates (H-fod) as $^{19}F$ relaxation agents for PFPE. The relaxometry results (9.4 T) are displayed for PFPE emulsions (120 g/L PFPE) containing H-fod (2.8 mM) 24 hours after the addition of 0.7 mM metal ions. $R_1$ and $R_2$ values are reported for the main PFPE peak at −91.4 ppm. The results show that $Fe^{3+}$ is a more effective $R_1$ agent than $Gd^{3+}$.

The invention provides clinical non-invasive imaging methods, particularly magnetic resonance imaging (MRI), to visualize cells and cells targets in the body. For instance, cells (e.g., target cells) labelled with the fluorine-19 containing compositions provided herein can be visualized (imaged, tracked, tracked, and the like) in a subject, e.g., a human subject, and quantitated. The invention also describes novel compositions of perfluorinated compounds that can bind and tightly retain metal ions in the fluorous phase to enable sensitive detection using MRI and other imaging modalities. Provided herein are new nanoemulsion materials containing metal-binding β-diketones conjugated to linear perfluoropolyether (PFPE). The compositions described herein are useful for MRI as they can provide a single sharp resonance, provide desirable signal intensity and signal-to-noise ratio (SNR) efficient, eliminate any chemical shift artifact, maximize the SNR, are thermodynamically stable, and allow clear identification of the perfluorinated compound.

A key use of this technology is the production of sensitive cellular labels for tracking cells by fluorine-19 ($^{19}$F) MRI. Some applications include the diagnostic detection of immune cells that accumulate at tissue sites as part of an inflammatory response and cells that are grafted into the body in order to treat a disease or condition, i.e., cytotherapy. Cells can be endogenous cells in the body, for example, various immune cells (T cells, B cells, macrophages, NK cells, DCs, etc.), various stem cells and progenitor cells, cancer cells, as well as engineered cells, which are often used in cytotherapy in its various forms. Non-invasive imaging of immune cells in the body is useful because it can aid in the diagnosis and monitoring of inflammation. In the field of cytotherapy, the ability to image the cell graft provides valuable feedback about the persistence of the graft, potential cell migration, and improves safety surveillance. Many experimental cell therapies that are in clinical trials, e.g., stem cells and immunotherapeutic cells, could benefit from the use of this technology.

Other embodiments of the invention are metalated perfluorinated probes that can be detected by positron emission tomography (PET), single-photon emission coherent tomography (SPECT), ultrasonography (US), or computed tomography (CT), all of which are commonly used medical imaging modalities. The invention provides novel uses for these imaging modalities by providing a means to detect inflammatory cells and track cytotherapies non-invasively. Also, so called "dual-mode" agents are envisioned, which can be detected by more than one imaging modality (e.g., MRI-PET), thereby maximizing the utility of new generations of clinical imaging apparatus that integrate two (or more) detection modalities.

The invention describes multiple nanoemulsion formulations of metalated perfluorinated compounds (i.e., "imaging probes") to render the molecules compatible for in vivo applications, and to tailor the biodistribution of the labeled cells and the cell uptake of the nanoemulsion.

Additionally, ex vivo or in vivo targeted imaging and theranostic agents are described using the molecular platform that provide imaging of cells, tissues, and/or lesions having selected and prevalent molecular epitopes. For example targeting moieties can include antibodies (or fragments thereof), peptides, arginine-rich domains, cationic lipids, aptamers, etc.

Moreover, formulations of metalated fluorocarbons are envisioned that have a distinct signatures in MRI that can be used to image multiple cell types, the same cell type at different time points, or multiple molecular epitopes (e.g., multiple cell surface epitopes) within a subject. The molecular epitope can correspond to a diseased region or tissue in the subject, or a protein epitope associated with a disease or condition in the subject.

Other variants of the invention composition of matter include so called "theranostic" agents. Such theranostic agents may serve both as a therapeutic (or drug delivery vehicle) agent and an imaging probe (or diagnostic agent) that can help visualize the accurate delivery and dose of the therapy within the body. The pharmaceutical and/or diagnostic composition disclosed herein can be administered to a subject, the delivery of the composition (or cells labelled with the composition), and the dose/amount of the composition can be detected, monitored, tracked, and/or measured in the subject.

The invention also describes novel methods to assay the degree of cell labeling with the imaging probe, for example, as represented by the average total intracellular probe mass following labeling. Methods for quantitating labeled cells include methods known by those skilled in the art and used in MRI, PET, SPECT, US, and CT imaging.

In some embodiments, the compositions or formulations includes a first compound comprising $^{19}F$ have a first $^{19}F$ spectral frequency and a second compound comprising $^{19}F$ have a second $^{19}F$ spectral frequency that is different than the first $^{19}F$ spectral frequency. In some instances, the first compound includes a first metal ion and the second compound includes a second metal ion, such that the first and second metal ions are different. The first compound and the second compound can provide two separate, different spectral frequencies (i.e., two distinct imaging signatures) when detected simultaneously. In other cases, the first and second compounds are detected sequentially. The compounds can be detected using one imaging modality, e.g., MRI. In some cases, the compounds are detected using two different imaging modalities, such as, but not limited to, MRI and PET, MRI and SPECT, and PET and SPECT.

In some instances, the first $^{19}F$-containing compound labels a first cell type, and the second $^{19}F$-containing compound labels a second cell type. In certain cases, the first $^{19}F$-containing compound labels a cell type at a first time point, and the second $^{19}F$-containing compound labels the same cell type at a second time point (i.e., a later time point). In other cases, the first $^{19}F$-containing compound comprises a first targeting moiety that specifically binds to a first cell type, and the second $^{19}F$-containing compound comprises a second targeting moiety that specifically binds to a second cell type. The first and second cell types can be introduced into the subject. Optionally, the first and second cell types can be two different endogenous cell types located in the subject. In some embodiments, two, three or four different cell types can be introduced.

DETAILED DESCRIPTION

In one aspect of the invention, novel metal complexes are provided. In certain embodiments, the metal complexes are represented by formula $ML_x$, wherein M is an element with atomic number 12, 13, or from 23 to 31, or from 38 to 50, or from 56 to 83, L is a suitable ligand bearing a fluorinated substituent $R_F$, and x is an integer from 1 to 10. In certain embodiments, the subject ligands are monoanionic, and are represented, in their protonated form, by general structures 1-4:

(1)

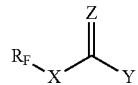

(2)

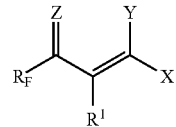

(3)

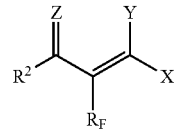

(4)

wherein $R_F$ represents

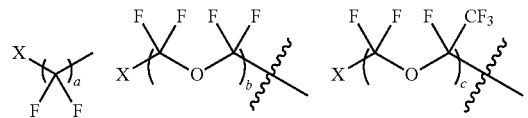

Z represents O, S, Se, or $NR^3$;

X and Y, for each occurrence, independently represent (A)-H, (A)-F, (A)-$OR^4$, (A)-$SR^4$, (A)-NHR4, or (A)-NR4R5, wherein A represents a spacer containing from 0 to 8 carbon or heteroatoms, in any combination, optionally substituted with groups $R^6$-$R^{20}$, as a straight chain or branched chain, or containing one or more rings, up to the limitations imposed by stability and the rules of valence; $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, for each occurrence, independently represent hydrogen, halogen, alkyl, alkenyl, alkynyl, hydroxyl, alkoxyl, silyloxy, amino, nitro, sulfhydryl, alkylthio, imine, amide, phosphoryl, phosphonate, phosphine, carbonyl, carboxyl, carboxamide, anhydride, silyl, thioalkyl, alkylsulfonyl, arylsulfonyl, selenoalkyl, ketone, aldehyde, ester, heteroalkyl, nitrile, guanidine, amidine, acetal, ketal, amine oxide, aryl, heteroaryl, azide, aziridine, carbamate, epoxide, hydroxamic acid, imide, oxime, sulfonamide, thioamide, thiocarbamate, urea or thiourea, fluoroalkyl, perfluoroalkyl, fluoroalkoxy, or perfluoroalkoxy;

a, b, and c independently, for each occurrence, represent integers from 1 to 20.

It is understood by skilled of the art that many of the ligands presented here may exist in tautomeric forms, or hydrated forms, for example:

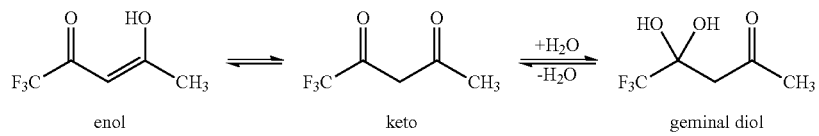

enol ⇌ keto ⇌ (+H₂O / -H₂O) geminal diol

In some cases one skilled in the art can prepare a gem-diol compound and use it for making metal complexes.

In some embodiments, the perfluorocarbon compound of the compositions described herein includes or is derived from a linear perfluoropolyether (PFPE), (PFPE-OMe), (PFPE-DEA), (PFOB), and PF2G.

Useful linear perfluoropolyethers are described in U.S. Pat. No. 8,449,866, the contents of which are herein incorporated by reference in their entirety. In some instances, the compositions include a metal-binding β-diketone conjugated to a linear perfluorocarbon. Useful perfluorocarbons include, but are not limited to, perfluoropolyether (PFPE), perfluoropolyether diethylamide (PFPE-DEA), perfluorooctyl bromide (PFOB), and perfluorotetraglyme (PF4G).

Perfluorocarbons can be any one of the following formulas (ii)-(vi):

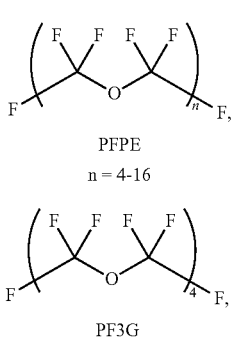

(ii) PFPE, n = 4-16

(iii) PF3G

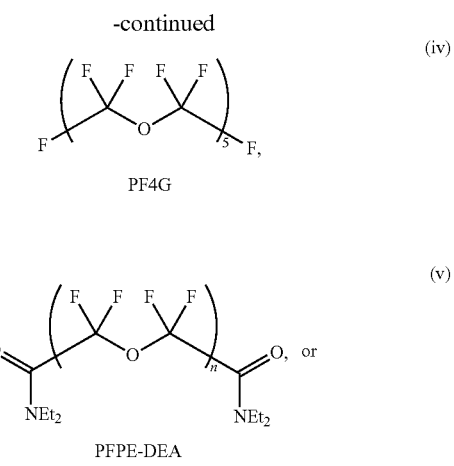

(iv) PF4G (v) PFPE-DEA (vi) PFOB

In some embodiments, metal-binding fluorinated diketones (FDK) are synthesized from PFPE-OMe (denoted below as $R_fCO_2Me$). The synthesis reaction can be as follows:

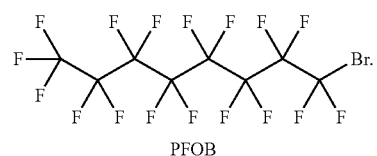

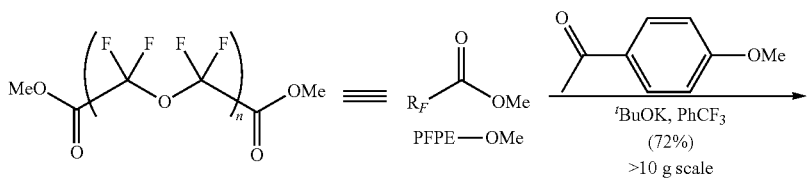

PFPE—OMe, $^t$BuOK, PhCF₃ (72%) >10 g scale

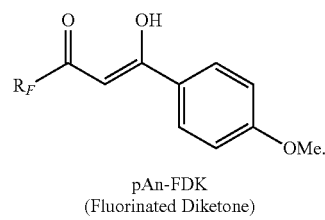

pAn-FDK (Fluorinated Diketone)

In some case, the metal-binding fluorinated diketone can have the formula:

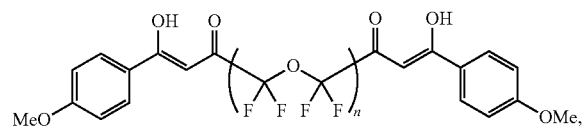

wherein n is 4 to 20, or in some cases 4 to 16.

In some case, the fluorinated diketone having any one of the following formulas can be used. The formulas include:

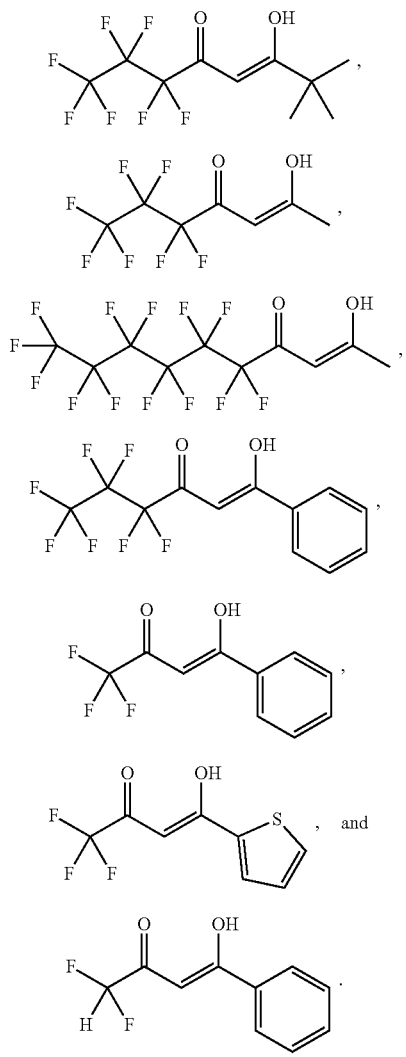

The fluorinated diketone and/or the perfluorocarbon can be formulated as an aqueous nanoemulsion, such as an oil-in-water colloidal suspension or an oil-in-water colloidal emulsion. Such nanoemulsions can also be formulated to include additional fluorocarbons or fluorocarbon blends (e.g., a mixture of two or more different fluorocarbons). The nanoemulsions can be metalated with a transition metal ion or a lanthanide ion. In some embodiments, the composition of the present invention includes iron(III) tris-β-diketonate and perfluoroether.

Metalation of fluorinated nanoparticles or nanoemulsion can impart contrast in multiple imaging modalities. Introduction of high quantities of metals into the fluorous phase is feasible using metal-binding ligands that are compatible with (soluble in) the fluorous phase. Strong, deleterious effects of high viscosity and high molecular weight on magnetic relaxation properties impose further limitations on the nature of ligands and metal chelates that would be suitable for enhancing magnetic resonance (MR) signals. Because of extremely poor solvent properties of fluorocarbons, conventional multidentate chelates (e.g., DTPA, DOTA) are expected to be poorly soluble in PFCs. However, due to sequestration of the metal into a separate, fluorous phase, it is permissible to use metal chelates formed by relatively weak ligands of low denticity; such complexes would not otherwise be stable in homogenous aqueous solutions containing, under biological conditions, large excess of competing ligands. Previous studies (Mumper and Jay, J. Phys. Chem. 1992, 96, 8626) showed that lanthanides are efficiently extracted into polymeric microspheres by lipophilic diketonate ligands. Reverse extraction of metals from fluorous to aqueous phase (thereafter referred to as metal leakage) can compromise imaging contrast and potentially cause toxicity. It is desirable to use metals known to be bioavailable and non-toxic (e.g. iron). Alternatively, one could use extremely small amount of metals detectable by means of the radioactive decay products (e.g. radioisotopes used in nuclear imaging) to generate contrast. In all cases, it is important to ascertain minimal rates of metal leakage from the fluorous phase of the nanoemulsions, as described herein.

In some embodiments, the fluorinated nanoparticles or nanoemulsion comprises a metalated perfluorocarbon blended (mixed) with a miscible nonmetalated perfluorocarbon. In certain embodiments, the fluorinated nanoparticles or nanoemulsion comprises a conjugated, metalated perfluorocarbon and a miscible unconjugated, nonmetalated perfluorocarbon. The ratio of metalated perfluorocarbon and nonmetalated perfluorocarbon in the nanoemulsion can be selected, adjusted, or tuned. Such a ratio can change (enhance or reduce) one or more properties of the nanoemulsion, including for example, signal intensity, SNR efficiency, detection sensitivity, detection limits, and/or stability, etc. In some embodiments, the signal intensity, SNR efficiency, detection sensitivity, detection limits, and/or stability can be enhanced. In some embodiments, the signal-to-noise ratio can be reduced. In some embodiments, blending and/or mixing can be employed to tune the formulation and increase or decrease potency, as needed, by one of skill in the art. In some embodiments, conjugated, metallated perfluorocarbon can be blended with like (i.e., miscible), unconjugated, nonmetallated perfluorocarbon. In some embodiments, such a blending ratio is tunable to increase/decrease 'potency' of the formulation. In some embodiments, the blending ratio is altered to increase the potency of the formulation. In some embodiments, the blending ratio is altered to decrease the potency of the formulation.

The compounds, compositions, and methods described herein can be used to track or trace cells by an imaging method, such as MRI, by detecting the cells associated (labeled) with the fluorine-19 containing compound or composition.

In some embodiments, the compounds, compositions, and methods are used to diagnose a disease by detecting or tracking the labeled cells, e.g., labeled immune cells. In some cases, the compounds and compositions can be administered to a subject to label a specific cell type. In other cases, cells of interest are labeled with the compounds and compositions in vitro, the labeled cells are administered to a subject, and the cells are detected using an imaging modality, e.g., MRI, PET, SPECT, CT, and ultrasound. The cells can be engineered cells, such as cells that express recombinant DNA encoding one or more recombinant proteins. In some cases, the recombinant protein is a targeting moiety, such as antibodies and fragments thereof, peptides, arginine-rich domains, cationic lipids, and aptamers.

The compounds, compositions, and methods described herein can be used for cytotherapy, e.g., cell-based treatment of a disease or condition. Cytotherapy includes introducing, administering, or grafting therapeutic cells into a tissue in order to treat a disease or condition. In other embodiments, the compounds and compositions are used to treat a disease or condition by administering or grafting cells labeled with the fluorine-19 containing compound or composition to a subject in need thereof. The labeled cells can be autologous or allogeneic cells. The cells can also be engineered cells, such as cells that express recombinant DNA encoding one or more recombinant proteins. In some cases, the recombinant protein is a therapeutic protein, e.g., antibody or a fragment thereof. The recombinant protein can be a targeting moiety, such as antibodies and fragments thereof, peptides, arginine-rich domains, cationic lipids, and aptamers.

The compounds and compositions can be an imaging probe that can be used for in vivo applications (e.g., diagnostic detection methods, cryotherapeutic methods, and the like). For instance, cells labeled with the compounds and compositions can be monitored after administration to a subject to determine the biodistribution of the labeled cells or uptake of the labeled cells in the subject.

Paramagnetic Relaxation Enhancement

In the presence of paramagnetic species in close proximity, the magnetic relaxation rates of atomic nuclei increases. Spin-lattice relaxation rate ($R_1=1/T$) and spin-spin relaxation time ($R_2=1/T_2$) are affected. Suitable metal cations for altering magnetic resonance relaxation rates include $VO^{2+}$, $Cr^{3+}$, $Mn^{2+}$, $Mn^{3+}$, $Fe^{3+}$, $Ni^{2+}$, $Cu^{2+}$, $Ce^{3+}$, $Pr^{3+}$, $Nd^{3+}$, $Sm^{3+}$, $Eu^{3+}$, $Gd^{3+}$, $Tb^{3+}$, $Dy^{3+}$, $Ho^{3+}$, $Er^{3+}$, $Tm^{3+}$, $Yb^{3+}$, $^{44}Sc^{3+}$, $^{52}Mn^{2+}$, $^{61}Cu^{2+}$, $^{64}Cu^{2+}$, $^{66}Ga^{3+}$, $^{68}Ga^{3+}$, $^{86}Y^{3+}$, $^{89}Zr^{4+}$, $^{67}Ga^{3+}$, $^{99m}Tc^{4+}$, $^{111}In^{3+}$ and $^{177}L^{3+}$. In some embodiments, the metals are $Mn^{2+}$, $Gd^{3+}$, and $Fe^{3+}$. In certain embodiments, the metal is $Fe^{3+}$. Typically, $Fe^{3+}$ is found in negative ($R_2$-enhancing) $^1H$ MRI contrast agents (superparamagnetic iron oxide, SPIO) and not typically considered as a positive ($R_1$-enhancing) agent. Conversely, $Gd^{3+}$ compounds are predominantly used as a positive $^1H$ contrast agents, although high concentrations of $Gd^{3+}$ are known to cause negative contrast. The unexpected discovery we made using metalated fluorocarbons was the superiority of $Fe^{3+}$ as $R_1$ agent, while $Gd^{3+}$ acted as $R_2$ agent, effectively a signal quencher. In some embodiments, a metal atom is attached (binds to) to the fluorinated diketone disclosed herein.

Positron Emission Tomography and Single Photon Computed Tomography

Positron emission tomography (PET) is based on coincidence detection of two 511 keV photons produced upon annihilation of a positron emitted upon the radioactive decay of certain nuclei. Suitable metals cations for preparing radiolabeled emulsions for PET include $^{44}Sc^{3+}$, $^{52}Mn^{2+}$, $^{61}Cu^{2+}$, $^{64}Cu^{2+}$, $^{66}Ga^{3+}$, $^{68}Ga^{3+}$, $^{86}Y^{3+}$, $^{89}Zr^{4+}$. Single photon computed tomography (SPECT) and related two-dimensional gamma scintigraphy are based on the detection of gamma-photons emitted upon the radioactive decay of certain nuclei. Suitable metals cations for preparing radiolabeled emulsions for SPECT imaging include $^{67}Ga^{3+}$, $^{99m}Tc^{4+}$, $^{m}In^{3+}$, $^{177}Lu^{3+}$. In some embodiments, long-lived isotopes $^{64}Cu^{2+}$ ($t_{1/2}$=12.7 h) and $^{89}Zr^{4+}$ ($t_{1/2}$=78.4 h) are used.

Detailed descriptions of uses of radioisotopes for cell tracking can be found, for example, in Yang et al., Radiology, 2016 May, 279(2):513-22; Bansal et al., EJNMMI Res. 2015 Mar. 28, 5:19; Normandin et al., Angew Chem Int Ed Engl, 2015 Oct. 26, 54(44): 13002-6; Tavare et al., Cancer Res, 2016 Jan. 1; 76(1):73-82; Sato et al., Radiology. 2015 May, 275(2):490-500; Kim et al., ACS Med Chem Lett, 2015 Apr. 7, 6(5):528-30; Greissinger et al., ProcNatl Acad Sci USA, 2015 Jan. 27, 112(4): 1161-6; and Graves et al., Bioconjug Chem. 2015 Oct. 21, 26(10):2118-24; all of which are incorporated by reference herein in their entireties.

X-Ray Computed Tomography (CT)

CT contrast agents are radioopaque, electron-dense materials that absorb X-ray radiation stronger than surrounding tissue, due to photoelectric effect. CT contrast agents typically contain high weight percentage of elements with high atomic number (Z) such as iodine (Z=53) or barium (Z=56). Suitable cations that bind to fluorinated ligands and generate CT contrast include $Ba^{2+}$, $La^{3+}$, $Ce^{3+}$, $Pr^{3+}$, $Nd^{3+}$, $Sm^{3+}$, $Eu^{3+}$, $Gd^{3+}$, $Tb^{3+}$, $Dy^{3+}$, $Ho^{3+}$, $Er^{3+}$, $Tm^{3+}$, $Yb^{3+}$, $Lu^{3+}$, $Hf^{4+}$, $Ta^{5+}$, $Pt^{2+}$, $Au^+$, $Bi^{3+}$, as well as metal, metal oxide, or metal sulfide nanoparticles containing elements with Z ranging from 56 to 83. It should be noted that certain fluorocarbons (e.g. PFOB) possess inherent CT contrast due to high density of the fluorinated liquids (typically 1.6-2.0 g/mL) and optional substitution with heavy halogens (Br, I). Metalation of fluorocarbons with high-Z elements will further boost radioopacity, and aid detectability in multispectral (colored) K-edge CT, for which conventional iodinated contrast agents are not suitable.

The perfluorinated compound and/or perfluorocarbon described herein are metalated (e.g., binds and tightly retains metal ions in the fluorous phase) with transition metal ions or lanthanide ions.

Ultrasonography

Ultrasound (US) contrast agents are widely employed to enhance images. These agents impart contrast by locally altering the acoustic impedance seen by the traveling ultrasonic wave in tissue media. The acoustic impendence is defined as the product of the medium density times the sound velocity. Fluorocarbons are intrinsically high-density materials. Moreover, metalated fluorocarbon emulsions, where the metal ion is fully coordinated by fluorophilic ligands, thereby crosslinking the fluorous molecules, will increase bulk modulus of elasticity and sound velocity within the droplet. Thus, the presence of the metalated fluorinated emulsion inside cells, or otherwise, will increase the acoustic impendence locally, thereby enhancing ultrasound contrast. In some compositions for ultrasound applications, diamagnetic metal ions are employed, i.e., ions with no unpaired d- or f-electrons.

Water Remediation

Water remediation, particularly the removal of unwanted heavy metals, is useful in many industrial processes and for environmental clean-up. Toxic metals include, for example, Al, An, Ba, Bi, Cd, Cr, Co, Cu, Au, Fe, Pb, Li, Mg, Hg, Ni, P, Se, Ag, Ti, Sn and Zn. Formulations of emulsions harboring metal binding ligands, but initially devoid of metal ions upon manufacture, can be used for this purpose. Such emulsions can scavenge metals from contaminated aqueous pools upon simple addition and mixing. The emulsion will take up (toxic) metal ions and internalize these inside the fluorous phase of the emulsion droplets thereby encapsulating the metal and rendering it non-reactive. Fluorous emulsions are dense, and they tend to settle and sediment over time, thereby removing the toxic metal from the bulk water. Moreover, emulsion droplets tend to coalesce over time due to the well known process of Ostwald ripening, and the net effect is that the metal-harboring fluorous oil will form macroscopic pools at the water's bottom. Useful references include, but are not limited to, Lusic and Grinstaff, Chem Rev, 2013 Mar. 13, 113(3):1641-66; Comode et al., Contrast Media Mol Imaging, 2014 January-February, 9(1):37-52; Meri et al., ACS Nano, 2015 Jun. 23, 9(6):6363-72; Betzer et al., ACS Nano, 2014 Sep. 23, 8(9):9274-85; Qie et al., Nanoscale, 2015 Feb. 14, 7(6):2480-8; Bonitatibus et al., ACS Nano, 2012 6 (8), 6650-6658; Yi et al., Nanoscale, 2015 Jan. 14; 7(2):542-50; and Sanchez et al., Journal of Fluorine Chemistry, 1995 August, 73(2):259-264; all of which are incorporated by reference herein in their entireties.

Synthesis of Metal-Binding Oils

Unless otherwise noted, all solvents and reagents were obtained from commercial sources (Sigma-Aldrich, St. Louis, Mo.) and used without further purification. PFPE-OMe (Exfluor Research, Round Rock, Tex.), a fluorinated derivative of polyethyleneglycol with $M_n$=600 (PEG-600) terminated with reactive ester groups, is a mixture of oligomers represented by a formula R'O($CF_2CF_2O)_n$ $CF_2CO_2Me$, where n=4-16, $M_n$=1750 g/mol, and R' represents $CF_2CO_2Me$, $CF_3$, or $CF_2CF_3$. The latter two functionalities originate from the cleavage of polymer backbone during fluorination, giving rise to minor peaks at −58, −90, and −93 ppm in $^{19}F$ NMR, and are chemically inert. PFPE-OMe oil was determined to be ca. 80% bifunctional; the balance was considered monofunctional, and contained 1.14 mmol reactive ester groups per gram. Trifluorotoluene, $PhCF_3$ (anhydrous, ≥99%) and methyl t-butyl ether, MTBE, were dried and stored over activated 4 Å molecular sieves.

Exemplary Embodiment 1

In a 100 mL round-bottom flask, PFPE-OMe (13.36 g, 15.23 mmol), p-methoxyacetophenone (2.86 g, 19.04 mmol, 1.25 equiv), and dry $PhCF_3$ (20 g) were combined. This colorless, homogeneous mixture was vigorously stirred, and solid potassium t-butoxide (2.14 g, 19.04 mmol, 1.25 equiv) was added portionwise under nitrogen over 5 min. The resulting warm orange heterogeneous mixture was immersed into a 50° C. oil bath for 30 min, until a deep red homogenous solution was obtained. Crude $^{19}F$ NMR of the reaction mixture (25 μL aliquot in 450 μL $CD_3OD$, homogeneous solution) reveals complete conversion of the starting $R_FOCF_2CO_2Me$ ($\delta_F$−78.33, ref. $PhCF_3$ at −64.00 ppm) to product diketonate ($\delta_F$—79.01). The warm reaction mixture was poured into a 40:1 hexanes:acetic acid solution (120 mL), providing a yellow-brown suspension. The suspension was filtered, and volatiles were removed in vacuo. The resulting orange-brown oil was washed with MeOH (3×20 mL) and dried under high vacuum to a constant mass, yielding 10.92 g (72%) of yellow oil containing <1 wt. % of starting acetophenone by $^1H$ NMR. No $CF_2CO_2Me$/ $CF_2CO_2K$ signals (−78.9 ppm) were observed by $^{19}F$ NMR in $CDCl_3$. Fluorous:organic partition coefficient (perflouoromethylcyclohexane:toluene)=1.87:1.

Exemplary Embodiment 2

This exemplary embodiment provides a way of synthesizing PFPE-derived fluorinated diketones without the use of fluorinated solvents. A vigorously stirred homogenous mixture of PFPE-OMe (10 g), MTBE (20 g), and p-methoxyacetophenone (2.14 g, 1.25 equiv.) immersed in a 40-45° C. oil bath was treated with solid sodium tert-butoxide (1.37 g, 1.25 equiv.) in one portion under nitrogen. Within 10 minutes, the added base dissolved, the solution turned orange, and small amounts of solid deposit was noted on the flask walls near liquid-gas interface. The reaction mixture was maintained at 40-50° C. for 3 hours, until $^1H$ and $^{19}F$ NMR of the sample (25 μL of reaction mixture in 450 μL of $CD_3OD$, homogenous solution) showed complete consumption of the starting ester, at which point the reaction mixture was worked up as described in Example 1, yielding 3.5 g of pure product.

Emulsion Preparation

In some embodiments, the nanoemulsion is prepared by microfluidization. An exemplary embodiment of method for preparing a useful emulsion is provided herein. The fluorocarbon oil blends were prepared from PFPE, PFPE-DEA (Exfluor), PFOB (Acros, Pittsburgh, Pa.), and pAn-FDK agents. Proportions (Table 1) were prepared gravimetrically in a 15 or 50 mL conical Falcon tube (Corning). Per 1 gram of PFC blend, 0.5 mL aqueous solution of Pluronic F68 (100 g/L) was added, and the mixture was vortexed at the highest speed. Water (8.5 mL) was added, followed by brief vortexing and ultrasonication (Omni Ruptor 250 W, 30% power, 2 minutes, Omni International, Kennesaw, Ga.). The crude emulsion thus obtained was passed 4-6 times through LV1 microfluidizer (Microfluidics, Westwood, Mass.) operating at 20,000 psi and filtered through a 0.2 m Supor membrane (Pall Corp. #4187, Port Washington, N.Y.) into sterile glass vials. The composition of PFC blends affects hydrophobicity, emulsion size, zeta-potential, viscosity, and NMR properties of the fluorinated labels. The emulsion size was determined by dynamic light scattering (DLS) on Malvern Zetasizer Nano ZS (Malvern, UK), measured one hour after preparation, and presented as $Z_{avg}$±½PDI width. The zeta potential was determined on the same instrument. DLS measurements on the emulsions shown below were repeated over up to 8 months of storage at 4° C. and no change (increase of 5% or more) was noted. The identity, concentration, and purity of the nanoemulsion can be determined by $^{19}F$ NMR.

TABLE 1

Composition and DLS analysis of metal-binding and control emulsions prepared at ca. 10 w/v % PFC.

| Emulsion (example) | Composition | Size (nm) | Zeta potential (mV) |
|---|---|---|---|
| 3 | 100% pAn-FDK | 163.4 ± 26.6 | −45.3 ± 7.2 |
| 4 | 50% pAn-FDK 50% PFPE-DEA | 142.4 ± 29.5 | −50.7 ± 8.9 |
| 5 | 100% PFPE-DEA | 161.2 ± 31.2 | −55.8 ± 6.4 |
| 6 | 50% pAn-FDK 50% PFPE | 139.8 ± 30.8 | −40.0 ± 13.1 |
| 7 | 100% PFPE | 176.1 ± 22.5 | −27.4 ± 10.4 |
| 8 | 32% pAn-FDK 68% PFOB | 192.2 ± 35.6 | −45.7 ± 11.3 |
| 9 | 50% pAn-FDK 25% PFPE, 25% PF4G | 183.0 ± 32.8 | −43.0 ± 10.3 |

Metalation

Pluronic F68-coated emulsions (such as exemplary emulsions 3-9 of Table 1) are easily metalated by a variety of d- and f-block metals in aqueous solution at optimal pH. The appropriate pH is determined by the hydrolysis propensity (acidity) of the aquated metal species, i.e. the equilibrium constant $K_h$ for the process below.

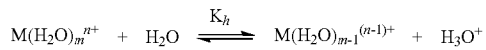

Empirically, the optimal pH for metalation of diketones was determined to be approximately equal to $pK_h$. The acidity and speciation of metal ions in aqueous solutions are known in the art. When pH is greater than $pK_h$, irreversible hydrolysis and formation of insoluble M(OH) can compete with metalation. In extreme cases (e.g., metalation with $FeCl_3$ at pH 7.4), the fluorinated droplets co-precipitate with the dense floc of metal hydroxide, limiting the yield of metalated emulsion. For most metals of relevance to imaging, rapid, quantitative metalation can be achieved at pH values between 1.0 and 7.4. The event and extent of metalation is determined by the change in optical (absorbance, fluorescence) or MR (relaxation times) properties, and can be analyzed kinetically. Minimal changes in colloidal properties are observed, unless metal cations prone to hydrolysis and aggregation (e.g., $Fe^{3+}$) are added in excess relative to the available ligand. After metalation, the pH and osmotic pressure emulsion is adjusted to the values optimal for cell labeling or parenteral administration with agents such as 4-(2-hydroxyethyl)-1-piperazineethanesulfonic acid (HEPES), tris-(2-hydroxymethyl)aminomethane (Tris), glycerol, propylene glycol, mannitol, sorbitol, or glucose.

Exemplary Embodiment 3

Compositions of emulsion (exemplary emulsions 4 and 5 of Table 1) were prepared and, by $^{19}F$ NMR analysis, determined to contain 45 g/L of $^{19}F$ and 35 mM of diketone ligand. A sample of the emulsion (40 µL) was treated with freshly prepared 50 mM $FeCl_3$ in $H_2O$ (4-40 µL). Rapid color change to orange-brown was observed. To this sample was sequentially added 50 mM pH 7.4 HEPES (120 NL), 0.1 wt % sodium trifluoroacetate ($CF_3CO_2Na$) in $D_2O$ (200 NL), and $H_2O$ (0-36 µL) to the final volume of 400 µL, and final concentration of $Fe^{3+}$ ranging from 0.5 to 5 mM. A control emulsion (exemplary emulsion 5 of Table 2) was treated similarly. The size of the emulsion was determined by DLS after prolonged storage at room temperature. The properties of metalated emulsion are provided in Table 2.

Exemplary Embodiment 4

Same emulsions (exemplary emulsions 4 and 5 of Table 2) were used, except they were metalated with $GdCl_3$. No visual change upon addition of metal was observed. To demonstrate distribution of metal species between aqueous and fluorous phases, the relaxation time $R_1$ of PFPE (fluorous phase) and $CF_3CO_2Na$ reference (aqueous phase) was measured after 2 hrs at 11.7 T.

TABLE 3

Composition of emulsions metalated with $GdCl_3$.

| Emulsion (example) | Final [$Gd^{3+}$] (mM) | Visual appearance after 2 hrs | $R_1$ (PFPE) ($s^{-1}$) | $R_1$ (TFA) ($s^{-1}$) |
|---|---|---|---|---|
| 4 | 0 | clear | 2.39 | 0.32 |
| 4 | 0.5 | clear | 16.2 | 0.33 |
| 4 | 0.8 | clear | 20.4 | 0.38 |
| 4 | 1.2 | clear | 24.5 | 0.37 |
| 4 | 1.6 | clear | 26.9 | 1.16 |
| 4 | 2.0 | clear | 27.7 | 7.00 |
| 4 | 3.0 | clear | 26.0 | 31.1 |
| 4 | 4.0 | clear | 26.5 | 47.0 |
| 4 | 5.0 | clear | 26.7 | 63.1 |
| 5 | 0 | clear | 2.37 | 0.32 |
| 5 | 0.5 | clear | 5.09 | 2.87 |
| 5 | 1.6 | clear | 5.36 | 49.7 |
| 5 | 3.0 | clear | 5.50 | 78.2 |

Exemplary Embodiment 5

The same emulsions as in the tables provided above were used, except metalated with $EuCl_3$. No color change was observed. On illumination with handheld 365 nm UV lamp, red photoluminescence of chelated $Eu^{3+}$ appeared after the addition of HEPES buffer.

Kinetic Measurements of Metal Uptake

Strong absorbance of aromatic diketone and its complexes permits facile kinetic investigation of metalation rates. In atypical measurement, emulsion from example 4 was diluted to 70 uM diketone (excess ligand, modeling radiolabeling conditions) into a solution of chosen pH and treated with 10 uM metal cations of relevance to medical imaging, including $Fe^{3+}$ (MRI), $Cu^{2+}$ (PET), $Ga^{3+}$ (PET, SPECT), $Sc^{3+}$ (PET), and $In^{3+}$ (SPECT). In all cases, UV-Vis spectral changes indicative of metal uptake into the fluorous phase were

TABLE 2

Composition of emulsions metalated with $FeCl_3$.

| Emulsion (example) | Final [$Fe^{3+}$] (mM) | Visual appearance after 2 hrs | $R_1$ at 11.7 T after 2 hrs ($s^{-1}$) | DLS size (nm) after 21 days | DLS size (nm) after 224 days |
|---|---|---|---|---|---|
| 4 | 0 | Clear | 2.39 | 146.1 ± 29.8 | 139.1 ± 28.3 |
| 4 | 0.5 | light-orange, clear | 30.6 | 142.4 ± 26.7 | 157.5 ± 37.5 |
| 4 | 0.8 | orange, clear | 54.1 | 141.1 ± 26.2 | 156.1 ± 35.8 |
| 4 | 1.6 | orange, clear | 73.4 | 143.1 ± 26.0 | 150.6 ± 31.9 |
| 4 | 3.0 | dark-orange, clear | 81.0 | 176.9 ± 27.5 | 216.2 ± 44.1 |
| 4 | 5.0 | dark-orange, turbid | 79.0 | 214.2 ± 61.4 | n/d, visible precipitate, could not be resuspended |
| 5 | 0 | clear | 2.37 | 161.4 ± 33.4 | 165.1 ± 32.5 |
| 5 | 0.8 | light-brown, slightly turbid | 2.58 | n/d | n/d |
| 5 | 1.6 | brown, turbid | 2.64 | n/d | n/d |
| 5 | 3.0 | brown, turbid | 2.75 | n/d | n/d | detected, proportional in magnitude to the amount of metal. For some metals, kinetic analysis was performed. The reaction time course fit well to a pseudo-first-order process with rate constant $k_{obs}$ (Table 4).

TABLE 4

Kinetics of emulsion metalation with various metal salts.

| Metal salt | final $[M^{3+}]$, uM | final [ligand], uM | Condition | $k_{obs}$ $(min^{-1})$ |
|---|---|---|---|---|
| $FeCl_3$ | 5 | 70 | pH 2.1 (8 mM HCl) | 0.79 |
| $FeCl_3$ | 10 | 70 | pH 2.1 (8 mM HCl) | 0.70 |
| $GaCl_3$ | 10 | 70 | pH 2.1 (8 mM HCl) | 0.043 |
| $InCl_3$ | 2 | 14 | pH ~5 (unbuffered $H_2O$) | >10 |
| $InCl_3$ | 10 | 70 | pH 7.4 HEPES | 0.0322 |

Purification

In some embodiments, the compounds described herein are purified to improve the product purity and increase the product yield. In some cases, the purification method includes substantially complete or complete removal of one or more reaction side products and/or unreacted starting materials. Such side products and unreacted starting materials include, but not limited to, PFPE methyl ester, p-acetanisole, potassium tert-butoxide, potassium methoxide, potassium acetate, and the like. Useful purification methods can include silica chromatography, neutral aluminum oxide chromatography, and fluorous solid phase extraction (F-SPE). In some embodiments, the purification method comprises F-SPE.

The compounds described herein can be substantially pure or completely pure, such that they are a substantially free or completely free of reaction side products and/or unreacted starting materials.

In some embodiments, the synthesis reaction is allowed to go to completion or substantially to completion prior to performing purification, e.g., chromatographic purification. The synthesis reaction can be the following:

The yield of synthesis can be optimized or increase by adding ethanol (instead of hexane) after the reaction is quenched with acetic acid. In some embodiments, a washing step comprising methanol is omitted. In other instances, inorganics of the reaction are removed by Buchner filtration, washing with water and brine, and celite filtration. In some embodiments, the pre-purification yield of the compound is at least about 80%, e.g., about 80%, 81%, 82%, 83%, 84%, 85%, 86%, 87%, 88%, 89%, 90%, 91%, 92%, 93%, 94%, 95%, 96%; 97%, 98%, 99%, or about 100%.

In other embodiments, the synthesis reaction is performed in trifluorotoluene. In other embodiments, the synthesis reaction is performed in methyl-tert-butyl ether (MTBE), instead of trifluorotoluene.

Leakage Assays

Metalated emulsions prepared as described above were incubated with a large excess of strong metal chelator (disodium ethylenediaminetetraacetate, EDTA) to simulate the biological conditions characterized by an abundance of competing ligands. Spectral changes that occurred upon metalation were reverted by the action of EDTA as metal decomplexation and trapping by EDTA proceeded. The rates of metal leakage were inversely correlated with ionic radius of the metal (Shannon R. D., Acta Crystallographica. (1976), A32, page 751-767; Table 5).

TABLE 5

Kinetics of metal leakage from the emulsion fluorous phase in the presence of 2.5 mM EDTA as determined by UV-Vis spectrophometry at room temperature.

| Metal cation | Ionic radius (pm) for coord. number = 6 | $t_{1/2}$ (min) |
|---|---|---|
| $Ga^{3+}$ | 62 | very slow (>1000) |
| $Fe^{3+}$ | 64.5 | very slow (>1000) |
| $Cu^{2+}$ | 73 | 33 |
| $Sc^{3+}$ | 74.5 | 77 |
| $In^{3+}$ | 80 | 2.1 |
| $Gd^{3+}$ | 93.8 | very fast (<1) |
| $Eu^{3+}$ | 94.7 | very fast (<1) |

Since $Fe^{3+}$-labeled nanoemulsion showed no decrease in characteristic absorbance of the $Fe^{3+}$ chelate even with prolonged exposure to EDTA, the samples were incubated in NMR tubes at 37° C. and measured the changes in relaxation rates over time. Decrease in relaxation rate $^{19}F$ $R_1$ would

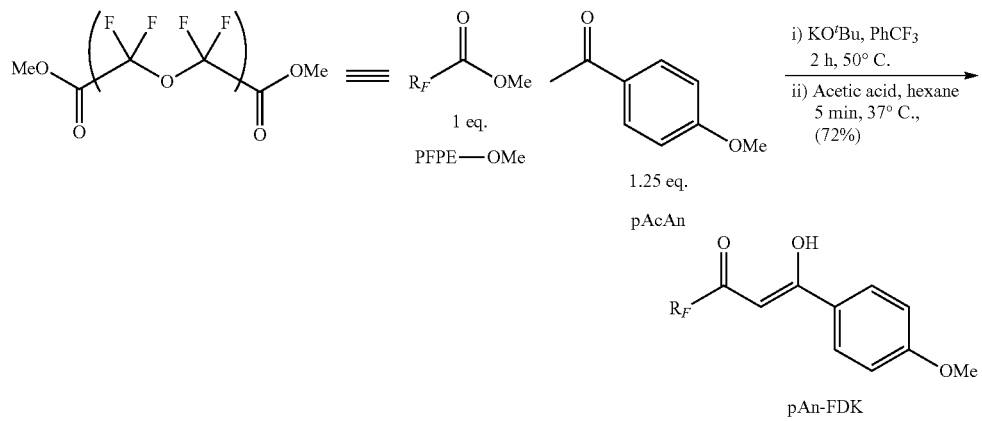

indicate sequestration of $Fe^{3+}$ to the aqueous phase, where it is too far from fluorine-19 nuclei to have an effect on $^{19}F$ R. PFPE-based nanoemulsions with compositions detailed in emulsion examples 4 and 8 (Table 1) showed ~20% decrease in $R_1$ over 2 weeks of incubation at 37° C. with 75 mM EDTA. Notably, this test proved more stringent than the conditions encountered during cell labeling; despite rapid leakage of lanthanides from the fluorous phase, $Eu^{3+}$ photoluminescence and elevated $^{19}F$ R due to the presence of Gd$^{3+}$ in the fluorous phase were reliably detected in cells labeled with emulsion from exemplary embodiment 4 (Table 3) and europium or gadolinium, respectively (see Cells and Labeling section).

Similar studies performed with small fluorinated diketones (H-fod, H-hhd, H-tdd, H-hfp, H-bta, H-tta, H-bda) revealed that they are highly effective at enhancing relaxation, but not stable enough under the conditions of EDTA competition and cell labeling. It may be necessary for sufficient stability to use fluorinated diketones with heavily fluorinated substituents that are well-miscible with other fluorinated agents known in the art to be useful for $^{19}$F MRI.

In some embodiments, the $t_{1/2}$ is >1000 minutes, less than 100 minutes, less than 90 minutes, less than 80 minutes, less than 70 minutes, less than 60 minutes, less than 50 minutes, less than 40 minutes, less than 30 minutes, less than 20 minutes, less than 10 minutes, less than 5 minutes, less than 2 minutes, or less than 1 minutes. In some embodiments, the $t_{1/2}$ is less than 90 minutes, less than 80 minutes, less than 70 minutes, less than 60 minutes, less than 50 minutes, less than 40 minutes, or less than 30 minutes.

Emulsions

The imaging reagent used in the subject methods is a fluorocarbon, i.e., a molecule including at least one carbon-fluorine bond. By virtue of the $^{19}$F atoms, the imaging reagents disclosed herein may be detected by $^{19}$F MRI and other nuclear magnetic resonance techniques, such as MRS techniques. In certain embodiments, a fluorocarbon imaging reagent will have one or more of the following properties: (1) reduced cytotoxicity; (2) a $^{19}$F NMR spectrum that is simple, ideally having a single, narrow resonance to minimize chemical shift artifacts; (3) high sensitivity with a large number of NMR-equivalent fluorine atoms in each molecule; and (4) formulated to permit efficient labeling of many cell types and not restricted to phagocytic cells. In some embodiments, the imaging reagent comprises a plurality of fluorines bound to carbon, e.g., greater than 5, greater than 10, greater than 15 or greater than 20 fluorines bound to carbon. In some embodiments, at least 4, at least 8, at least 12 or at least 16 of the fluorines have a roughly equivalent NMR chemical shift.

For labeling cells in culture, the imaging reagents can be employed in one or more of at least three modalities: (1) imaging reagents that are internalized or otherwise absorbed by target cells without the formation of any covalent or other binding association (first type); (2) imaging reagents that covalently attach to target cells (second type); and (3) imaging reagents coupled to molecules, such as antibodies or ligands, that bind to molecules present on the target cells (third type). In some embodiments, the imaging reagents that are internalized or otherwise absorbed by target cells without the formation of any covalent or other binding association (first type). In some embodiments, the imaging reagents that covalently attach to target cells (second type). In some embodiments, the imaging reagents coupled to molecules, such as antibodies or ligands, that bind to molecules present on the target cells (third type). In some embodiments, the imaging agent is a mixture of one or more of first, second, third types.

Imaging reagents of the first type include the perfluoro crown ethers and other perfluoropolyethers (PFPEs) that are taken up by cells and, preferably, are retained in the cell without degradation for a substantial period of time, e.g., having a half-life in the cell of at least 1 hour, at least 4 hours, at least about a day, at least about three days, or even at least about a week. In some embodiments, the imaging reagent does not interfere with ordinary cellular functions or exhibit cytotoxicity at the concentrations employed for labeling. As demonstrated herein, perfluoropolyethers show reduced toxic effect on the labeled cells.

Imaging reagents of the second type include electrophilic compounds that react with nucleophilic sites on the cell surface, such as exposed thiol, amino, and/or hydroxyl groups. Accordingly, imaging reagents such as maleimides, alkyl iodides, N-hydroxysuccinimide or N-hydroxysulfosuccinimide esters (NHS or sulfo-NHS esters), acyl succinimides, and the like can form covalent bonds with cell surfaces. Other techniques used in protein coupling can be adapted for coupling imaging reagents to cell surface proteins. See, for example, Means et al. (1990) Bioconjugate Chemistry 1:2-12, for additional approaches to such coupling.

Imaging reagents of the third type can be prepared by reacting imaging reagents of the second type not with the cells themselves, but with a functional moiety that is cell-targeting ligand or antibody. Suitable ligands and antibodies can be selected for the application of interest. For example, a ligand that selectively targets hematopoietic cells could be labeled with an imaging reagent as described herein and administered to a patient such as by infection. In some embodiments, the ligand can be a ligand that targets an immune cell.

Alternatively, an imaging reagent can be coupled to an indiscriminate internalizing peptide, such as antennapedia protein, HIV transactivating (TAT) protein, mastoparan, melittin, bombolittin, delta hemolysin, pardaxin, *Pseudomonas* exotoxin A, clathrin, Diphtheria toxin, C9 complement protein, or a fragment of any of these. Cells treated with this indiscriminate molecule ex vivo will absorb the imaging reagent. When such labeled cells are implanted into an animal, such as a mammal, the imaging reagent can be used to visualize and/or track the implanted cells by nuclear magnetic resonance techniques.

In one embodiment, the internalizing peptide is derived from the *Drosophila* antepennepedia protein, or homologs thereof. The 60-amino acid-long homeodomain of the homeo-protein antennapedia has been demonstrated to translocate through biological membranes and can facilitate the translocation of heterologous polypeptides to which it is coupled. See, for example, Derossi et al, (1994) J Biol Chem 269:10444-10450; and Perez et al. (1992) J Cell Sci 102: 717-722. It has been demonstrated that fragments as small as 16 amino acids long of this protein are sufficient to drive internalization. See, for example, Derossi et al, (1990) J Biol Chem 271:18188-18193.

Another example of an internalizing peptide is the HIV transactivator (TAT) protein. This protein appears to be divided into four domains (Kuppuswamy et al. (1989) Nucl. Acids Res. 17:3551-3561). Purified TAT protein is taken up by cells in tissue culture (Frankel and Pabo, (1989) Cell 55:1189-1193), and peptides, such as the fragment corresponding to residues 37-62 of TAT, are rapidly taken up by cell in vitro (Green and Loewenstein, (1989) Cell 55:1179-1188). The highly basic region mediates internalization and targeting of the internalizing moiety to the nucleus (Ruben et al., (1989) J. Virol 63:1-8). Peptides or analogs that include a sequence present in the highly basic region can be conjugated to fluorinated imaging reagents to aid in internalization and targeting those reagents to the intracellular milieu.

The present invention provides novel compositions comprising imaging reagents. For example, the present invention provides an aqueous composition comprising perfluoro-15-crown-5 ether or PFPE oxide, an emulsifier, a surfactant co-mixture, and an additive, in certain embodiments, the surfactant co-mixture comprises lecithin (i.e., lipoid egg phosphatidyl choline), cholesterol, and dipalmltoyl phosphatidylethanolamine (DPPE). In certain such embodiments, the surfactant co-mixture comprises 70 mol % of lecithin; 28 mol % of cholesterol; and 2 mol % of DPPE. In certain embodiments, the additive is propylene glycol.

As used herein, the term "PFPE oxide" refers to perfluoropoly(ethylene glycol) Dialkyl Ether (e.g., commercially available and can be purchased from Exfluor Inc., TX).

In certain embodiments, the emulsifier is also a non-ionic solubiliser. In certain embodiments, the emulsifier comprises glycerol polyethylene glycol ricinoleate. In certain such embodiments, the emulsifier further comprises fatty acid esters of polyethylene glycol, free polyethylene glycols, and ethoxylated glycerol. In certain embodiments, the emulsifier is prepared by reacting castor oil and ethylene oxide in a molar ratio of 1:35. Exemplary emulsifiers can be obtained from BASF Corporation and are sold under the trade name of Cremophor EL®.

In certain embodiments, the aqueous composition comprising perfluoro-15-crown-5 ether or PFPE oxide, Cremophor EL®, a surfactant co-mixture (e.g., comprising lecithin, cholesterol, and DPPE), and an additive (e.g., propylene glycol) comprises perfluor-15-crown-5 ether or PFPE oxide in the range of 20% to 50% w/v, such as 25% to 45% w/v, such as 30% to 40% w/v, such as 30%, 31%, 32%, 33%, 34%, 35%, 36%, 37%, 38%, 39% or 40% w/v. In certain such embodiments, the aqueous composition comprising perfluoro-15-crown-5 ether or PFPE oxide, Cremophor EL®, a surfactant co-mixture (e.g., comprising lecithin, cholesterol, and DPPE), and an additive (e.g., propylene glycol) comprises perfluor-15-crown-5 ether or PFPE oxide in the range of 35% to 36% w/v, such as 35.1%, 35.2%, 35.3%, 35.4%, 35.5%, 35.6%, 35.7%, 35.8%, or 35.9% w/v. In certain embodiments, the aqueous composition comprising perfluoro-15-crown-5 ether or PFPE oxide, Cremophor EL®, a surfactant co-mixture (e.g., comprising lecithin, cholesterol, and DPPE), and an additive (e.g., propylene glycol) comprises perfluor-15-crown-5 ether per PFPE oxide in 35.6% w/v.

In certain embodiments, the aqueous composition comprising perfluoro-15-crown-5 ether or PFPE oxide, Cremophor EL®, a surfactant co-mixture (e.g., comprising lecithin, cholesterol, and DPPE), and an additive (e.g., propylene glycol) comprises Cremophor EL® in the range of 1% to 10% w/v, such as 1% to 5% w/v, such as 1%, 2%, 3%, 4%, or 5% w/v. In certain embodiments, the aqueous composition comprising perfluoro-15-crown-5 ether or PFPE oxide, Cremophor EL®, a surfactant co-mixture (e.g., comprising lecithin, cholesterol, and DPPE), and an additive (e.g., propylene glycol) comprises Cremophor EL® in 3% w/v.

In certain embodiments, the aqueous composition comprising perfluoro-15-crown-5 ether or PFPE oxide, Cremophor EL®, a surfactant co-mixture (e.g., comprising lecithin, cholesterol, and DPPE), and propylene glycol comprises propylene glycol in the range of 1% to 10% w/v, such, as 1% to 5% w/v, such as 1%, 2%, 3%, 4%, or 5% w/v. In certain embodiments, the aqueous composition comprising perfluoro-15-crown-5 ether or PFPE oxide), Cremophor EL®, a surfactant co-mixture (e.g., comprising lecithin, cholesterol, and DPPE), and propylene glycol comprises propylene glycol in 2% w/v.

In certain embodiments, the aqueous composition comprising perfluoro-15-crown-5 ether or PFPE oxide, Cremophor EL®, an additive (e.g., propylene glycol), and a surfactant co-mixture, wherein the surfactant co-mixture comprises lecithin, cholesterol, and DPPE, comprises the surfactant co-mixture, wherein the surfactant co-mixture comprises lecithin, cholesterol, and DPPE, in the range of 1% to 10% w/v, such as 1% to 5% w/v, such as 1%, 2%, 3%, 4%, or 5% w/v. In certain embodiments, the aqueous composition comprising perfluoro-15-crown-5 ether or PFPE oxide, Cremophor EL®, an additive (e.g., propylene glycol), and a surfactant co-mixture, wherein the surfactant co-mixture comprises lecithin, cholesterol, and DPPE, comprises the surfactant co-mixture, wherein the surfactant co-mixture comprises lecithin, cholesterol, and DPPE, in 2% w/v.

In certain embodiments, the aqueous composition comprising perfluoro-15-crown-5 ether or PFPE oxide, Cremophor EL®, a surfactant co-mixture (e.g., comprising lecithin, cholesterol, and DPPE), and an additive (e.g., propylene glycol) further comprises polyethylamine. In certain such embodiments, the aqueous composition comprises polyethylamine in the range of 0.01% to 5.0% w/w. In certain embodiments, the aqueous composition comprising perfluoro-15-crown-5 ether or PFPE oxide, Cremophor EL®, a surfactant co-mixture (e.g., comprising lecithin, cholesterol, and DPPE), an additive (e.g., propylene glycol), and polyethylamine further comprises protamine sulfate. In certain such embodiments, the aqueous composition protamine-sulfate in the range of 0.01% to 5.0% w/w.

In certain embodiments, the present invention provides an aqueous composition comprising perfluoro-15-crown-5 ether or PFPE oxide in 35.6% w/v, Cremophor EL® in 3.0% w/v, a surfactant co-mixture (e.g., comprising lecithin, cholesterol, and DPPE) in 2.0% w/v, and an additive (e.g., propylene glycol) in 2.0% w/v.

The terms emulsion and nanoemulsion as used in this application are equivalent unless specifically stated otherwise. In certain embodiments, the emulsion may further comprise a block copolymer of polyethylene and polypropylene glycol. In certain embodiments, the emulsion may further comprise a Plutonic™ Nonionic Plutonic™ surfactants, polyethyleneoxide (PEO)/polypropyleneoxide (PPO)/polyethyleneoxide (PEO) block (ABA type), (PEO/PPO/PEO) block copolymers, exhibit a wide range of hydrophilicity/hydrophobicity as a function of the PEO/PPO ratio, so that one can expect to obtain different phase separated morphologies with polymers such as PLA as well as different degrees of hydration of the matrix. In particular, hydration plays an important role in determining polymer degradation via hydrolysis of the ester backbone. These polymeric surfactants exhibited minimal toxicities in vivo and some of them are in clinical use, as described by BASF Corporation in their 1989 Technical Bulletin; Attwood, et al., Int. J. Pharm. 26, 25 (1985); and U.S. Pat. No. 4,188,373 to Krezanoski. These materials can be obtained from BASF Corporation. In certain embodiments, emulsions of the present invention further comprise tri-block copolymer which comprises polyethyleneoxide and polypropyleneoxide.

In certain embodiments, emulsions of the present invention comprise a tri-block copolymer of poly(ethylene oxide)-poly(propylene oxide)-poly(ethylene oxide) (PEO-PPO-PEO) comprising 80% PEO content. In certain such embodiments, the hydrophilic-lipophilic balance (HLB) value of the tri-block copolymer is 29, wherein the HLB value can be calculated from the following equation:

$$HLB = -36\frac{m}{2n+m} + 33$$

where n represents the number of repeat units in the PEO segment of the polymer and m represents the number of repeat units in the PPO segment of the polymer. Exemplary tri-block copolymers can be obtained, from BASF Corporation and are sold under the trade name of Pluronic™ F68.

The present invention further provides an aqueous composition comprising perfluoro-15-crown-5 ether or PFPE oxide and the Pluronic™ F68. In certain embodiments, the aqueous composition comprising perfluoro-15-crown-5 ether or PFPE-oxide and the Pluronic™ F68, comprises perfluoro-15-crown-5 or PFPE oxide ether in the range of 10% to 20% w/w, such as 12% to 1% w/w, such as 12%, 13%, 14%, 15%, 16%, or 17% w/w. In certain embodiments, the aqueous composition comprising perfluoro-15-crown-5 ether or PFPE oxide and the Pluronic™ F68, comprises perfluoro-15-crown-5 ether or PFPE oxide in 15% w/w. In certain embodiments, the aqueous composition comprising perfluoro-15-crown-5 ether or PFPE oxide and the Pluronic™ F68, comprises the Pluronic™ F68 in the range of 0.1% to 2.0% w/w, such as 0.1% to 1.0% w/w, such as 0.1%, 0.2%, 0.3%, 0.4%, 0.5%, 0.6%, 0.7%, 0.8%, 0.9% or 1.0% w/w. In certain embodiments, the aqueous composition comprising perfluoro-15-crown-5 ether or PFPE oxide and the Pluronic™ F68, comprises the Pluronic™ F68 in 0.6% w/w.

In certain embodiments, the present invention provides an aqueous composition comprising perfluoro-15-crown-5 ether or PFPE oxide in 15% w/w and the Pluronic™ F68 in 0.6% w/w.

In certain embodiments, the aqueous composition comprising perfluoro-15-crown-5 ether or PFPE oxide and the Pluronic™ F68 further comprises protamine sulfate. In certain such embodiments, the aqueous composition comprising perfluoro-15-crown-5 ether or PFPE oxide, the Pluronic™ F68, and protamine sulfate comprises protamine sulfate in the range of 0.01% to 1.0% w/w, such as 0.01% to 0.5% w/w, such as 0.01% to 0.10% w/w, such as 0.01%, 0.02%, 0.03%, 0.04%, 0.05%, 0.06%, 0.07%, 0.08%, 0.09%, or 0.10% w/w. In certain embodiments, the aqueous composition comprising perfluoro-15-crown-5 ether or PFPE oxide, the Pluronic™ F68, and protamine sulfate comprises protamine sulfate in 0.04% w/w.

In certain embodiments, the aqueous composition comprising perfluoro-15-crown-5 ether or PFPE oxide and the Pluronic™ F68 further comprises polyethylamine. In certain embodiments, the present invention provides an aqueous composition comprising perfluoro-15-crown-5 ether or PFPE oxide in 15% w/w, the Pluronic™ F68 in 0.6% w/w, and protamine sulfate in 0.04% w/w.

The present invention also provides formulations of the compositions of the present invention as described above that are suitable for uptake by cells. For example, the compositions of the present invention may be formulated as an emulsion. As an example, the present invention provides an emulsion comprising an aqueous composition comprising perfluoro-15-crown-5 ether or PFPE oxide. Cremophor EL®, a surfactant co-mixture, and an additive. In certain embodiments, the surfactant co-mixture comprises lecithin, cholesterol, and dipalmitoyl phosphatidyl ethanolamine (DPPE). In certain such embodiments, the surfactant co-mixture comprises 70 mol % of lecithin; 28 mol % of cholesterol; and 2 mol % of DPPI. In certain embodiments, the additive is propylene glycol.

In certain embodiments of the foregoing emulsion, the aqueous composition comprising perfluoro-15-crown-5 ether or PFPE oxide, Cremophor EL®, a surfactant co-mixture (e.g., comprising lecithin, cholesterol, and DPPE), and an additive (e.g., propylene glycol) comprises perfluor-15-crown-5 ether or PFPE oxide in the range of 20% to 50% w/v, such as 25% to 45% w/v, such as 30% to 40% w/v, such as 30%, 31%, 32%, 33%, 34%, 35%, 36%, 37%, 38%, 39% or 40% w/v. In certain such embodiments of the foregoing emulsion, the aqueous composition comprising perfluoro-15-crown-5 ether or PFPE oxide, Cremophor EL®, a surfactant co-mixture (e.g., comprising lecithin, cholesterol, and DPPE), and an additive (e.g., propylene glycol) comprises perfluor-15-crown-5 ether or PFPE oxide in the range of 35% to 36% w/v, such as 35.1%, 35.2%, 35.3%, 35.4%, 35.5%, 35.6%, 35.7%, 35.8%, or 35.9% w/v. In certain embodiments of the foregoing emulsion, the aqueous composition comprising perfluoro-15-crown-5 ether or PFPE oxide, Cremophor EL®, a surfactant co-mixture (e.g., comprising lecithin, cholesterol, and DPPE), and an additive (e.g., propylene glycol) comprises perfluor-15-crown-5 ether or PFPE oxide in 35.6% w/v.

In certain embodiments of the foregoing emulsion, the aqueous composition comprising perfluoro-15-crown-5 ether or PFPE oxide, Cremophor EL®, a surfactant co-mixture (e.g., comprising lecithin, cholesterol, and DPPE), and an additive (e.g., propylene glycol) comprises Cremophor EL®, in the range of 1% to 10% w/v, such as 1% to 5% w/v, such as 1%, 2%, 3%, 4%, or 5% w/v. In certain embodiments of the foregoing emulsion, the aqueous composition comprising perfluoro-15-crown-5 ether or PFPE oxide, Cremophor EL®, a surfactant co-mixture (e.g., comprising lecithin, cholesterol, and DPPE), and an additive (e.g., propylene glycol) comprises Cremophor EL® in 3% w/v.

In certain embodiments of the foregoing emulsion, the aqueous composition comprising perfluoro-15-crown-5 ether or PFPE oxide, Cremophor EL®, a surfactant co-mixture (e.g., comprising lecithin, cholesterol, and DPPE), and propylene glycol comprises propylene glycol in the range of 1% to 10% w/v, such as 1% to 5% w/v, such as 1%, 2%, 3%, 4%, or 5% w/v. In certain embodiments of the foregoing emulsion, the aqueous composition comprising perfluoro-15-crown-5 ether or PFPE oxide, Cremophor EL®, a surfactant co-mixture (e.g., comprising lecithin, cholesterol, and DPPE), and propylene glycol comprises propylene glycol in 2% w/v.

In certain embodiments of the foregoing emulsion, the aqueous composition comprising perfluoro-15-crown-5 ether or PFPE oxide, Cremophor EL®, an additive (e.g., propylene glycol), and a surfactant co-mixture, wherein the surfactant co-mixture comprises lecithin, cholesterol, and DPPE, comprises the surfactant co-mixture, wherein the surfactant co-mixture comprises lecithin, cholesterol, and DPPE, in the range of 1% to 10% w/v, such as, 1% to 5% w/v, such as 1%, 2%, 3%, 4%, or 5% w/v. In certain embodiments of the foregoing emulsion, the aqueous composition comprising perfluoro-15-crown-5 ether or PFPE oxide, Cremophor EL®, an additive (e.g., propylene glycol), and a surfactant co-mixture, wherein the surfactant co-mixture comprises lecithin, cholesterol, and DPPE, comprises the surfactant co-mixture, wherein the surfactant co-mixture comprises lecithin, cholesterol, and DPPE, in 2% v/v.

In certain embodiments, the present invention provides an emulsion comprising an aqueous composition comprising perfluoro-15-crown-5 ether or PFPE oxide in 35.6% w/v, Cremophor EL® in 3.0% w/v, a surfactant co-mixture (e.g., comprising lecithin, cholesterol, and DPPE) in 2.0% w/v, and an additive (e.g., propylene glycol) in 2.0% w/v.

The present invention further provides an emulsion comprising an aqueous composition comprising perfluoro-15-crown-5 ether or PFPE oxide and the Pluronic™ F68. In certain embodiments of the foregoing emulsion, the aqueous composition comprising perfluoro-15-crown-5 ether or PFPE oxide and the Pluronic™ F68, comprises perfluoro-15-crown-5 ether or PFPE oxide in the range of 10% to 20% w/w, such as 12% to 17% w/w, such as 12%, 13%, 14%, 15%, 16%, or 17% w/w. In certain embodiments of the foregoing emulsion, the aqueous composition comprising perfluoro-15-crown-5 ether or PFPE oxide and the Pluronic™ F68, comprises perfluoro-15-crown-5 ether or PFPE oxide in 15% w/w. In certain embodiments of the foregoing emulsion, the aqueous composition comprising perfluoro-15-crown-5 ether or PFPE oxide and the Pluronic™ F68, comprises the Pluronic™ F68 in the range of 0.1% to 2.0% w/w, such as 0.1% to 1.0% w/w, such as 0.1%, 0.2%, 0.3%, 0.4%, 0.5%, 0.6%, 0.7%, 0.8%, 0.9% or 1.0% w/w. In certain embodiments of the foregoing emulsion, the aqueous composition comprising perfluoro-15-crown-5 ether or PFPE oxide and the Pluronic™ F68, comprises the Pluronic™ F68 in 0.6% w/w.

In certain embodiments, the present invention provides an emulsion comprising an aqueous composition comprising perfluoro-15-crown-5 ether or PFPE oxide in 15% w/w and the Pluronic™ F68 in 0.6% w/w.

In certain embodiments of the foregoing emulsion, the aqueous composition comprising perfluoro-15-crown-5 ether or PFPE oxide and the Pluronic™ F68 further comprises protamine sulfate. In certain such embodiments of the foregoing emulsion, the aqueous composition comprising perfluoro-15-crown-5 ether or PFPE oxide, the Pluronic™ F68, and protamine sulfate comprises protamine sulfate in the range of 0.01% to 1.0% w/w, such as 0.01% to 0.5% w/w, such as 0.01% to 0.10% w/w, such as 0.01%, 0.02%, 0.03%, 0.04%, 0.05%, 0.06%, 0.07%, 0.08%, 0.09%, or 0.10% w/w. In certain embodiments of the foregoing emulsion, the aqueous composition comprising perfluoro-15-crown-5 ether or PFPE oxide, the Pluronic™ F68, and protamine sulfate comprises protamine sulfate in 0.04% w/w.

In certain embodiments, the present invention provides an emulsion comprising an aqueous composition comprising perfluoro-15-crown-5 ether or PFPE oxide, in 15% w/w, the Pluronic™ F68 in 0.6% w/w, and protamine sulfate in 0.04% w/w.

In certain embodiments, the compositions and emulsions of the present invention comprise Cremophor® EL, a non-ionic solubiliser and emulsifier comprising polyethylene glycol ricinoleate, made by reacting castor oil with ethylene oxide in a molar ratio of 1:35. This material can be obtained from BASF Corporation.

In certain embodiments, the emulsion may further comprise a lipid. In certain embodiments of emulsions of the present invention that further comprise a lipid, the lipid is DMPC. In certain embodiments of emulsions of the present invention that further comprise a lipid, the emulsion further comprises a Pluronic™. In certain embodiments, the Pluronic™ is F68.

In certain embodiments, the emulsion may further comprise polyethylamine.

In certain embodiments, the emulsion may further comprise protamine sulfate. In certain embodiments of emulsions of the present invention that further comprise protamine sulfate, the emulsion further comprises a Pluronic™.

In certain embodiments, the Pluronic™ is F68. In certain embodiments, the emulsion of the present invention further comprises protamine sulfate.

Emulsions of the present invention will preferably have a distribution of droplet sizes that allow adequate cellular uptake. In certain embodiments, a uniform droplet size may be advantageous. The desired degree of uniformity of droplet size may vary depending upon the application. In certain embodiments, the emulsion has a mean droplet size less than 500 nm, or less than 400 nm, or less than 300 nm, or less than 200 nm in diameter. Optionally, 25%, or 50%, or 75% or more of the droplets will fall within the selected range. Droplet sizes may be evaluated by, for example, light scattering techniques or by visualizing the emulsion droplets using electron microscopy micrographs. In certain cell types that have a relatively small amount of cytoplasm, such as most stem cells, the emulsions have a mean droplet size of less than 200 nm, or less than 100 nm, or less than 50 nm in diameter. In some embodiments, the nanoemulsion droplets are about 50-300 nm in mean diameter, e.g., about 50-300 nm, 50-250 nm, 50-150 nm, 50-100 nm, 100-300 nm, 100-200 nm, 100-150 nm, 110-200 nm, 120-200 nm, 130-200 nm, 140-200 nm, 150-200 nm, 150-300 nm, 160-300 nm, 170-300 nm, or about 200-300 nm in mean diameter.

In certain embodiments, small droplet size is advantageous. In certain embodiments, small droplet size increases: circulation time in applications where the emulsion is injected intravenously (iv). In certain embodiments, droplets are separable from cells by circulation. In certain embodiments, small droplet size increases ex vivo cell labeling. In certain embodiments, small droplet size increases uniform labeling.

Emulsions for use in cells should preferably be stable at a wide range of temperatures. In certain embodiments, emulsions will be stable at body temperature (37° C. for humans) and at a storage temperature, such as 4° C. or room temperature (20-25° C.). For example, it will often be desirable to store the emulsion at a cool temperature, in the range of 2-10° C., such as 4° C., and then warm the emulsion to room temperature (e.g., 18 to 28° C., and more typically 20 to 25° C.). After labeling of cells, the emulsion will experience a temperature of about 37° C. Accordingly, a emulsion will retain the desired range of droplet sizes at temperatures ranging from refrigeration temperatures up to body temperature. In certain embodiments, the emulsion is stable at temperatures ranging from 4° C. to 37° C.

In certain embodiments, the emulsion has a polydispersity index ranging from 0.1 to 0.2.

The properties of an emulsion may be controlled primarily by the properties of the imaging reagent itself, the nature of surfactants and/or solvents used, and the type of processing device (e.g., sonicator, Microfluidixer, homogenixer, etc.). Methods for forming emulsions with certain PFPE molecules are extensively described in U.S. Pat. Nos. 5,330,681 and 4,990,283; herein incorporated by reference in their entireties. A continuous phase of a polyhydroxylated compound, such as polyalcohols and saccharides in concentrated aqueous solution may be effective. The following polyalcohols and saccharides have proved to be particularly effective; glycerol, xylitol, mannitol, sorbitol, glucose, fructose, saccharose, maltitol, dimer compounds of glycerol (diglycerol or bis(2,3-dihydroxypropyl) ether, solid water soluble polyhydroxylated compounds as sugars and glycerol condensation products as triglycerol and tetraglycerol. The dispersion in emulsion may be performed in the presence of conventional surfactants, including cationic, anionic, amphoteric and non-ionic surfactants. Examples of suitable surfactants include sodium lauryl sulphate, sulphosuccinate (sulphosuccinic hemiester), coco-amphocarboxyglycinate, potassium cetyl phosphate, sodium alkyl-polyoxyethylene-ether carboxylate, potassium benzalconium chloride, alkyl amidopropyl betaine, cetyl-stearilic ethoxylated alcohol, and sorbitan-ethoxylate(20)-mono-oleate Tween 20. While thermodynamic equations may be used to attempt to predict mixtures of imaging reagents that will give emulsions having the desired droplet sizes and stability, it is generally accepted that actual testing of various mixtures will be most effective. The emulsification of mixtures is simple and quick, permitting rapid testing of a wide range of combinations to identify those that give rise to emulsions that are suitable for use in the methods disclosed herein.

In the applications involving ex vivo labeling, some emulsions are designed to facilitate uptake of the imaging reagent by the subject cells. A surfactant may be designed to form stable emulsions that carry a large quantity of perfluoro-15-crown-5 ether or PFPE oxide into the aqueous phase. Additionally, it may have properties that increase the intracellular delivery of the emulsion droplets in the shortest possible incubation time. Increasing the perfluoro-15-crown-5 ether or PFPE oxide intracellular loading improves sensitivity to the labeled cells. Furthermore, minimizing the culture time can be important when working with the primary cells cultures. The efficiency of intracellular uptake depends on cell type. For example macrophages and some dendritic cells will endocytose almost any particulate, whereas other cell types of interest may only be weakly phagocytic. In either case the uptake efficiency can be boosted substantially by designing the surfactant so that the surface of the emulsion droplet has properties that promote cellular uptake in culture (i.e., "self-delivering" emulsion droplets) (see Janjie et al, JACS, 2008, 130 (9), 2832-2841 and U.S. Provisional Patent Application 61/062,710, both of which are incorporated by reference in their entirety). The emulsion droplet surface can be made to have lipophilic, or optionally cationic, properties via appropriate surfactant design. For example the surfactant can incorporate lipids, such as cationic or neutral lipids, oil-in-water colloidal emulsions, micelles, mixed micelles, or liposomes, that tend to bind to or fuse with the cell's surface, thereby enhancing emulsion droplet uptake. The emulsion droplet surface may also incorporate cell delivery signals such as polyamines. Examples include emulsions that have polyamines, such as polyethylenimine or protamine sulfate, incorporated into the emulsion droplet's surfactant layer during processing.

In certain embodiments, a colloidal system for use as a delivery vehicle in vitro and in vivo is a liposome (i.e., an artificial membrane vesicle). The preparation and use of such systems is well known in the art. Suitable cationic lipids are described in the following and are herein incorporated in their entirety; Felgner et al., 1987, PNAS 84, 7413-7417; U.S. Pat. Nos. 4,897,355; 5,279,833; 5,283,185; 5,334,761; 5,527,928; Bailey et al., U.S. Pat. Nos. 5,552, 155; and 5,578,475). Other approaches include incorporation into the surfactant peptides (e.g. oligo-Arg9 and TAT-like peptides) that facilitate entry into cells, or antibodies that target specific cell surface molecules. Additionally, in certain embodiments, one can incorporate small cationic proteins into the surfactant, such as protamine sulfate, to enhance cellular uptake. Protamine sulfate is non-toxic to cells and has FDA approval for use in humans as a heparin antagonist. In certain embodiments, colloidal dispersion systems are used, such as macromolecule complexes, nanocapsules, microspheres, and beads. Other approaches for enhancing uptake of the emulsified fluorocarbons, such as by using additional transfection agents or by using electroporation of the cells, is described herein.

In some embodiments, emulsions have "self-delivering" properties without having to add uptake enhancing reagents. Said emulsions are preferably stable and have a shelf-life of a period of months or years. In some embodiments, the stability is 3 months, 6 months, 9 months, 12 months, 24 months, or 48 months. In some embodiments, the stability is at 0° C., 10° C., 15° C., 20° C., 25° C., 30° C., 35° C., 37° C., and/or 40° C.

It is understood that surfactants and uptake enhancing reagents are not meant to be exclusive groups and in some cases they may be overlapping.

Additional descriptions of emulsions can be found, for example, in U.S. Pat. No. 9,352,057, the contents are herein incorporated by reference in its entirety.

Cells and Labeling

Methods described herein may be used with a wide range of cells, including both prokaryotic and eukaryotic cells, and including mammalian cells, such as human cells. In some embodiments, the cells are mammalian cells. In some embodiments, the cells are human cells. Technologies for cell preparation include cell culture, cloning, nuclear transfer, genetic modification and encapsulation. In some embodiments, the cells are engineered cells, such as genetically engineered or genetically modified cells. In some cases, the engineered cells are recombinant human cells, e.g., a human cell expressing recombinant DNA or a recombinant protein.

A partial list of suitable mammalian cells includes: blood cells, myoblasts, bone marrow cells, peripheral blood cells: umbilical cord blood cells, cardiomyocytes (and precursors thereof), chondrocytes (cartilage cells), dendritic cells, fetal neural tissue, fibroblasts, hepatocytes (liver cells), islet cells of pancreas, keratinocytes (skin cells), stem cells, and diseased cells, such as cancer cells. In certain embodiments, the cells to be used are a fractionated population of immune cells. Recognized subpopulations of immune cells include lymphocytes, such as B lymphocytes (Fc receptors, MHC class II, CD19+, CD21+), hELer T lymphocytes (CD3+, CD4+, CD8−), cytolytic T lymphocytes (CD3+, CD4−, CD8+), natural killer cells (CD16+), the mononuclear phagocytes, including monocytes, neutrophils and macrophages, and dendritic cells. Other cell types that may be of interest include eosinophils and basophils.

Cells may be autologous (i.e., derived from the same individual) or syngeneic (i.e., derived from a genetically identical individual, such as a syngeneic littermate or an identical twin), although allogeneic cells (i.e., cells derived from a genetically different individual of the same species) are also contemplated. Xenogeneic (i.e., derived from a different species than the recipient) cells, such as cells from transgenic pigs, may also be administered. When the donor cells are xenogeneic, the cells can be obtained from an individual of a species within the same order, more preferably the same superfamily or family (e.g., when the recipient is a human, the cells can be derived from a primate, more preferably a member of the superfamily Hominoidea).

Cells may, where medically and ethically appropriate, be obtained from any stage of development of a donor individual (e.g., a human donor), including prenatal (e.g., embryonic or fetal), infant (e.g., from birth to approximately three years of age in humans), child (e.g., from about three years of age to about 13 years of age in humans); adolescent (e.g., from about 13 years of age to about 18 years of age in humans), young adult (e.g., front about 18 years of age to about 35 years of age in humans), adult (from about 35 years of age to about 55 years of age in humans) or elderly (e.g., from about 55 years and beyond of age in humans).

In many embodiments, cells are labeled by contacting the cells with an emulsion of the imaging compound, such that the compound is taken up (e.g., internalized) by cells. In some embodiments, cells are labeled ex vivo or in vitro under certain conditions such that the imaging compound is internalized by the cells. Both phagocytic and non-phagocytic cells may be labeled by such a method. For example, as demonstrated in W2005072780, both dendritic cells (phagocytic) and gliosarcoma cells (non-phagocytic) can be labeled by contacting the cells with an emulsion of the imaging compound.

In certain embodiments, a method of the invention may comprise labeling cells in vivo with a $^{19}F$ imaging compound and detecting labeled cells in the subject. The imaging compound can be administered to the subject, e.g., human subject, by administration routes including, but not limited to, parenterally administration, e.g., intravenous administration. The cells to be labeled may be determined by specific properties of the cells such as phagocytic activity. The cells that are labeled may be controlled by the route of administration of the imaging reagent. The types of cells that are labeled may be controlled by the nature of the imaging compound. For example, simple colloidal suspensions of imaging compound will tend to be taken up more quickly by cells with phagocytic activity. As another example, an imaging compound may be formulated with or covalently bound to a targeting moiety that facilitates selective targeting of the imaging reagent to a particular population of cells. In certain embodiments, the imaging compound comprises a metalated fluorinated diketones.

In certain embodiments the cells to be labeled are stem cells. Stem cell therapies are commonly used as part of an ablative regimen for treatment of cancer with high dose radiation and/or chemotherapeutic agents. Ablative regimens generally employ hematopoietic stem cells, or populations of cells containing hematopoietic stem cells, as may be obtained, for example, from peripheral blood, umbilical cord blood or bone marrow. Cells of this type, or a portion thereof, may be labeled and tracked in vivo to monitor survival and engraftment at the appropriate location. Other types of stem cells are increasingly attractive as therapeutic agents for a wide variety of disorders.

As an example, cells may be mouse embryonic stem cells, or ES cells from another model animal. The labeling of such cells may be useful in tracking the fate of such cells administered to mice, optionally as part of a preclinical research program for developing embryonic stem cell therapeutics. Examples of mouse embryonic stem cells include: the JMI ES cell line described in M. Qiu et al., Genes Dev 9, 2523 (1995), and the ROSA line described in G. Friedrich, P. Soriano, Genes Dev 5, 1513 (1991), and mouse ES cells described in U.S. Pat. No. 6,190,910. Many other mouse ES lines are available from Jackson Laboratories (Bar Harbor, Me.). Examples of human embryonic stem cells include those available through the following suppliers; Arcos Bioscience, Inc., Foster City, Calif., CyThera, Inc., San Diego, Calif., BresaGen, Inc., Athens, Ga., ES cell International, Melbourne, Australia, Geron Corporation, Menlo Park, Calif., Goteborg University, Goteborg, Sweden, Karolinska Institute, Stockholm, Sweden, Maria Biotech Co. Ltd.—Maria infertility Hospital Medical Institute, Seoul, Korea, MizMedi Hospital—Seoul National University, Seoul, Korea, National Centre for Biological; Sciences/Tata Institute of Fundamental Research, Bangalore, India, Pochon CHA University, Seoul, Korea, Reliance Life Sciences, Mumbai, India, ReNeuron, Surrey, United Kingdom, StemCells, Inc., Palo Alto, Calif., Technion University, Haifa, Israel, University of California, San Francisco, Calif., and Wisconsin Alumni Research Foundation, Madison, Wis. In addition, examples of embryonic stem cells are described in the following U.S. patents and published patent applications: U.S. Pat. Nos. 6,245,566; 6,200,806; 6,090,622; 9,351,406; 6,090,622; 5,843,780; 20020045259; 20020068045; all of which are incorporated by reference herein in their entireties. In some embodiments, the human ES cells are selected from the list of approved cell lines provided by the National Institutes of Health (NIH) and accessible at the NIH embryonic Stem Cell Registry. In certain embodiments, an embryonic stem cell line is selected from the group comprising: the WA09 line obtained from Dr. J. Thomson (Univ. of Wisconsin) and the UC01 and UC06 lines, both on the current NIH registry.

In certain embodiments, a stem cell for use in disclosed methods is a stem cell of neural or neuroendocrine origin, such as a stem cell from the central nervous system (see, for example U.S. Pat. Nos. 6,468,794; 6,040,180; 5,753,506; 5,766,948), neural crest (see, for example, U.S. Pat. Nos. 5,589,376; 5,824,489), the olfactory bulb or peripheral neural tissues (see, for example. US Patent Publication Nos. 2003/0003579; 2002/0123143; 2002/0016002 and Gritti et al. 2002 J Neurosci 22 (2):437-45), the spinal cord (see, for example, U.S. Pat. Nos. 6,361,996, 5,851,832) or a neuroendocrine lineage, such as the adrenal gland, pituitary gland or certain portions of the gut (see, for example, U.S. Pat. No. 6,171,610 and PC12 cells as described in Kimura et al., 1994, J. Biol. Chem. 269: 1896-67). In some embodiments, a neural stem cell is obtained from a peripheral tissue or an easily healed tissue, thereby providing art autologous population of cells for transplant.

Hematopoietic or mesenchymal stem cells may be employed in certain disclosed methods. Recent studies suggest that bone marrow-derived hematopoietic (HSCs) and mesenchymal stem cells (MSCs), which are readily isolated, have a broader differentiation potential than previously recognized. Purified HSCs not only give rise to all cells in blood, but can also develop into cells normally derived from endoderm, like hepatocytes (Krause et ah, 2001, Cell 105: 360-77; Lagasse et al., 2000 Nat Med 6: 1229-34). Similarly, HSCs from peripheral blood and from umbilical cord blood are expected to provide a useful spectrum of developmental potential. MSCs appear to be similarly multipotent, producing progeny that can, for example, express neural cell markers (Pittenger et al., 1999 Science 284: 143-7; Zhao et al., 2002 Exp Neurol 174: 11-20). Examples of hematopoietic stem cells include those described in U.S. Pat. Nos. 4,714,680; 5,061,620; 5,437,994; 5,914,108; 5,925,567; 5,703,197; 5,750,397; 5,716,827; 5,643,741; 5,061,620. Examples of mesenchymal stem cells include those described in U.S. Pat. Nos. 5,486,350; 5,327,735, 5,942,235; 5,972,703, those described in PCT publication nos. WO 00/53705, WO 00/02654; WO 98/20907, and those described in Pittenger et al. and Zhao et al., supra.

Stem cell lines are preferably derived from mammals, such as rodents (e.g., mouse or rat), primates (e.g., monkeys, chimpanzees or humans), pigs, and ruminants (e.g., cows, sheep and goats), and particularly from humans. In certain embodiments, stem cells are derived from an autologous source or an HLA-type matched source. For example, stem cells may be obtained from a subject in need of pancreatic hormone-producing cells (e.g., diabetic patients in need of insulin-producing cells) and cultured to generate autologous insulin-producing cells. Other sources of stem cells are easily obtained from a subject, such as stem cells from muscle tissue, stem cells from skin (dermis or epidermis) and stem cells from fat.

In some embodiments, cells for administration to a human should be compliant with good tissue practice guidelines set by the U.S. Food and Drug Administration (FDA) or equivalent regulatory agency in another country. Methods to develop such a cell line may include donor testing, and avoidance of exposure to non-human cells and products.

Cells derived from a donor (optionally the patient is the donor) may be administered as unfractionated or fractionated cells, as dictated by the purpose of the cells to be delivered. Cells may be fractionated to enrich for certain cell types prior to administration. Methods of fractionation are well known in the art, and generally involve both positive selection (i.e., retention of cells based on a particular property) and negative selection (i.e., elimination of cells based on a particular property). As will be apparent to one of skill in the art, the particular properties (e.g., surface markers) that are used for positive and negative selection will depend on the desired population of cells. Methods used for selection/enrichment of cells may include immunoaffinity technology or density centrifugation methods. Immunoaffinity technology may take a variety of forms, as is well known in the art, but generally utilizes an antibody or antibody derivative in combination with some type of segregation technology. The segregation technology generally results in physical segregation of cells bound by the antibody and cells not bound by the antibody, although in some instances the segregation technology which kills the cells bound by the antibody may be used for negative selection.

Any suitable immunoaffinity technology may be utilized for selection/enrichment of the selected cells to be used, including fluorescence-activated cell sorting (FACS), panning, immunomagnetic separation, immunoaffinity chromatography, antibody-mediated complement fixation, immunotoxin, density gradient segregation, and the like. After processing in the immunoaffinity process, the desired cells (the cells bound by the immunoaffinity reagent in the case of positive selection, and cells not bound by the immunoaffinity reagent in the case of negative selection) are collected and either subjected to further rounds of immunoaffinity selection/enrichment, or reserved for administration to the patient.

Immunoaffinity selection/enrichment is typically carried out by incubating a preparation of cells comprising the desired cell type with an antibody or antibody-derived affinity reagent (e.g., an antibody specific for a given surface marker), then utilizing the bound affinity reagent to select either for or against the cells to which the antibody is bound. The selection process generally involves a physical separation, such as can be accomplished by directing droplets containing single cells into different containers depending on the presence or absence of bound affinity reagent (FACS), by utilizing an antibody bound (directly or indirectly) to a solid phase substrate (panning, immunoaffinity chromatography), or by utilizing a magnetic field to collect the cells which are bound to magnetic droplets via the affinity reagent (immunomagnetic separation). Alternately, undesirable cells may be eliminated from the preparation using an affinity reagent which directs a cytotoxic insult to the cells bound by the affinity reagent. The cytotoxic insult may be activated by the affinity reagent (e.g., complement fixation), or may be localized to the target cells by the affinity reagent (e.g., immunotoxin, such as ricin B chain).

Although it is expected that methods disclosed herein will be frequently used for in vivo monitoring of cells, it should be noted that the methodologies are equally effective for the monitoring of cells in culture (i.e., in vitro), in a tissue sample or other ex vivo cellular material. For therapeutic uses, cells may be labeled at a desired step during the preparation for administration to the patient.

A variety of methods may be used to label cells with imaging reagent. In general, cells will be placed in contact with imaging reagent such that the imaging reagent becomes associated with the cell. Conditions will often be standard cell culture conditions designed to maintain, cell viability. The term "associated" is intended to encompass any manner by which the imaging reagent and cell remain in sufficiently close physical proximity for a sufficient amount of time as to allow the imaging reagent to provide useful information about the position of the cell, whether in vivo or in vitro. Imaging reagent may be located intracellularly, e.g. after phagocytosis or surfactant mediated entry into the cell. Immune cells, such as dendritic cells, macrophages and T cells are often highly phagocytic and data presented herein and in other studies demonstrate that such cells, and other phagocytic cell types, are readily labeled. Other cell types, such as stem cells may also be labeled, regardless of phagocytic activity. Imaging reagent may be inserted into a cell membrane or covalently or non-covalently bound to an extracellular component of the cell. For example, certain linear fluorocarbons described herein may be derivatized to attach one or more targeting moiety. A targeting moiety will be selected to facilitate association of the imaging reagent with the cell to be labeled. A targeting moiety may be designed to cause non-specific insertion of the fibrocarbon into a cell membrane (e.g., a hydrophobic amino acid sequence or other hydrophobic moiety such as a palmitoyl moiety or myristoyl moiety) or to facilitate non-specific entry into the cell. A targeting moiety may bind to a cell surface component, as in the case of receptor ligands. A targeting moiety may be a member of a specific binding pair, where the partner is a cell surface component. The targeting moiety may be, for example, a ligand for a receptor, or an antibody, such as a monoclonal or polyclonal antibody or any of the various polypeptide binding agents comprising a variable portion of an immunoglobulin (e.g., Fv fragment, single chain Fv (scFv) fragment, Fab' fragment, F(ab')2 fragment, single domain antibody, camelized antibody, humanized antibody, diabodies, tribodies, tetrabodies). In certain embodiments, the fluorocarbon imaging reagent comprises perfluoro-15-crown ether.

Cellular labeling with fluorocarbons emulsions can also be facilitated using transfection agents to aid in cell delivery. Often transfection agents consist of cationic lipids, cationic liposomes, poly-cations, and the like. The transfection agent is pre-mixed with the fluorocarbon emulsion labeling agent, whereby it becomes associated with, or coats, the emulsion droplets. The transfection agent-treated emulsion droplets are then added to the cultured cells and incubated so that the cells become labeled. Common transaction agents include Lipofectamine (Invitrogen, Inc) FuGene, DOTAP (Roche Diagnostics, Inc.), and poly-L-lysine. Small proteins can also be used as transfection agents, such as many types of protamines. Protamines, the major DNA-landing proteins in the nucleus of sperm in most vertebrates, package the DNA in a volume less than 5% of a somatic cell nucleus. Protamines are simple proteins of low molecular weight that are rich in arginine and strongly basic. Commercially available protamines come from the sperm of salmon and certain other species of fish. The term "protamine" as used herein, refers to a low molecular weight cationic, arginine-rich polypeptide. The protamine molecule typically comprises about 20 to about 200 amino acids and is generally characterized by containing at least 20%, 50% or 70% arginine. Protamines are often formulated as salts, with one or more counter ions such as sulfate, phosphate and chloride.

Data provided in this application show that protamines (e.g., protamine sulfate) are highly effective in delivering PFPE fluorocarbon emulsion droplets to cultured cells. Suitable protamine sulfates can come from a variety of sources (e.g., salmon, herring, trout, etc.) and be of various grades and forms (e.g., USP, grades II, III, X, etc.), with and without histones or any recombinant derivative. Examples of other protamine solutions that may be used as transfection agents include protamine phosphate, protamine chloride, protamine sulfate-2, protamine sulfate-3, protamine sulfate-10, and protamine free base.

Data provided in this application shows self deliverable nanoemulsions prepared with fluorocarbon imaging reagents (e.g., perfluoro-15-crown-5 ether or PFPE oxide) and incorporate a Plutonic™ surfactant, optionally with Protamine Sulfate, or Cremophor EL® with an emulsifier and an additive. Simple co-incubation of cells with certain self-deliverable nanoemulsions provides sufficient cell labeling for imaging, without the need for transfection reagents.

Where cells are to be used in a therapeutic regimen, various methods have been used for delivery of cells including injections and use of special devices to implant cells in various organs. The present invention is not tied to any particular delivery method. Labeled cells may be monitored regardless of whether the cells are delivered directly to a particular site or delivered systemically. For example, labeled dendritic cells were successfully imaged following either a focal implantation directly into tissues or an intravenous injection, and T-cells were imaged following intraperitoneal injection. Cells may be inserted into a delivery device which facilitates introduction by injection or implantation into the subjects. Such delivery devices may include tubes, e.g., catheters, for injecting cells and fluids into the body of a recipient subject. In some embodiments, the tubes additionally have a needle, e.g., a syringe, through which the cells of the disclosure can be introduced into the subject at a desired location. The cells may be prepared for delivery in a variety of different forms. For example, the cells may be suspended in a solution or gel or embedded in a support matrix when contained in such a delivery device. Cells may be mixed with a pharmaceutically acceptable carrier or diluent in which the cells of the disclosure remain viable. Pharmaceutically acceptable carriers and diluents include saline, aqueous buffer solutions, solvents and/or dispersion media. The use of such earners and diluents is well known in the art. The solution is preferably sterile and fluid. Preferably, the solution is stable under the conditions of manufacture and storage and preserved against the contaminating action of microorganisms such as bacteria and fungi through the use of, for example, parabens, chlorobutanol, phenol, ascorbic acid, thimerosal, and the like. Solutions of the disclosure may be prepared by Incorporating cells as described herein in a pharmaceutically acceptable carrier or diluent and, as required, other ingredients enumerated above, followed by filtered sterilization.

Additional descriptions of useful cells and methods of labeling said cells can be found, for example, in U.S. Pat. No. 9,352,057, the contents of which is herein incorporated by reference in its entirety.

Nuclear Magnetic Resonance Imaging Techniques

As described herein, also referred to herein as a type of imaging modality, nuclear magnetic resonance techniques may be used to detect populations of labeled cells. The term "detect" is used to include any effort to ascertain the presence or absence of a labeled molecule or cell, particularly by a nuclear magnetic resonance technique. The term "detect" is also intended to include more sophisticated measurements, including quantitative measurements and two- or three-dimensional image generation. For example, MRI may be used to generate images of such cells. In many instances, the labeled cells may be administered to a living subject. Following administration of the cells, some portion of the subject, or the entire subject, may be examined by MRI to generate an MRI data set. In other instances, the emulsion is injected directly iv, and the subject is subsequently imaged at one or more time points. A "data set", as the term is used herein, is intended to include raw data gathered during magnetic resonance probing of the subject material, the acquisition parameters, as well as information processed, transformed or extracted from the raw data. The raw data includes transient signals obtained by MRI (magnetic resonance imaging)/MRS (magnetic resonance spectroscopy), including the free-induction decays, spin-echoes, stimulated-echoes, and/or gradient echoes. Examples of processed information include two-dimensional or three-dimensional pictorial representations of the subject material. The processed information may also include magnitude images, the real and imaginary image components, as well as the associated phase map images. Another example of extracted information is a score representing the amount or concentration of imaging reagent or $^{19}F$ signal in the subject material. By using the amount of $^{19}F$ signal in the subject material, and a calibration of the mean amount of imaging reagent per cell pre-implantation (m the case of ex vivo labeling), one can estimate the absolute number of cells in the subject material. The amount of $^{19}F$ signal present in a subject material can be represented or calculated in many ways; for example, the average signal-to-noise-ratio (SNR) of the $^{19}F$ signal for a region of interest (ROI) may be measured and used to calculate the abundance of labeled cells. In certain embodiments, the average intensity, or pixel- or voxel-wise summation of the $^{19}F$ signal may be used to calculate the abundance of labeled cells. This type of data may be gathered at a single region of the subject, such as, for example, the spleen or another organ of particular relevance to the labeled cells. Labeled cells may be examined in contexts other than in the subject. It may be desirable to examine labeled cells in culture. In certain embodiments, labeled cells may be applied to or generated within a tissue sample or tissue culture, and labeled cells may therefore be imaged in those contexts as well. For example, an organ, tissue or other cellular material to be transplanted may be contacted with an imaging reagent to generate labeled cells prior to implantation of such transplant in a subject.

In general, labeling agents of the disclosure are designed for use in conventional MRI detection systems. In the most common implementation of MRI, one observes the hydrogen nucleus (proton, $^{1}H$) in molecules of mobile water contained in subject materials. To detect labels disclosed herein, an alternate nucleus is detected, $^{19}F$. $^{19}F$ MRI has only slightly less intrinsic sensitivity compared to $^{1}H$; the relative sensitivity is approximately 0.83. Both have a nuclear spin of +½. The natural isotopic abundance of $^{19}F$ is 100%, which is comparable to 99.985% for $^{1}H$. The physical principles behind the detection and image formation are the same for both $^{1}H$ and $^{19}F$ MRI. The subject material is placed in a large static magnetic field. The field tends to align the magnetic moment associated with the $^{1}H$ or $^{19}F$ nuclei along the field direction. The nuclei are perturbed from equilibrium by pulsed radio-frequency (RF)

radiation at the Larmor frequency, which is a characteristic frequency proportional to the magnetic field strength where nuclei resonantly absorb energy. Upon removing the RF, the nuclei induce a transient voltage in a receiver antenna; this transient voltage constitutes the nuclear magnetic resonance (NMR) signal. Spatial information is encoded in both the frequency and/or phase of the NMR signal by selective application of magnetic field gradients that are superimposed onto the large static field. The transient voltages are generally digitized, and then these signals may be processed by, for example, using a computer to yield images.

At constant magnetic field strength, the Larmor frequency of $^{19}F$ is only slightly lower (about 6%) compared to $^1H$. Thus, it is straightforward to adapt conventional MRI scanners, both hardware and software, to acquire $^{19}F$ data. The $^{19}F$ detection may be coupled with different types of magnetic resonance scans, such as MRI, MRS or other techniques. Typically, it will be desirable to obtain a $^1H$ MRI image to compare against the $^{19}F$ image. In a living organism or other biological tissue, the proton MRI will provide an image of the subject material and allow one to define the anatomical context of the labeled cells detected in the $^{19}F$ image. In some embodiments, data is collected for both $^{19}F$ and $^1H$ during the same session; the subject is not moved during these acquisitions to better ensure that the two data sets are in spatial registration. Normally, $^{19}F$ and $^1H$ data sets are acquired sequentially, in either order. An RF coil (i.e., antenna) can be constructed that can be electrically tuned from the $^{19}F$ and $^1H$ Larmor frequency. Tuning between these two frequencies can be performed manually (e.g. via an electro-mechanical variable capacitor or inductor), or electrically, via active electronic circuitry. Alternatively, with appropriate modifications to the hardware and/or software of the MRI instrument, both data sets can be acquired simultaneously, for example, to conserve imaging time. Simultaneous acquisition of the $^{19}F$ and $^1H$ data sets require an RF coil or antenna that can be electrically tuned simultaneously to the $^{19}F$ and H Larmor frequency (i.e., a double-tuned coil). Alternatively the RF coil can be "broadband," with one broadly-tuned electrical resonance that covers both Larmor frequencies (i.e., $^{19}F$ and $^1H$). Other imaging techniques, such as fluorescence detection may be coupled with $^{19}F$ MRI. This will be particularly desirable where a fluorocarbon imaging reagent has been derivatized with a fluorescent moiety. In other embodiments, the $^{19}F$ MRI scan may be combined with a PET scan in the same subject or patient by using dual-model radioactive $^{18}F/^{19}F$ fluorocarbon labeling reagents as described herein.

MRI examination may be conducted according to any suitable methodology known in the art. Many different types of MRI pulse sequences, or the set of instructions used by the MRI apparatus to orchestrate data collection, and signal processing techniques (e.g., Fourier transform and projection reconstruction) have been developed over the years for collecting and processing image data (for example, see Magnetic Resonance Imaging, Third Edition, editors D. D. Stark and W. G. Bradley, Mosby, Inc., St. Louis Mo. 1999). The reagents and methods of this disclosure are not tied to any particular imaging pulse sequence or processing method of the raw NMR signals. For example, MRI methods that can be applied to this disclosure broadly encompasses spin-echo, stimulated-echo, gradient-echo, free-induction decay based imaging, and any combination thereof. Fast imaging techniques, where more than one line in k-space or large segments of k-space are acquired from each excited signal, are also highly suitable to acquire the $^{19}F$ (or $^1H$) data. Examples of fast imaging techniques include fast spin-echo approaches (e.g., FSE, turbo SE, TSE, RARE, or HASTE), echo-planar imaging (EPI), combined gradient-echo and spin-echo techniques (e.g., GRASE), spiral imaging, and burst imaging. The development of new and improved pulse sequence and signal processing methods is a continuously evolving field, and persons skilled in the art can devise multiple ways to image the $^{19}F$ labeled cells in their anatomical context.

As another example of a nuclear magnetic resonance technique, MRS can be used to detect the presence of fluorocarbon-labeled cells in localised tissues or organs. Normally MRS methods are implemented on a conventional MRI scanner. Often the localized volume of interest (VOI) is defined within a conventional anatomical $^1H$ MRI scan. Subsequently, the magnitude of the $^{19}F$ NMR signal observed within the VOI is directly related to the number of labeled cells, and/or the mean concentration of PFPE per cell present in the tissue or organ. Methods for isolating a VOI within a much larger subject are well known the art (for example, Magnetic Resonance Imaging, Third Edition, Chapter 9, Editors D. D. Stark and W. G. Bradley, Mosby, Inc., St Louis Mo. 1999). Examples include using a localised RF surface coil near the VOI, surface spoiling, surface coil Bi-gradient methods, slice-selective $B_0$-gradient techniques, STEAM, PRESS, image selective in vivo spectroscopy (ISIS), and magnetic resonance spectroscopic imaging (MRSI).

The development of new and improved pulse sequence and signal processing methods is continuously evolving for MRS, and persons skilled in the art can devise multiple ways to detect the $^{19}F$ NMR signals emanating from the fluorocarbon labeled cells in VOIs.

In some embodiments, the subject material is a fixed or otherwise preserved specimen of tissue that has been biopsied or necropsied from the animal or human. The subject material is then subjected to conventional high-resolution, one or multi-dimensional, liquid state $^{19}F$ NMR to determine the amount of fluorine present in the sample. The fluorine content is directly related to the number of labeled cells in the subject material specimen. In the case of in situ labeling of resident phagocytes (e.g., monocytes, macrophage, neutrophil, cells of the liver) with fluorine emulsion as described above (e.g., using nanoemulsion 3), the amount of $^{19}F$ measured in the sample is directly proportional to the number of these phagocytes present in the tissue. In this way one can assay the relative amount of inflammation in the intact tissues without having to use histology or any other destructive and time-consuming techniques. In certain embodiments, to analyze the $^{19}F$ content of the tissue, one uses one-dimension $^{19}F$ NMR. In certain embodiments, a $^{19}F$ reference compound will be added to the sample of known number of $^{19}F$ spins that has a chemical shift that is different than the composition of the cell labeling emulsion (see below). In certain embodiments, the relative integrated areas under the emulsion peak and reference peak can be used to calculate the absolute number of fluorines present in the tissue sample. In certain embodiments, the weight of the tissue sample can also be incorporated into the calculation to extract the mean fluorine density of the tissue sample, and this parameter can be considered a quantitative index of inflammation or "inflammation index".

In certain embodiments the disclosure provides a method of quantifying the numbers of labeled cells in vivo or in subject materials within an ROI. An ROI may include all labeled cells in a subject or labeled cells in specific organs such as the pancreas, specific tissues such as lymph nodes, or any region or of one or more voxels showing detectable MRI/MRS $^{19}$F signal. A ROI can be an otherwise undefined area beyond a particular experiment. There are a number of ways that labeled cells may be quantified in the subject materials or in vivo, as described herein.

In the case or ex vivo labeling, calibrating the mean "cellular dose" of $^{19}$F labeling agent pre-implantation of a particular cell population is often a pre-requisite for quantitative cell determinations in subject materials or the patient. It is anticipated that different cell types have different inmate abilities to take up the labeling agents in vitro, and thus the cellular dose of the labeling agent will also vary. Furthermore, different cells of the same type acquired from different sources (e.g., different patients) may have different affinities for the labeling agent. Thus a cellular dose calibration may be required. This calibration may be used, initially, to modify the labeling protocol (i.e., incubation conditions, duration of time that cells are incubated with labeling fluorocarbon emulsion, concentration of fluorocarbon emulsion in culture medium during labeling, etc.) to achieve a certain range of cellular dose before labeled cells are actually used in a subject to be imaged. Alternatively, one can fix the labeling conditions and protocol and measure the mean value $^{19}$F labeled per cell, as is, for subsequent quantification in the subject to be imaged. In certain embodiments the mean number of $^{19}$F molecules (F's) per cell of a labeled cell population is measured (i.e., calibrated) in vitro prior to administration of the cells to the subject or patient. In certain embodiments the mean number of $^{19}$F molecules (F's) per cell of a labeled cell population is calibrated in a test population of cells of a particular type, not necessarily destined for a patient, but used to calibrate cellular dose of labeling agent as a consequence of a particular labeling protocol or set of conditions; optionally, the value of cellular dose is then used for future labeling and in vivo imaging experiments in the same population type of cells with the same labeling protocol.

The cellular dose of labeling agent can be assayed in vitro using a variety of quantitative techniques. For example, one can use a one-dimensional (1D) $^{19}$F NMR spectrum obtained from a cell pellet, cell suspension, or cell lysate, of a known number of labeled cells. From this spectrum, one can calculate the integrated area of the $^{19}$F spectrum or a portion thereof, originating from the labeling reagent associated with the cells. The integrated area of the $^{19}$F spectrum, denoted $S_{cells}$, is directly proportional to the total amount of $^{19}$F in the cell pellet, suspension, or lysate. To measure the absolute number of $^{19}$F nuclei, the measured S.sub.cells may be normalized to a $^{19}$F standard. A $^{19}$F standard can be, for example, a solution of a known volume and concentration of a fluoro-chemical, where one can calculate the total number of $^{19}$F nuclei in the standard, denoted $F_{scan}$. A suitable fluoro-chemical reference ideally has a simple $^{19}$F NMR spectrum, preferable with a single narrow resonance (e.g. trifluoroacetic acid or TFA) and optionally a $^{19}$F chemical shift that is significantly different than the labeling fluorocarbon. The $^{19}$F standard can be placed in the same NMR tube as the labeled cell material being measured, in a separate tube, or optionally can be measured in a separate experiment using the same NMR instrument. The integrated area of the spectrum from the $^{19}$F standard, denoted $S_{stan}$, can then be measured. Subsequently, the mean number of $^{19}$F per labeled cell, denoted F, can be calculated, for example using the following formula:

$$F_c = \frac{S_{cells}}{S_{stan}} F_{stan} \frac{1}{N_{cells}}$$

where $N_{cells}$ is the number of labeled cells contained in the in vitro test sample. Quantitative NMR methods for $^{19}$F and other nuclei are well known in the art, and those skilled can devise many variations to the cellular dose calibration procedure described above. Besides $^{19}$F NMR, there are other quantitative methods that can be used to assay the cellular dose of the labeling reagent. For example, a reagent may be labeled fluorescently, luminescently, optically, or radioactively (see, U.S. Patent Publication Nos. 2007/0258886 and 2013/0343999, herein incorporated by reference in their entireties).

Similarly, in the case of in situ cell labeling of circulating phagocytes following iv injection of emulsion, to measure the effective cell labeling, one can extravasate a portion of peripheral blood from the subject and measure the effective cell loading of leukocytes using the methods described above. Furthermore, one or more of the various cell sorting or enrichment techniques can be used to sort out phagocytic cells (e.g., macrophages) prior to the loading measurement (above) to better define which cell population has been labeled in situ. The measured cell labeling parameter can then be used to calculate the apparent number of inflammatory cells present in tissue using the magnetic resonance methods described herein.

In order to extract accurate quantification of labeled cells and/or relative inflammation score from the $^{19}$F MRI/MRS data sets, additional calibrations and standards may be employed. For example, one can use a calibrated external $^{19}$F reference (i.e., phantom) during the actual $^{19}$F MRI/MRS scan of the subject material containing labeled cells. The image intensity of the calibrated phantom is used, tor examples, when analyzing the $^{19}$F MRI/MRS data set to prove an absolute standard for the number of $^{19}$F nuclei when examining the subject material or patient. The calibrated phantom is used to normalize the sensitivity of the particular MRI/MRS system that has been loaded with a particular subject to be imaged. The $^{19}$F reference may be, for example, one or more vessels containing a solution of a known concentration of $^{19}$F nuclei. In some embodiments, the solution contains a dilute concentration of the emulsified fluorocarbon labeling reagent. Optionally, the solution contains non-emulsified fluorocarbon labeling reagent, a gel, or liquid, for example that has been diluted in a suitable solvent. Optionally, the solution can be composed of another fluoro-chemical, ideally wish a simple $^{19}$F NMR spectrum, preferably with a single narrow NMR resonance (e.g. trifluoroacetic acid (TFA) or trifluoroacetamide (TFM) and other fluorinated acids, trifluorotoluene or trifluoroethanol). In some embodiments, the T1 and T2 values of the reference solution are similar to those of the labeling reagent. Optionally, the solution can contain perfluorocarbon-labeled cells, or lysines of the same. The non-cellular reference has the advantage of longer storage times. Optionally, the solution can take the form of a gel. The vessel containing the solution can be sealable, and can take a variety of geometries; vessel geometries including ellipsoidal, cylindrical, spherical, and parallel piped shapes. One or more vessels containing $^{19}$F reference solution can be used during the $^{19}$F MRI/MRS of the subject material if multiple $^{19}$F references (i.e., vessels) are used they can contain the same $^{19}$F concentration or different concentrations, and in the case of the latter, they ideally contain graded concentrations of fluorochemical. The placement of the calibrated $^{19}$F reference vessel(s) can in some embodiments, be placed externally or alongside, or optionally inside, the imaged subject or patient prior to data acquisition. In some embodiments, the reference is imaged using $^{19}$F MRI along with the subject in the same image field of view (FOV). Optionally, $^{19}$F MRS data is acquired in the reference either sequentially or in parallel with the subject data set. Optionally, data from the reference can be acquired using MRI/MRS acquired in a separate scan. Optionally, the external reference is not scanned along with a subject in every $^{19}$F MRI/MRS examination, but rather, values of the reference $^{19}$F signal intensity acquired using MRI/MRS is used from a scan of a comparable subject or a simulated-subject. In a given $^{19}$F MRI/MRS scan, the calibrated $^{19}$F standard may be sampled by one or more voxels. The observable $^{19}$F intensity produced by a voxel may be proportional to the concentration of the fluorochemical in the solution for gel and the voxel volume. Often in a $^{19}$F MRI scan the reference standard is comprised of many voxels. Often one calculates the mean intensity of one, several, or all voxels in the reference standard. Optionally, the mean image intensity is calculated over an ROI defined with in the $^{19}$F image of the reference standard. Optionally, the physical geometry of the reference standard vessel contributes to defining the observed $^{19}$F signal intensity, for example, the volume compartment(s) containing the $^{19}$F reference solution is smaller than the voxel volume. In other embodiments, the calibrated external reference relies on a solution with a $^{1}$H signal intensity of a known number of detectable H; in this case the sensitivity of the $^{19}$F signal in the subject material is reference to a $^{1}$H calibrated standard. Ideally the solution or gel in the $^{1}$H calibrated reference (contained in a vessel as described above) yields a simple $^{1}$H NMR spectrum, preferably with a single narrow NMR resonance (e.g., H$_2$O, or mixtures of H$_2$O-D$_2$O). Other than a different nuclei, the use of the $^{1}$H standard reference is the same in many other respects as described above for the $^{19}$F reference. Optionally, the calibrated reference standard contains any other MRI/MRS-active nuclei. In some embodiment, the reference is an internal organ or tissue detected via $^{1}$H MRI/MRS, where the data may be raw or normalized. In other embodiments, the reference is a standard that is not scanned with the subject, but is calibrated by relevant factors such as the weight of the patient or the size of the body cavity.

By computationally manipulating or combining two or more key parameters from the $^{19}$F MRI/MRS data set, one can calculate the number of labeled cells and/or relative amount of inflammation present in an ROI as described herein. For example, a fey set of parameters may include: (i) the cellular dose of labeling agent (i.e., $F_e$) measured in vitro; (ii) in vivo $^{19}$F MRI/MRS data set taken in the subject at one or more time points following labeled cell administration; (iii) the voxel volume; (iv) the in-plane voxel area (i.e., area of the image pixel); (v) optionally, the MRI/MRS data set from the $^{19}$F reference standard; (vi) optionally, the measured Johnson noise of the $^{19}$F MRI/MRS data in the subject material; (vii) optionally, the measured signal-to-noise ratio (SNR) of one or more voxels of the $^{19}$F MRI/MRS data set in the subject material; (viii) optionally, the measured SNR of one or more voxels of the $^{19}$F MRI/MRS data set from the reference standard; (ix) optionally, the $^{19}$F NMR relaxation times (T1, T2, and T2*) of the subject material; (x) optionally, the $^{19}$F NMR relaxation times (T1, T2, and T2*) of the reference standard (for example, see Magnetic Resonance Imaging, Third Edition, chapter 4, editors D. D. Stark and W. G. Bradley, Mosby, Inc., St, Louis Mo. 1999). Those skilled in the art can derive other parameters, combinations of the above set, or derivations thereof, particularly from the $^{19}$F MRI/MRS dataset, that can be used to quantify the number of labeled cells in situ. In certain embodiments the above set of key parameters can be used to derive quantitative or statistical measures of the accuracy or confidence of the measured number of labeled cells.

There are many ways to combine the key parameters, (i-x, above), any subsets of these, or any of their combinations or approximations, to estimate the effective number of labeled cells seen by $^{19}$F MRI in the subject material, denoted by N. For example, one can use an equation of the following form:

$$N_c = \frac{[F_R]v}{I_R} \frac{1}{F_c} \sum_{F_c}^{N_{ROI}} I_c^{(i)}$$

where: $N_c$=total number of labeled cells in the ROI; $[F_R]$= concentration of $^{19}$F in the calibrated $^{19}$F reference solution (or gel); v=voxel volume; $I_R$=mean intensify of the calibrated $^{19}$F reference taken with the MRI/MRS scan, averaged over one or more voxels, $F_e$=average $^{19}$F cellular dose of the labeling agent measured in vitro; $N_{ROI}$=number of voxels in the ROI containing labeled cells; $I_c^{(i)}$=image intensify of the i$^{th}$ voxel in the ROI containing labeled cells; i=unitless index for voxels in the ROI containing labeled cells. See, U.S. Patent Publication No. 2013/0343999, herein incorporated by reference in its entirety.

There are also many ways to approximate $N_c$ from the $^{19}$F data set. For example, one could use the following expression.

$$N_c \approx \frac{I_c^{avg}}{I_R} [F_R] v \frac{1}{F_c} N_{ROI}$$

where $I_c^{avg}$ is the average intensity of the ROI containing the labeled cells, (i.e. the average intensity of the $N_{ROI}$ voxels).

As another example, one could use the following expression.

$$N_c \approx \frac{I_c^{avg}}{I_R} V_c \frac{1}{F_c} [F_R]$$

where $V_e$ is the total volume of the ROI containing the labeled cells.

As a further example, one could use the following expression.

$$N_c \approx \frac{I_c^{avg}}{I_R} \frac{V_c}{V_{r_c}} \frac{1}{F_c} N_R$$

where $V_R$ is the effective volume of the reference in the $^{19}$F MRI/MRS and $N_R$ is the number $^{19}$F nuclei in $V_R$. Note that in all of the above formulas the various intensities (i.e., $I_R$, $I_c^{avg}$, $I_c^{(i)}$) can be normalized to the image noise, and thus the above formulas can be equivalently expressed in terms of the appropriate SNR values for the particular regions. Thus, there are many ways to estimate the number of labeled cells, $N_c$, and many similar forms of these basic expressions can be derived by basic mathematical manipulations, however, all rely on the same basic content contained within the input parameters described by (i-x). Furthermore, quantification of labeled cells in an ROI need not be expressed in terms of absolute numbers or effective cell numbers. Other quantitative indices can be derived that are indicative of the amount of cells in an ROI. For example, one can calculate the ratio $I_c^{avg}/I_R$, or the ratio of the average SNR values observed in the ROI and the reference; all of these fall within subsets of the above expressions and/or the parameters. See, U.S. Patent Publication No. 2013/0343999, herein incorporated by reference in its entirety.

It is noted that the above analysis of cell numbers and related indices assume that the $^{19}$F NMR relaxation times (i.e., particularly T1 and/or T2) of the fluorocarbon label is approximately the same as material in the calibrated $^{19}$F reference standard. In the case that the relaxation times are not comparable, one of skill in the art can readily correct for this by employing the known MRI intensity equations of the particular imaging protocol being used, expressed in terms of T1 and T2.

Optionally, the $^{19}$F MRI data set of the subject material can undergo post-processing before the actual cell quantification calculation is performed (as described above). For example, post-processing algorithms may include "de-noising" the $^{19}$F data set. This can be accomplished by, for example, by thresholding the image to cut off low-intensity noise; this involves rescaling the image intensity so that low values are set to zero. In magnitude MRI images, random Johnson noise is often apparent and uniformly distributed across the image FOV. It is well known in the art that one can threshold out the low-level image intensity so that regions known to contain no true signal (i.e. devoid of $^{19}$F and/or $^1$H nuclei) appear to have a null or very near-null intensity. This process can be performed in an ad-hoc fashion (i.e., "manually" or by visual inspection), or by using a computer algorithm. In other embodiments, de-noising of the data set can be achieved by using other algorithms, for example using wavelet analysis, and many methods are known in the art for image de-noising.

The following references are incorporated in their entirety herein: Khare, A., et al., INTERNATIONAL JOURNAL OF WAVELETS MULTIRESOLUTION AND INFORMATION PROCESSING, 3 (4): 477-46 December 2005; Cruz-Enriquez, H., et al., IMAGE ANALYSIS AND RECOGNITION, 3656: 247-254 2005; Awate, S P., et al., INFORMATION PROCESSING IN MEDICAL IMAGING PROCEEDINGS, 3565: 677-688 7005; Ganesan. R.; et al., IIE TRANSACTIONS, 36 (9): 787-86 September 2004; Seheunders, P., IEEE TRANSACTIONS ON IMAGE PROCESSING, 13 (4): 475-485 April 2004; Ghugre, N R., MAGNETIC RESONANCE IMAGING, 21 (8): 913-921 October 2003; Bao, P., et al., IEEE TRANSACTIONS ON MEDICAL IMAGING, 22 (9):1089-199 September 2003; Wu, Z Q., et al., ELECTRONICS LETTERS, 39 (7): 603-605 Apr. 3, 2003; LaConte, S M., et al., MAGNETIC RESONANCE IN MEDICINE, 44 (5): 746-757 November 2000: Laine, A F., ANNUAL REVIEW OF BIOMEDICAL ENGINEERING, 2: 511-550 2000; Zuroubi, S., et al., MAGNETIC RESONANCE IMAGING, 18 (1): 59-68 January 2000: Nowak, R D., IEEE TRANSACTIONS ON IMAGE PROCESSING, 8 (10):1408-1419 October 1999; and Healy, D M., et al., ANNALS OF BIOMEDICAL ENGINEERING, 23 (5): 637-665 SEPTEMBER-OCTOBER 1995.

Other types of post-processing algorithms are known in the art that can be applied to the $^{19}$F MRI data set before or after quantification, such as zero-filing (A Handbook of Nuclear Magnetic Resonance, 2nd Edition, Ray Freeman, Addison Wesley Longman Press 1997) and various image interpolation, de-noising, and image smoothing algorithms (for example, see The Image Processing Handbook, 3rd Edition, John C. Russ, CRC Press/IEEE Press).

In certain embodiments the above set of key parameters (i-x) can be used to derive quantitative or statistical measures of the accuracy or confidence of the measured number of labeled cells or related indices. $^{19}$F MRI/MRS data sets are often subject to SNR limitations within ROI, and thus if is often useful to calculate a metric of the confidence or accuracy of the measurement. Many methods are known in the art for the statistical analysis of MRI and other biomedical-type ii-nags. The claimed embodiment is understood to encompass these known methods.

Additional descriptions of useful MRI techniques and the like can be found, for example, in U.S. Pat. No. 9,352,057, the contents are herein incorporated by reference in its entirety.

Pharmaceutical Formulations and Uses

Methods of administration of the emulsions of the application are well-known to those of skill in the art. To achieve the desired activity, the emulsions can be administered in a variety of unit dosage forms. The dose will vary according to the particular emulsion. The dose will also vary depending on the manner of administration, the overall health, condition, size, and age of the patient.

In certain embodiments, administration of the emulsions may be performed by an intravascular route, e.g., via intravenous infusion by injection. In certain embodiments, other routes of administration may be used. Formulations suitable for injection are found in Remington's Pharmaceutical Sciences, Mack Publishing Company, Philadelphia, Pa., 17th ed. (1983). Such formulations must be sterile and non-pyrogenic, and generally will include a pharmaceutically effective carrier, such as saline, buffered (e.g., phosphate buffered) saline, Hank's solution, Ringer's solution, dextrose/saline, glucose solutions, and the like. The formulations may contain pharmaceutically acceptable auxiliary substances as required, such as, tonicity adjusting agents, wetting agents, bactericidal agents, preservatives, stabilizers, and the like. In certain embodiments suitable buffers for intravenous administration are used to aid in emulsion stability. In certain embodiments glycols are used to aid in emulsion stability.

In certain embodiments, administration of the emulsions may be performed by a parenteral route, typically via injection such as intra-articular or intravascular injection (e.g., intravenous infusion) or intramuscular injection. Other routes of administration, e.g., oral (p.o.), may be used if desired and practicable for the particular emulsion to be administered.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the pharmaceutical compositions of the application.

In certain embodiments, formulations of the subject emulsions are pyrogen-free formulations which are substantially free of endotoxins and/or related pyrogenic substances. Endotoxins include toxins that are confined inside microorganisms and are released when the microorganisms are broken down or die. Pyrogenic substances also include fever-inducing, thermostable substances (glycoproteins) from the outer membrane of bacteria and other microorganisms. Both of these substances can cause fever, hypotension and shock if administered to humans. Due to the potential harmful effects, it is advantageous to remove even low amounts of endotoxins from intravenously administered pharmaceutical drug solutions. The Food & Drug Administration ("FDA") has set an upper limit of 5 endotoxin units (EU) per dose per kilogram body weight in a single one hour period for intravenous drug applications (The United States Pharmacopeial Convention, Pharmacopeial Forum 26 (1): 223 (2000)).

Formulations of the subject emulsions include those suitable for oral, dietary, topical, parenteral (e.g., intravenous, intraarterial, intramuscular, subcutaneous injection), ophthalmologic (e.g., topical or intraocular), inhalation (e.g., intrabronchial, intranasal or oral inhalation, intranasal drops), rectal, and/or intravaginal administration. Other suitable methods of administration can also include rechargeable or biodegradable devices and controlled release polymeric devices. Stents, in particular, may be coated with a controlled release polymer mixed with an agent of the application. The pharmaceutical compositions of this disclosure can also be administered as part of a combinatorial therapy with other agents (either in the same formulation or in a separate formulation).

The amount of the formulation which will be therapeutically effective can be determined by standard clinical techniques. In addition, in vitro assays may optionally be employed to help identify optimal dosage ranges. The precise dose to be employed in the formulation will also depend on the route of administration. Effective doses may be extrapolated from dose-response curves derived from in vitro or animal model test systems. The dosage of the compositions to be administered can be determined by the skilled artisan without undue experimentation in conjunction with standard dose-response studies. Relevant circumstances to be considered in making those determinations include the condition or conditions to be treated, the choice of composition to be administered, the age, weight, and response of the individual patient, and the severity of the patient's symptoms. For example, the actual patient body weight may be used to calculate the dose of the formulations in milliliters (mL) to be administered. There may be no downward adjustment to "ideal" weight. In such a situation, an appropriate dose may be calculated by the following formula: Dose (mL)=[patient weight (kg)×dose level (mg/kg)/drug concentration (mg/mL)]

Therapeutics of the disclosure can be administered in a variety of unit dosage forms and their dosages will vary with the size, potency, and in vivo half-life of the particular therapeutic being administered.

For in situ applications, emulsions may be formulated to have optimal pharmacokinetic properties to enable uptake by phagocytes before clearance of the emulsion.

Doses of therapeutics of the disclosure will also vary depending on the manner of administration, the particular use of the emulsion, the overall health, condition, size, and age of the patient, and the judgment of the prescribing physician.

The formulations of the application can be distributed as articles of manufacture comprising packaging material and a pharmaceutical agent which comprises the emulsion and a pharmaceutically acceptable carrier as appropriate to the mode of administration. The pharmaceutical formulations and uses of the disclosure may be combined with any known compositions for the applications of the application.

Diagnostic Detection Methods

Exemplary applications of the present invention include the diagnostic detection of cells, e.g., immune cells that accumulate at tissue sites as part of an inflammatory response and cells that are grafted into the body in order to treat a disease or condition, i.e., cytotherapy. Cytotherapy can generally include the administration of cells to a subject in need thereof. In some cases, the imaging method described herein is used to diagnose a disease or to determine a prognosis. Cells can be endogenous cells in the body, for example, various immune cells (T cells, B cells, macrophages, NK cells, DCs, etc.), stem cells, progenitor cells, cancer cells, as well as engineered cells, which are often used in cytotherapy in its various forms. An engineered cell can express a heterologous nucleic acid or a recombinant protein.

Non-invasive imaging of cells, e.g., immune cells in the body is useful because it can aid in the diagnosis and monitoring of disease, e.g., inflammation. In the field of cytotherapy, the ability to image the cell graft provides valuable feedback about the persistence of the graft, potential cell migration, and improves safety surveillance. Many experimental cell therapies that are in clinical trials, e.g., stem cells and immunotherapeutic cells, could benefit from the use of this technology.

Computer Methods

Methods for quantifying labeled cells will typically be conducted with the aid of a computer, which may operate software designed for the purpose of such quantification. Such software may be a stand-alone program or it may be incorporated into other software, such as MRI image processing software. See, for example, U.S. Patent Publication No. 2007/0253910, herein incorporated by reference in its entirety.

The disclosure will be more readily understood by reference to the following examples, which are included merely for purposes of illustration, of certain aspects and embodiments of the present application, and are not intended to limit the disclosure.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

EXAMPLES

Example 1: Paramagnetic Fluorinated Nanoemulsions for Sensitive Cellular Fluorine-19 Magnetic Resonance Imaging The reference Kislukhin et al., Nat. Mater., 2016 June, 15(6): 662-668 is herein incorporated by reference in its entirety for all purposes.

Abstract

Fluorine-19 magnetic resonance imaging ($^{19}F$ MRI) probes enable quantitative in vivo detection of cell therapies and inflammatory cells. Here, we describe the formulation of perfluorocarbon-based nanoemulsions with improved sensitivity for cellular MRI. Reduction of the $^{19}F$ spin-lattice relaxation time ($T_1$) enables rapid imaging and an improved signal-to-noise ratio, thereby improving cell detection sensitivity. We synthesized metal-binding β-diketones conjugated to linear perfluoropolyether (PFPE), formulated these fluorinated ligands as aqueous nanoemulsions, and then metalated them with various transition and lanthanide ions in the fluorous phase. Iron(III) tris-β-diketonate (also referred to as "FETRIS") nanoemulsions with PFPE have low cytotoxicity (<20%) and superior MRI properties.

Moreover, the $^{19}F$ $T_1$ can readily be reduced by an order of magnitude and tuned by stoichiometric modulation of the iron concentration. The resulting $^{19}F$ MRI detection sensitivity is enhanced by 3-to-5 fold over previously used tracers at 11.7 T, and is predicted to increase by at least 8-fold at clinical field strength of 3 T.

Magnetic resonance imaging (MRI) is becoming a clinical tool for visualizing specific cell populations in the body[1]. MRI cell detection using exogenous agents can be used to visualize the in vivo trafficking and behavior of immune or stem cells used to treat a host of diseases. Fluorine-19 ($^{19}F$) "tracer" agents are an emerging approach to intracellularly label cells of interest, either ex vivo or in situ, to enable cell detection via $^{19}F$ MRI[1, 2]. The $^{19}F$ label yields positive-signal 'hot-spot' images, with no background signal due to negligible fluorine concentration in tissues. Images can be quantified to measure apparent cell numbers at sites of accumulation[2, 3], thereby enabling "in vivo cytometry"[4]. Tracer agent compositions have mostly focused on nontoxic perfluorocarbons (PFC). Clinical translation of $^{19}F$ cell detection has recently been realized in patients[5] using PFC nanoemulsion to label a dendritic cell cancer vaccine. In these experiments, the cell detection limit was conservatively estimated to be of order $10^5$ cells per voxel[5].

Improving the sensitivity of $^{19}F$ cell detection could lower the barriers for using this technology in a wider range of biomedical applications. One approach for boosting sensitivity is by decreasing the intrinsically-high $^{19}F$ spin-lattice relaxation time ($T_1$) of PFC molecules[6-8]. The $T_1$ ultimately limits the rate of $^{19}F$ MRI data acquisitions. Often, $^{19}F$ images require summation of multiple acquisitions (i.e., signal averaging) to generate a sufficient signal-to-noise ratio (SNR) for confident interpretation. High $^{19}F$ $T_1$ values require a long repetition time (TR) to allow for longitudinal signal recovery, thus limiting the number of signal acquisitions attainable during a fixed total imaging time ($t_i$). As $t_i$ is constrained when scanning patients, the key parameter to maximize is $SNR/t_i$. Shortening $T_1$ can increase $SNR/t_i$, sensitivity, and decrease the minimum number of detectable cells per voxel. In practice, reducing $T_1$ by molecular design can also lead to a reduction in the spin-spin relaxation time ($T_2$) and line broadening of the resonance; this effect may degrade the SNR if $T_2$ becomes comparable to the data acquisition sampling time along the frequency encoding direction[9]. The creation of stable and cytocompatible $^{19}F$ agents with 'ultra-fast' $T_1$ is an open challenge that can greatly impact the MRI field, enabling accelerated MRI acquisitions and the detection of sparser cell populations in vivo.

The relaxation times $T_1$ and $T_2$ can be profoundly altered by high-spin paramagnetic metal ions (e.g., $Mn^{2+}$, $Fe^{3+}$, $Gd^{3+}$). Prior studies[6] have attached $Gd^{3+}$ to the outer surface of the PFC nanoemulsion droplet resulting in modest reductions in $T_1$. With increasing distance (r), the steep fall-off ($\sim r^{-6}$) of paramagnetic relaxation rate enhancement from paramagnetic centers limit the efficacy of relaxation agents bound to the surface of PFC nanoparticles.[8, 10] Thus, effective relaxation enhancement necessitates introduction of metal ions into the fluorous phase, i.e., within the nanoemulsion droplets, to achieve a short $T_1$ using a minimum amount of a paramagnetic additive.

Described herein are the scalable synthesis and properties of a family of paramagnetic PFC nanoemulsions with excellent $^{19}F$ MRI and biological properties. It is shown that fluorinated materials incorporating suitable ligands can tightly bind and retain sufficient amounts of metal ions in the fluorous phase of the nanoemulsion to yield $^{19}F$ agents with greatly enhanced sensitivity. These novel nanoemulsion materials contain metal-binding 3-diketones conjugated to linear perfluoropolyether (PFPE).

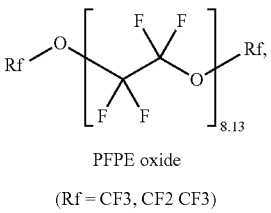

PFPE oxide (Rf = CF3, CF2 CF3)

wherein Rf is $CF_3$ and $CF_2CF3$ in a ratio of 2:1, based on $^{19}F$ NMR analysis.

Using these agents, assessments of the biocompatibility, cell labeling stability, and in vivo MRI studies in mice are described. Sensitivity enhancement of these materials will potentially accelerate the use of $^{19}F$ cell detection in a host of clinical cell therapy trials and for diagnostic inflammation imaging.

Modeling of Paramagnetic Relaxation Enhancement

In the initial design of $^{19}F$ probes, magnetic resonance relaxation time modeling of the impact of dissolving metals ions into PFC were conducted. Solomon-Bloembergen-Morgan (SBM) theory[11, 12] describes paramagnetic relaxation enhancement (PRE) of $R_1=1/T_1$ and $R_2=1/T_2$ of surrounding media at a given magnetic field strength, molecular mobility, and metal concentration (See Supporting Information, Kislukhin et al., Nat. Mater., 2016 June, 15(6): 662-668). Using SBM theory, we found optimal parameters for enhancement of $R_1$ while minimizing linewidth broadening, i.e., $R_2$. The modeling results (FIG. 9) show that $Fe^{3+}$ uniformly dispersed in PFC will provide the most robust enhancement of $^{19}F$ $R_1$. $Mn^{2+}$ and $Gd^{3+}$ are likely to cause severe line broadening due to a large increase in $R_2$, especially at high magnetic field strengths. This line broadening originates from very slow electronic relaxation in $Mn^{2+}$ and $Gd^{3+}$ (FIG. 9).

Design and Preparation of Metal-Binding Perfluorocarbons

Design of a cytocompatible fluorous-soluble metal chelate requires careful consideration. The steep fall-off of PRE with increasing distance ($\sim r^{-6}$) necessitates solubilisation of individual metal ions, as opposed to incorporating metal-bearing oligomeric clusters or nanoparticles. The metal must not efflux from the fluorous phase during cell labelling and after in vivo administration. The high electronegativity of fluorine imparts very low cohesive energy density[13] and Lewis basicity[14] to heavily fluorinated compounds, making them extremely poor solvents and ligands. The choice of ligands compatible with fluorous phase is therefore limited to the most hydrophobic scaffolds, with as few intermolecular interactions as possible. To maximize solubility in the fluorous phase, the resulting metal complex should be uncharged and coordinatively saturated. These criteria can be satisfied by using bidentate, monoionic ligands (L) that form high-spin, charge-neutral tris-complexes with trivalent metals ($FeL_3$, $GdL_3$) and bis-complexes with divalent metals ($MnL_2$). Of these, only $FeL_3$ are coordinatively saturated, due to the small size of the parent $Fe^{3+}$ ion. Coordinatively unsaturated complexes of larger $Mn^{2+}$ and $Gd^{3+}$ tend to be unstable with respect to the formation of oligomeric[15], charged, or ternary complexes[16] (e.g., $[GdL_3]_n$, $[GdL_4]^-$, $[GdL_3.(H_2O)_x]$). Although gadolinium chelates are widely used contrast agents in clinical $^1H$ MRI because $Gd^{3+}$ has the highest magnetic moment, we predict that $Fe^{3+}$ was predicted to be better suited for $^{19}F$ applications.

Figure 9:
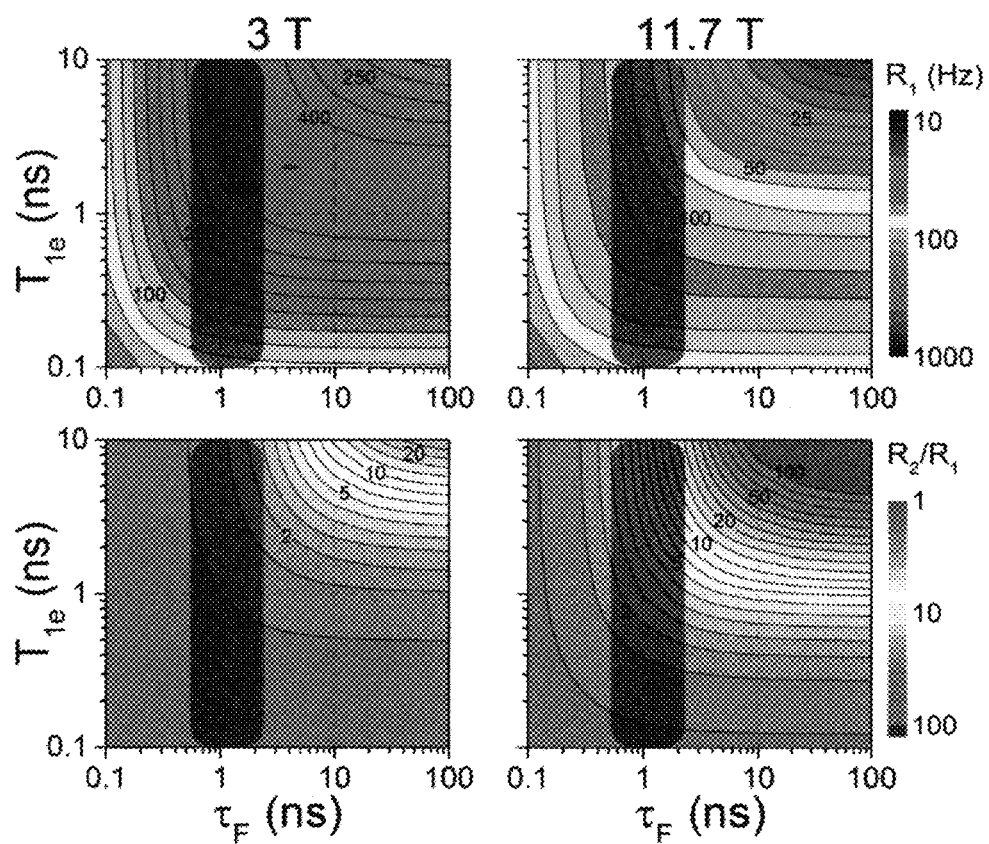
FIG. 9. Theoretical modeling of $^{19}F$ relaxation rates. Shown are estimates of $^{19}F$ $R_1$ (top) and minimum values of $R_2/R_1$ (bottom). Relaxation rates were calculated with SBM equations S1-S4, plotted as a function of $T_{1e}$ and $\tau_F$ at S=5/2, r=1 nm, at 310 K and at field strengths of 3 T (left) and 11.7 T (right). The dark shaded areas indicate the approximate range of likely $\tau_F$ values encountered experimentally. The $T_{1e}$ and $\tau_F$ values that provide the strongest PRE without excessive signal broadening are found on hyperbolae near the centers of each panel.
Figure 10:
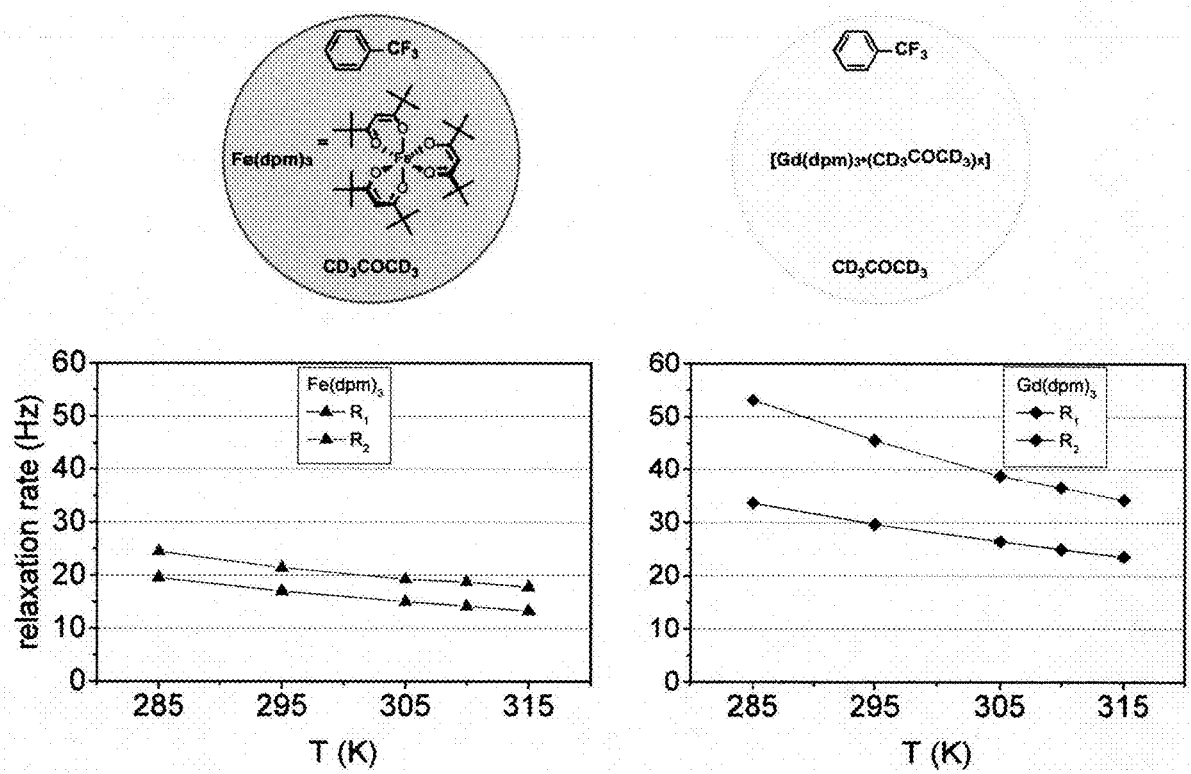
FIG. 10. $^{19}F$ relaxometry of organic solutions containing paramagnetic complexes. Relaxation rates of the $CF_3$ group were measured in the presence of 50 mM tris-(dipivaloylmethanato) complexes Fe(dpm)₃ (left) and Gd(dpm)₃ (right) in 1:1 v/v PhCF₃:acetone-d₆ at 9.4 T in a sealed 5 mm NMR tubes. Measurement and fitting errors did not exceed 1% for $R_1$ and 2% for $R_2$. Solid lines are guide for the eye. While monomeric Fe(dpm)₃ was highly soluble in PhCF₃ alone, polymeric Gd(dpm)₃ dissolved only in the presence of Lewis basic solvent acetone-d₆. Both relaxation agents displayed decreasing relaxation rates $R_1$ and $R_2$ upon increase in temperature (decrease in $\tau_F$), as expected from solutions in the "fast motion" regime ($1/\tau_F \approx \gamma_F B_0$) and in contrast to PFC emulsions described here ($1/\tau_F \approx \gamma_F B_0$). In the fast motion regime, electronic relaxation rates do not have an effect on nuclear relaxation rates. The observed ratio between $R_1$(Gd) and $R_1$(Fe) was 1.72-1.77, consistent with the expected 1.8-fold difference due to the S(S+1) term in Eq. S, curtailed by a slight increase in the distance of minimal approach due to the larger size of Gd.
Figure 11:
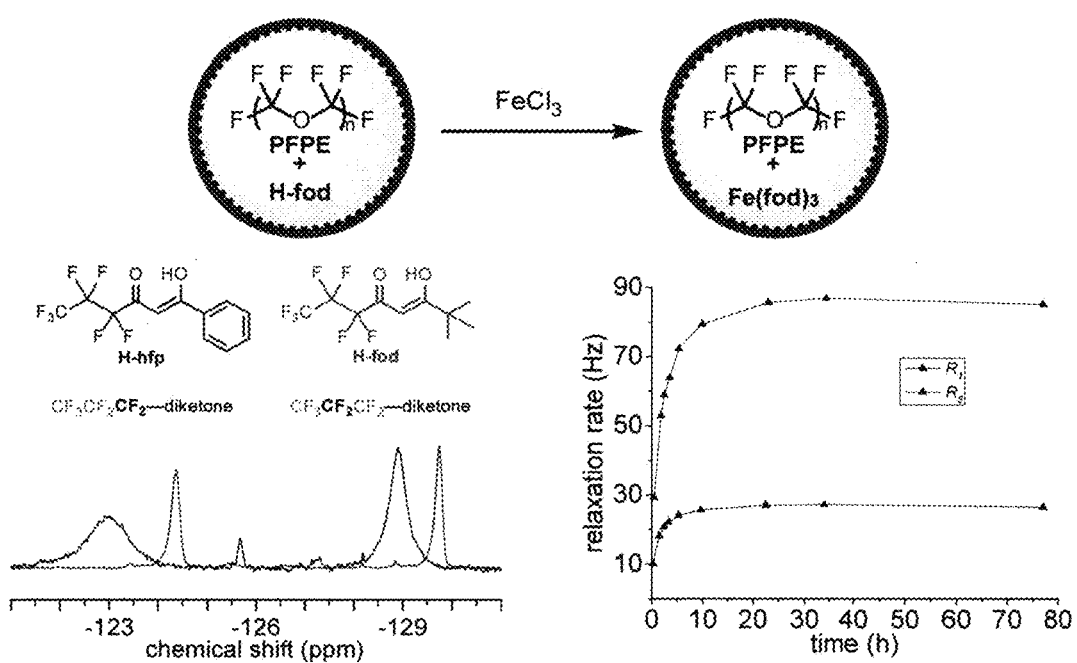
FIG. 11. $^{19}$F relaxometry of PFPE with metalated small diketones. PFPE nanoemulsion was doped in the fluorous phase with small fluorinated diketones H-fod and H-hfp. Diketones (7.8 mM) were dissolved in aqueous PFPE nanoemulsion (60 g/L, 50% D$_2$O), followed by addition of FeCl$_3$ (1.3 mM). $^{19}$F NMR spectroscopy (9.4 T, 295 K) revealed inefficient incorporation of Fe$^{3+}$ into the fluorous phase. The left panels display broad $^{19}$F NMR signals of CF$_2$ groups of H-fod and H-hfp observed in the absence of metals indicating poor solubility of the ligands in the fluorous phase. Aromatic H-hfp shows broader signals than aliphatic H-fod, suggesting a greater extent of aggregation due to plausible π-stacking. The right panel show the time course of metalation of PFPE+H-fod nanoemulsion measured by $^{19}$F relaxometry. $R_1$ and $R_2$ were measured for main PFPE peak at −91 ppm at different time points. The solid lines are guides for the eye. The appearance of orange color of Fe(fod)$_3$ correlated with an increase in relaxation rates. Metalation of PFPE emulsions doped with H-fod with Fe$^{3+}$ was several orders of magnitude slower than metalation of emulsions containing pAn-FDK (FIG. 15).

Initially, the results of the PRE modeling [Example 2 and FIG. 9] using small molecules were tested. Fluorinated β-diketone H-fod (FIG. 1) was chosen as starting point. Addition of 2.8 mM H-fod to the aqueous phase of a premade PFPE nanoemulsion displays apparent dissolution of the diketone and appearance of heptafluoropropyl groups in $^{19}F$ NMR spectra featuring three broad singlets. Addition of 0.7 mM $FeCl_3$ led to the slow formation of orange-colored $Fe(fod)_3$ and a commensurate increase in $R_1$ from 2.3 to 27.0 $s^{-1}$ and in $R_2$ from 4.0 to 85.6 $s^{-1}$ (at 9.4 T) of the major PFPE resonance (−91.4 ppm) by 24 hours (FIG. 11). With $GdCl_3$, lower $R_1$ (12.8 $s^{-1}$) and higher $R_2$ (285 $s^{-1}$) values were obtained. The corresponding gadolinium complex displayed modest $R_1$ values accompanied by strong line broadening, a likely consequence of both high electronic relaxation time ($T_{1e}$) of $Gd^{3+}$ and high rotational correlation time ($\tau_F$) of the oligomeric gadolinium chelate (see Eqs. S1-S4 and FIGS. 9 and 10). However, broad NMR signals of the ligand in the absence of metals and slow metalation kinetics suggested insufficient solubility of H-fod in PFPE.

Figure 2:
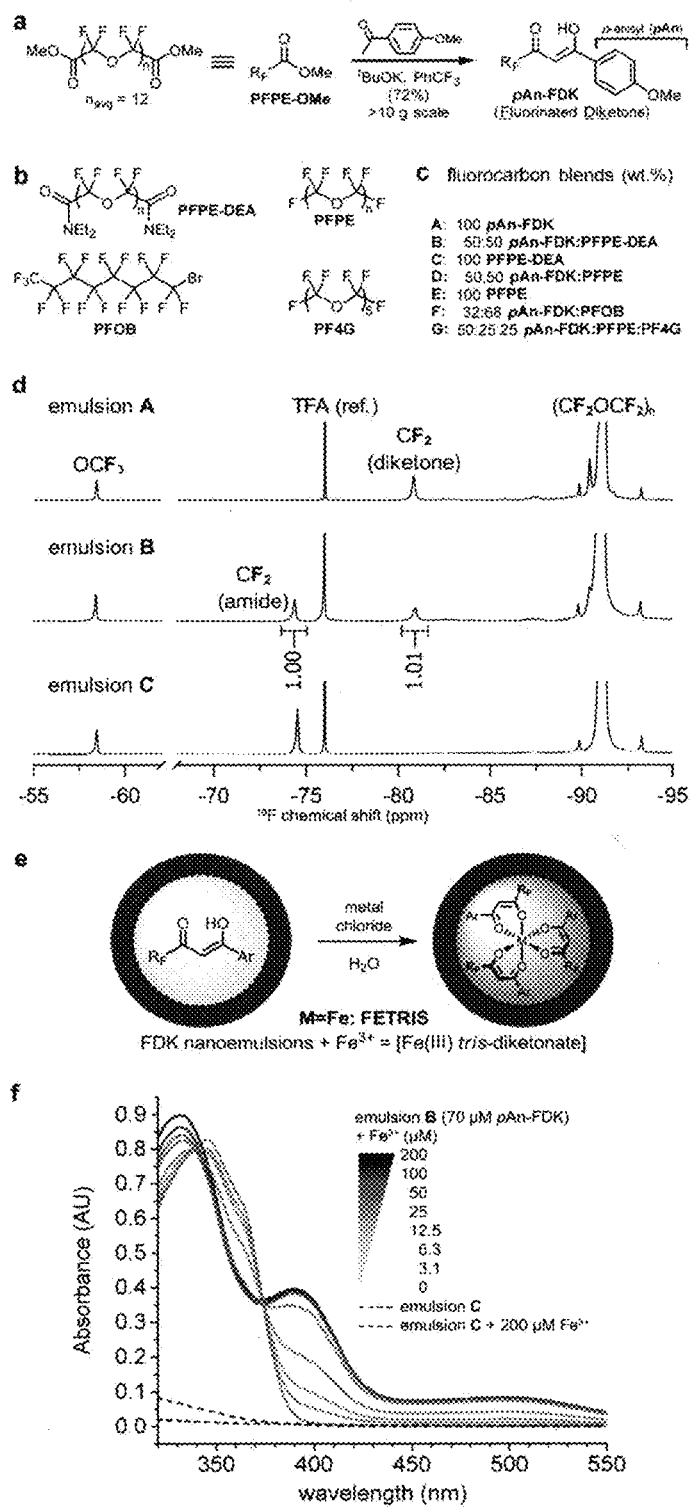
FIGS. 2A-2F. Preparation and characterization of metal-binding nanoemulsions for $^{19}F$ MRI.
Figure 12:
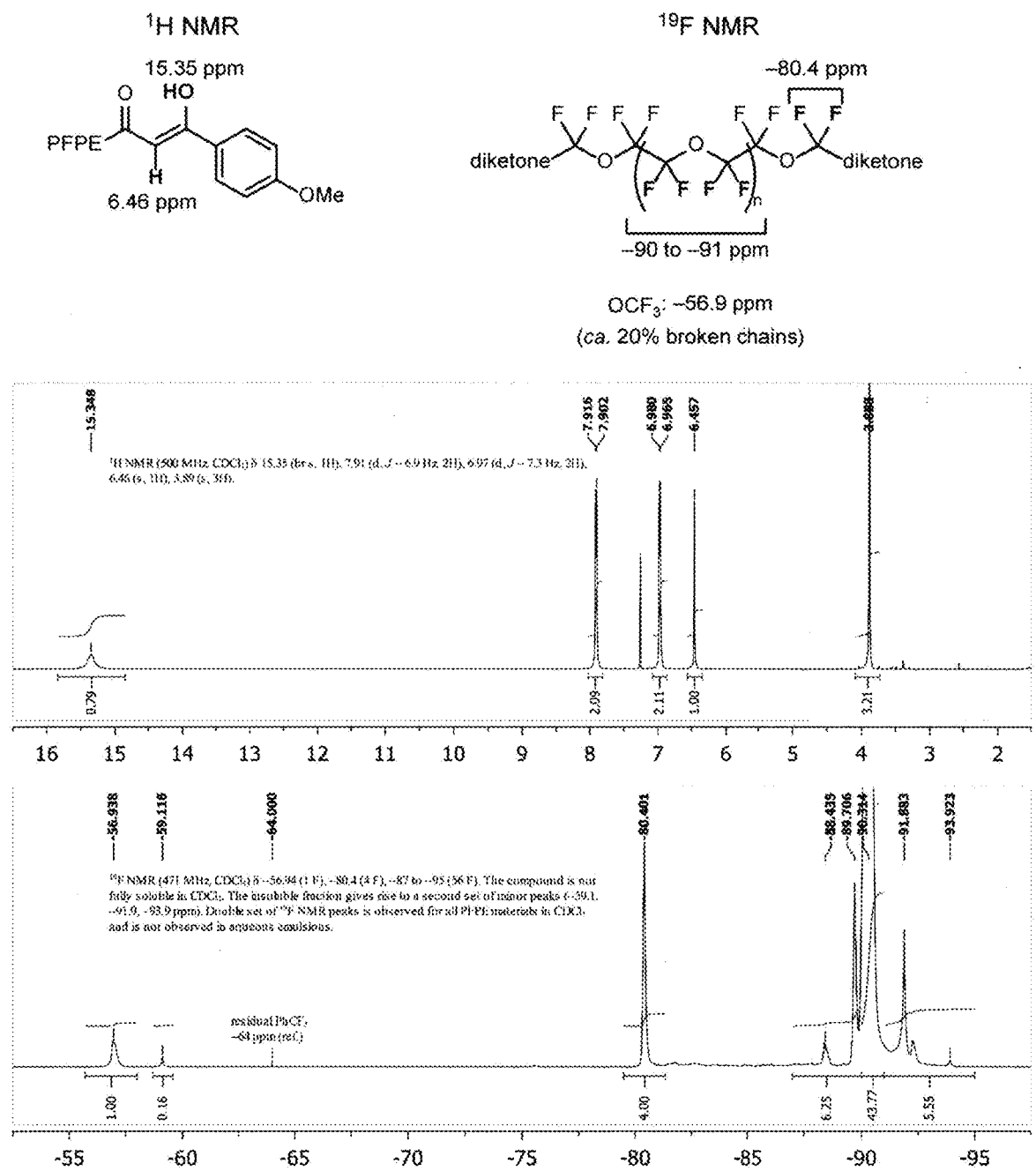
FIG. 12. NMR characterization of pAn-FDK oil. Shown are the structure of pAn-FDK (top) and the key NMR resonances of $^1$H (middle) and $^{19}$F (bottom) used to prepare emulsions A, B, D, F, and G. Data were acquired at 11.7 T.

To improve solubility, fluorinated β-diketones (FDK) that have a greater fluorine content were investigated. The PFPE-based ligand pAn-FDK using Claisen condensation[17] between PFPE-OMe and excess p-methoxyacetophenone, yielding highly pure pAn-FDK product at >10 g scale upon simple extractive workup was prepared (FIG. 2A). $^1H$ NMR analysis revealed new peaks at 6.46 and 15.35 ppm, characteristic of a diketone in enol form (FIG. 12). This ligand was used for subsequent studies.

Figure 13:
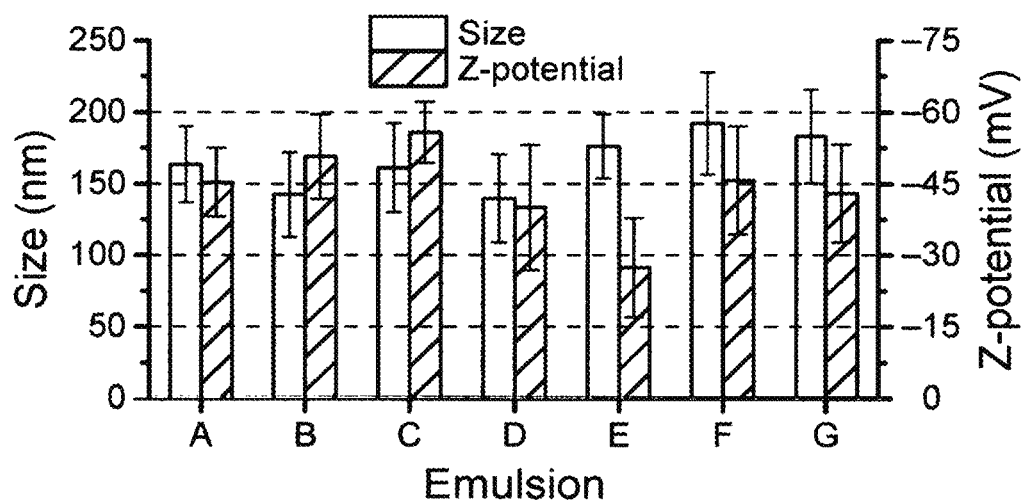
FIG. 13. Dynamic light scattering (DLS) characterization of nanoemulsions A-G. Full size of error bars reflects polydispersity index width.

To evaluate $^{19}F$ MRI properties, we blended pAn-FDK with a variety of perfluorocarbon derivatives and formulated these blended oils into aqueous nanoemulsions using microfluidization. Nanoemulsions (FIG. 2C) included pAn-FDK alone (emulsion A), or as a blend with PFPE diethylamide (DEA) (B), PFPE (D), perfluorooctyl bromide (PFOB) (F), or a short PFPE oligomer perfluorotetraglyme (PF4G) (G). Emulsions C (pure PFPE-DEA) and E (pure PFPE) are controls that cannot bind metals (FIG. 2C). PFOB was tested because of its rapid clearance from the body and prior use clinically, but is not widely used for MRI cell detection due to its multiple $^{19}F$ resonances that diminish image quality[18]. In all formulations A-G, stable nanoemulsions were formed, with similar physical characteristics. Dynamic light scattering (DLS) measurements in A-G displayed monodisperse nanoemulsions with a polydispersity index (PDI) of <0.2 and average droplet diameters ranging from 140-200 nm and negative ζ-potentials of −27 to −56 mV (FIG. 13). No change in DLS measurements were noted for up to 8 months of storage at 4° C. Nanoemulsion composition was confirmed by $^{19}F$ NMR (FIG. 2D). Terminal $CF_2$ atoms of PFPE derivatives have resonances between −70 and −85 ppm. Presence of only one major peak in this spectral range in single-component emulsions A and C confirmed high purities of the starting oils; emulsion B shows peaks from both components in the expected 1:1 ratio. Core $CF_2CF_2O$ units resonating at −91 ppm comprise ~90% of the total $^{19}F$ spectral weight and is typically the only signal detectable by $^{19}F$ MRI, which generally has a much lower SNR compared to conventional $^1H$ images.

Properties of Metalated Nanoemulsions

Figure 14:
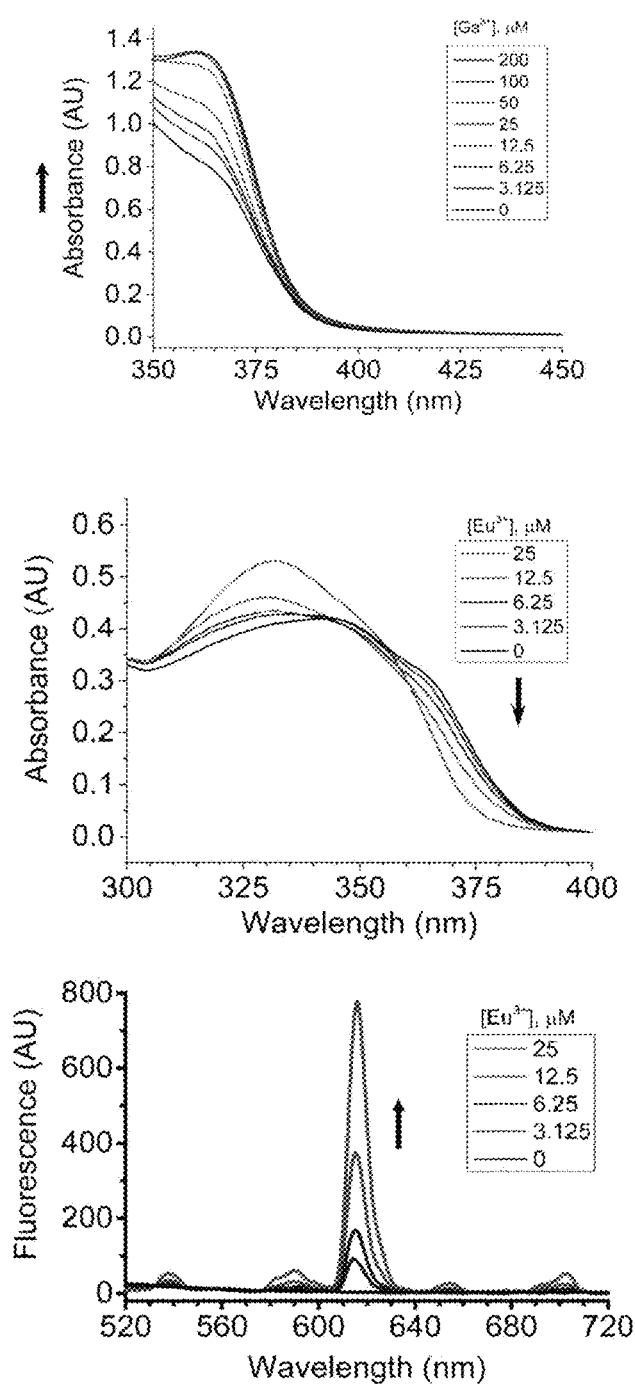
FIG. 14. Optical changes upon binding Ga$^{3+}$ and Eu$^{3+}$. The optical changes were observed upon metalation of emulsion B (70 μM pAn-FDK) with Ga$^{3+}$ (top, at pH 2.1, 8 mM HCl) and Eu$^{3+}$ (middle, at pH 7.4, 50 mM HEPES, excitation at 365 nm). Absorbance (middle) and fluorescence (bottom, $\lambda_{exec}$=365 nm) in the presence of varying concentrations of Eu$^{3+}$ in 50 mM HEPES and at pH 7.4. The arrows indicate direction of changes in optical properties upon increasing [M$^{3+}$]. No Eu$^{3+}$ fluorescence is observed with emulsion C.
Figure 15:
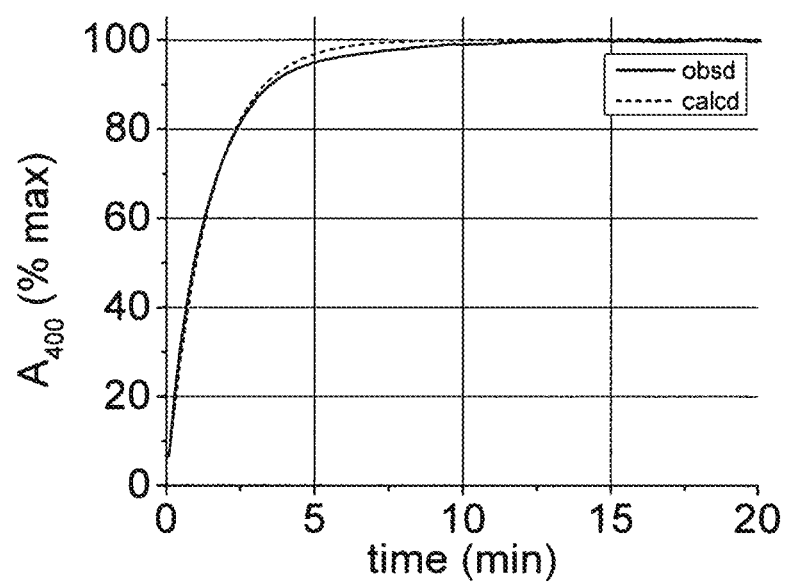
FIG. 15. Time course of metalation of FETRIS nanoemulsion with Fe$^{3+}$. Shown is the metalation of emulsion B (70 μM pAn-FDK and 10 μM Fe$^{3+}$, 8 mM HCl, pH 2.1). A single exponential fit yields $k_{obs}$=0.69±0.10 min$^{-1}$ FIG. 16. Variable temperature relaxometry of FETRIS nanoemulsion. Shown is the temperature dependence of relaxation rates $R_1$ and $R_2$ in FETRIS nanoemulsion (9.7 g/L $^{19}$F, 12.1 mM diketone, 2.4 mM Fe$^{3+}$) at 9.4 T.
Figure 19:
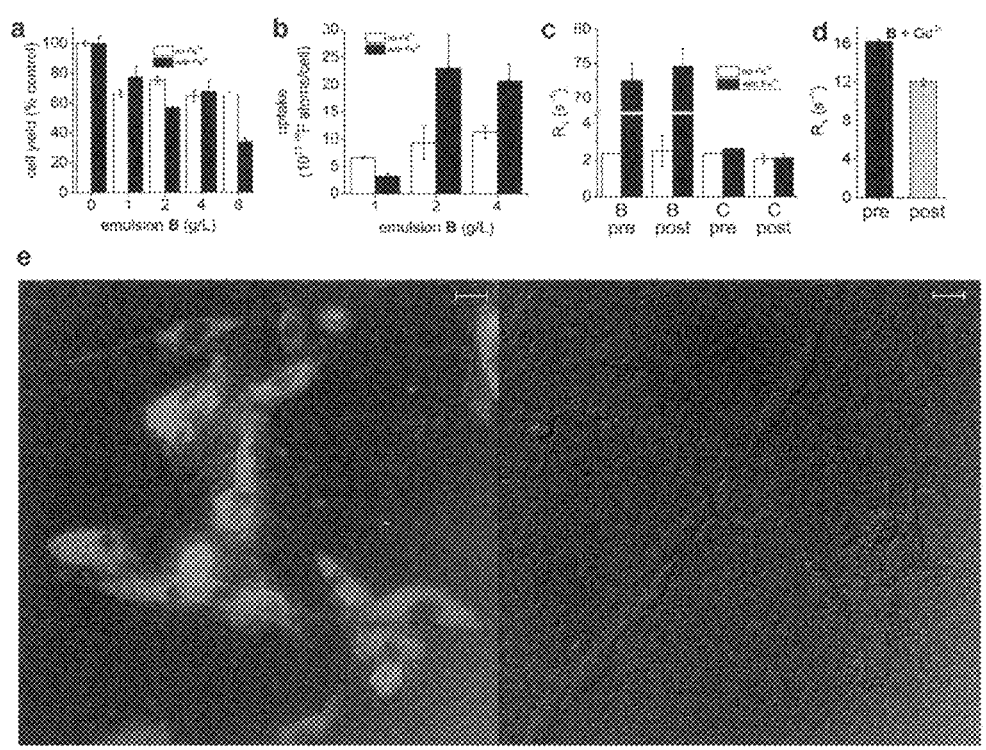
FIGS. 19A-19E. Labeling of 9L cells with FETRIS nanoemulsion. Cells were labeled as described in the Methods section, in the absence of protamine sulfate. Error bars represent standard deviations from three independent experiments.

The Pluronic surfactant used in the nanoemulsion formulation is permeable to ions enabling direct metalation of FDK nanoemulsions by the addition of metal chloride into the aqueous phase (FIG. 2E). Optical changes due to the formation of metal complexes were readily observed (FIGS. 2F and 14). Among these, europium chelates are notable for their bright photoluminescence which may be useful for studying intracellular localization and trafficking of the PFC droplets (FIG. 19E). Importantly, addition of $FeCl_3$ caused rapid ($k_{obs}$=0.69±0.10 $min^{-1}$) appearance (FIG. 15) of characteristic charge transfer bands of ferric diketonates[19] ($\varepsilon_{390}$=23, $\varepsilon_{500}$=4.9 $mM^{-1}cm^{-1}$) that linearly increased in intensity with increasing [$Fe^{3+}$] until the Fe:FDK ratio of ca. 1:3 was reached, consistent with ferric tris-diketonate (FIG. 2F). Henceforth, the term 'FETRIS' (FErric TRIS-diketonate) refers to pAn-FDK blended with PFPE and metalated with $Fe^{3+}$.

Relaxometric evaluation of nanoemulsions in the presence of different metals (FIG. 3A) revealed that binding of $Fe^{3+}$ resulted in modest line broadening of all $^{19}F$ NMR resonances, including the main PFPE peak at −91 ppm. The highest $R_1$ observed (158.2±2.5 $s^{-1}$ at 11.7 T), with a linewidth of 4 kHz, was with FETRIS saturated with $Fe^{3+}$. Despite the largest number of unpaired electrons, $Gd^{3+}$ showed a two-fold lower $R_1$ compared to $Fe^{3+}$, with severe line broadening. $Mn^{2+}$ gave moderately broad signals with the lowest $R_1$ of the triad. To confirm that the linewidth of metalated nanoemulsions is dominated by paramagnetism and not by metal binding per se, diamagnetic $Ga^{3+}$, with a similar ionic radius to $Fe^{3+}$, was included in the analysis and was found to have $R_1$ and $R_2$ equal to 2.08±0.01 s and 20.9±0.3 $s^{-1}$, respectively. Also, the small change in relaxation rates relative to the unmetalated emulsion, with $R_1$=2.37±0.01 $s^{-1}$, and $R_2$=15.1±0.2 $s^{-1}$ (9.4 T), is attributable to an increase in the effective molecular weight upon formation of the metal complex.

Paramagnetic nanoemulsion droplets also impact the $^1H$ relaxation rates of surrounding water. In FETRIS nanoemulsion, $^1H$ longitudinal and transverse relaxivities were $r_1$=0.37 and $r_2$=4.6 $mM^{-1}s^{-1}$, respectively. Thus, FETRIS functions as a $^1H$ $T_2$ contrast agent, which may be useful for correlating $^{19}F$ signals to co-registered $^1H$ anatomical images.

Figure 3:
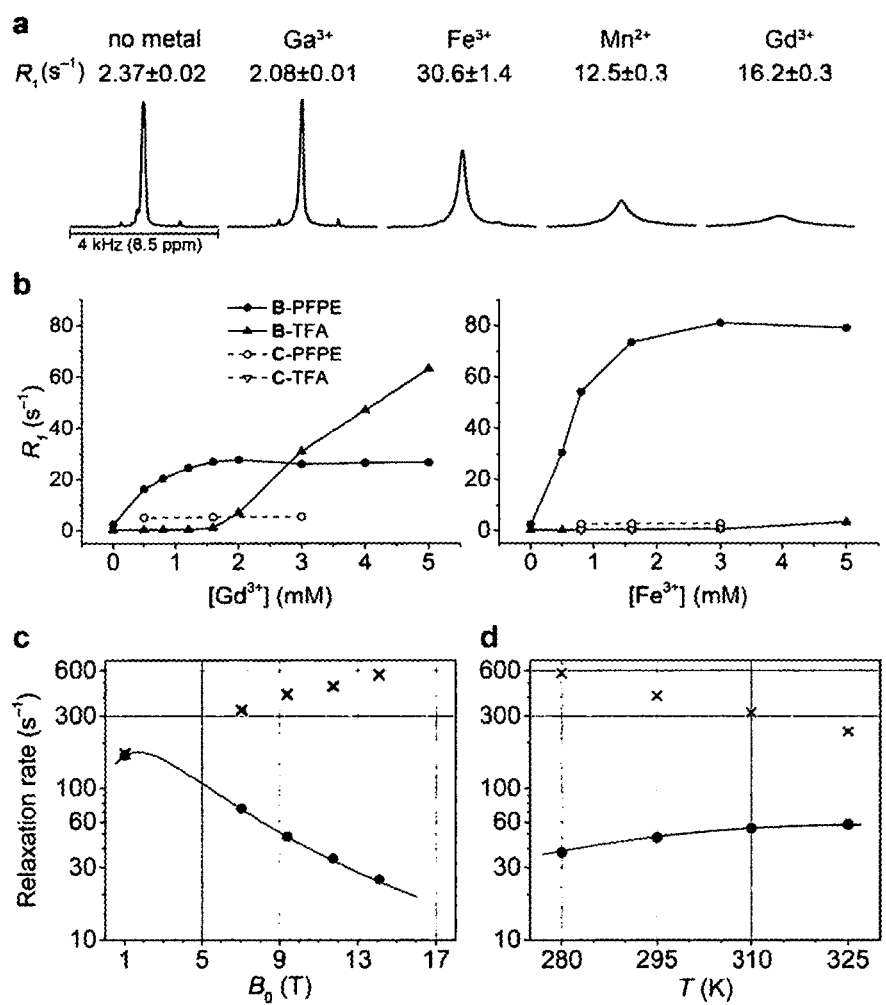
FIG. 3A-3D. Fluorine-19 relaxometry of metalated PFPE emulsions.
Figure 16:
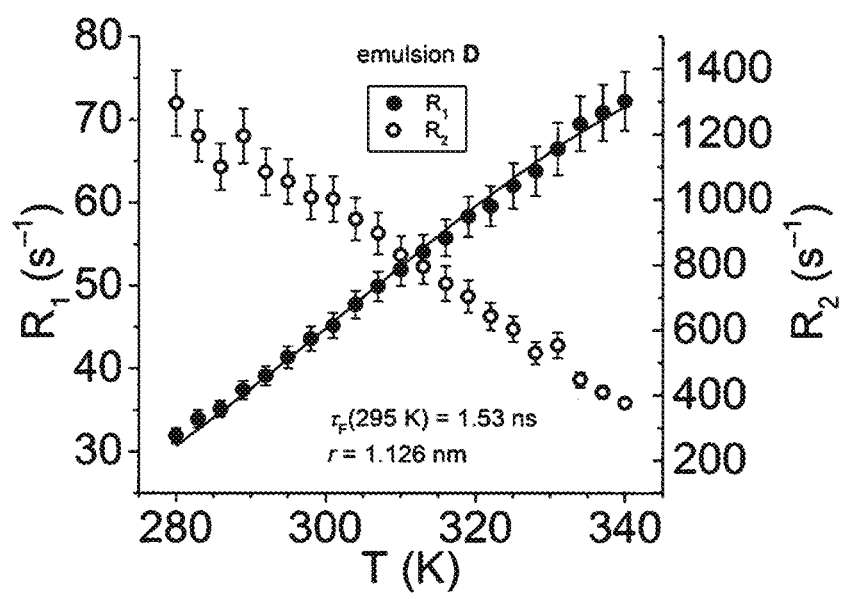
Figure 17:
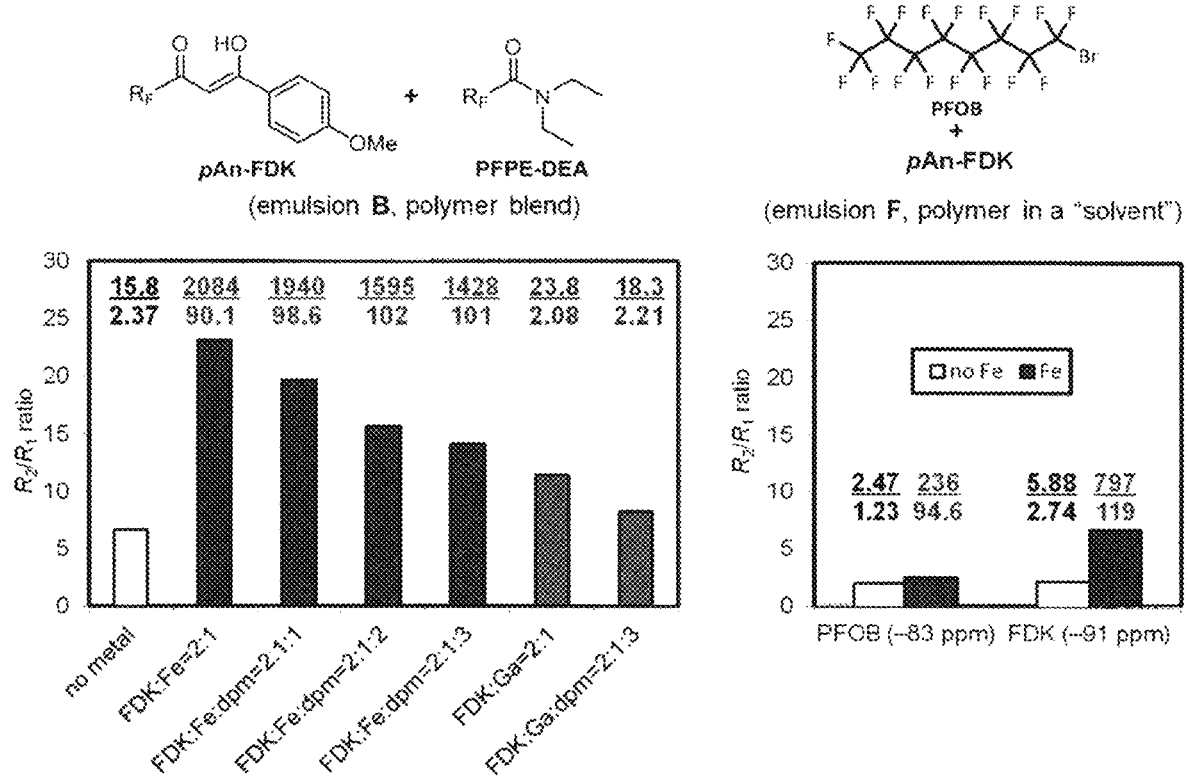
FIG. 17. Reducing $R_2/R_1$ ratio by modulating $\tau_F$. Shown are $^{19}$F $R_2/R_1$ ratios in emulsions B and F in the presence of saturating concentrations of Fe$^{3+}$ or Ga$^{3+}$, and an auxiliary ligand dipivaloylmethane (dpm) at 11.7 T. Individual $R_2$ (numerator) and R (denominator) values (s$^{-1}$) are shown above the bars. An increase in $R_2/R_1$ on metalation with both paramagnetic (Fe$^{3+}$) and diamagnetic (Ga$^{3+}$) ions is likely caused by lengthening of $\tau_F$ due to an increase in molecular weight and viscosity upon metal chelate formation, as well as possible formation of a coordination polymer. The effective molecular weight of metal chelate can be reduced with a competing small molecule dpm ligand, resulting in reduced $R_2/R_1$. Reduced viscosity on switching from PFPE-DEA to PFOB$^5$ (emulsion F) decreases $\tau_F$ and thus $R_2/R_1$ ratios.
Figure 18:
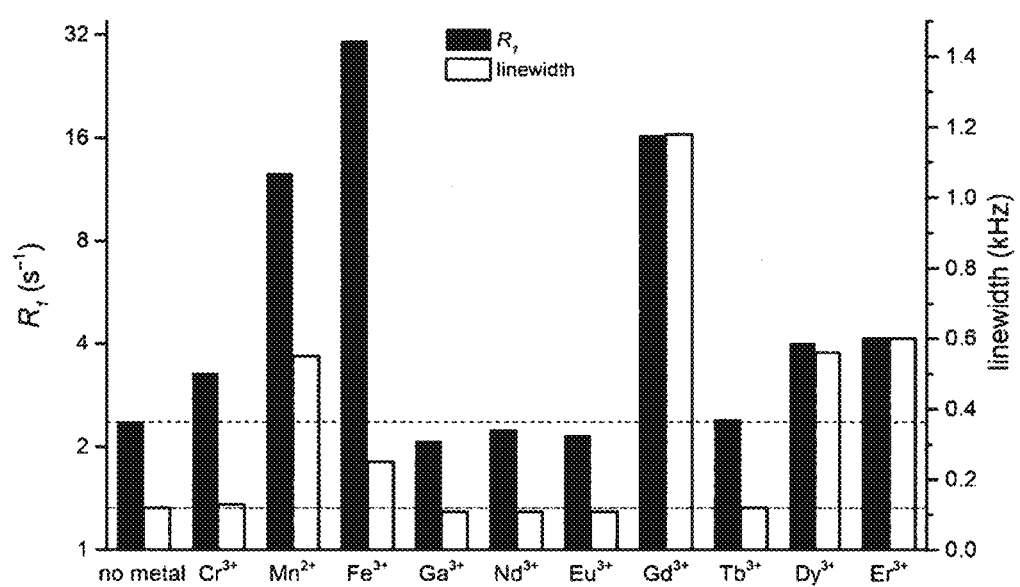
FIG. 18. $^{19}$F relaxometry of nanoemulsion loaded with various metals. Shown are R and linewidth at half-maximum of the main PFPE peak (−91 ppm) in emulsion B (3.5 mM diketone) loaded with metals (0.5 mM) in HEPES buffer (15 mM, pH 7.4) at 11.7 T. Dashed and dash-dotted lines represents $R_1$ (2.37 s$^{-1}$) and linewidth (0.12 kHz) in the absence of metals, respectively. We note that we did not test second and third row transition metals and Co$^{3+}$, as these metals ions do not form high-spin complexes; Mn$^{3+}$ tris-diketonates (high-spin d$^4$ complexes) are strong oxidants.

The phase distribution of the paramagnetic ions and the metal binding capacity of FDK nanoemulsions was determined (FIG. 3B). Measurement of $R_1$ at 11.7 T for both PFPE (fluorous phase) and trifluoroacetate reference (TFA) added to the aqueous phase revealed that nanoemulsions efficiently extracted $Gd^{3+}$ and $Fe^{3+}$ from water into the fluorous phase. $R_1$ of PFPE reached a plateau at ligand-to-metal ratio of ca. 2.5; increasing metal concentration further affected the $R_1$ of TFA. Notably, an increase in $R_1$ of TFA was observed even at the lowest $Gd^{3+}$ concentration in pure PFPE nanoemulsion, confirming that the paramagnetic ion stays in the aqueous phase. Without being bound by theory, it was speculated that the modest (~2-fold) increase in $R_1$ of PFPE in this case was likely due to binding of $Gd^{3+}$ ions to the nanoemulsion surface[8, 10]. A divergent field and temperature dependence of $R_1$ and $R_2$ in FETRIS nanoemulsions was observed (FIGS. 3C, 3D, and 16). Further control over relaxation parameters was achieved by tuning molecular weight and viscosity of the emulsion components (FIG. 17). Other rare earths had only a minor effect on $R_1$, consistent with fast electronic relaxation in these metal ions[20] (FIG. 18).

Figure 4:
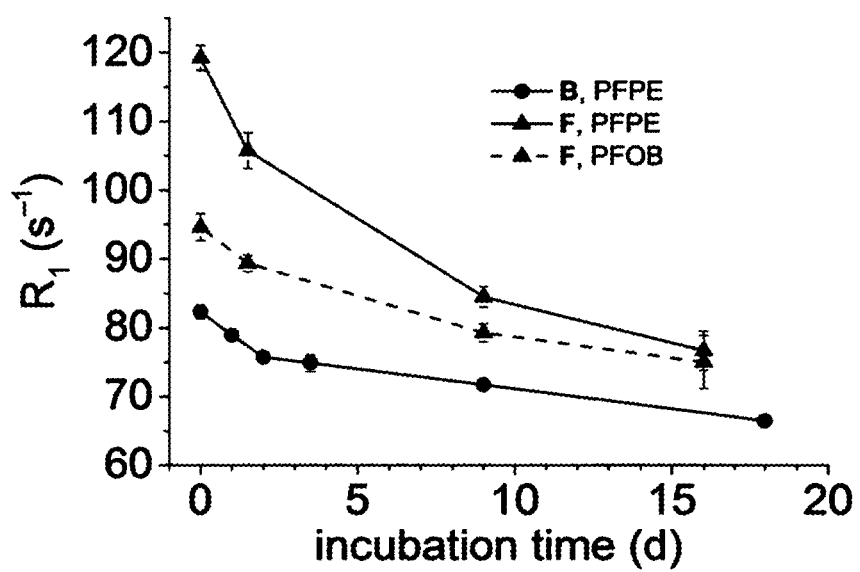
FIG. 4. Relaxometry stability of FETRIS nanoemulsions in the presence of competing aqueous ligand. Nanoemulsion B and F, both metalated with 0.7 mM $Fe^{3+}$, were treated at 37° C. with 75 mM EDTA dissolved in aqueous phase. Shown are $R_1$ values of PFPE (—●—) in nanoemulsion B, and values for blend nanoemulsion F, including PFPE components (—▲—) and the $CF_3$ signal of PFOB (- - ▲ - -). A slight decrease over time is observed, as slow $Fe^{3+}$ efflux occurs from the fluorous phase and irreversibly binds to EDTA. Error bars are standard deviations from three independent replicates.

The stability of metal-FDK complexes was evaluated. Using metal-loaded nanoemulsion, changes in photoluminescence ($Eu^{3+}$) and absorbance ($Fe^{3+}$) in the presence of excess competing ligands to study potential leakage of metal from the fluorous phase were monitored. Ethylenediaminetetraacetate (EDTA), a strong metal chelator[21], rapidly (<5 min) abolished the photoluminescence of europium-loaded emulsion due to complete sequestration of $Eu^{3+}$ to the aqueous phase to form a non-photoluminescent EDTA complex. In contrast, FETRIS nanoemulsion showed no decrease in characteristic absorbance of the $Fe^{3+}$ chelate, even with prolonged exposure to EDTA. To estimate long-term stability of FETRIS nanoemulsions, relaxation rates were measured in the presence of EDTA (FIG. 4). PFPE-based nanoemulsion showed <20% decrease in $R_1$ over 2 weeks of incubation at 37° C. with EDTA.

Figure 5:
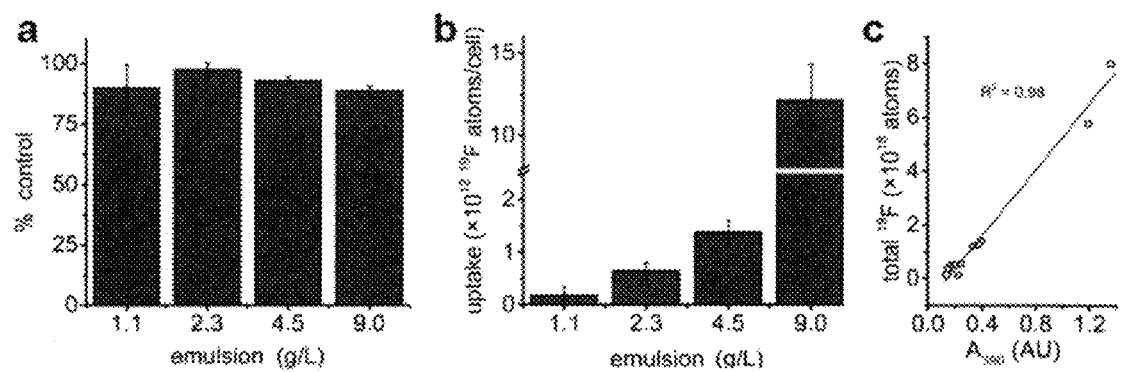
FIGS. 5A-5C. Cell labeling with FETRIS nanoemulsion. Cells (GL261) were labeled in culture using FETRIS nanoemulsion.

Next, FETRIS nanoemulsion properties in labeled cells were examined. Ex vivo labeling of a rodent glioma cell line (GL261) with FETRIS showed good viability post-labeling (FIG. 5A), with loadings on the order of ~$10^{12}$ $^{19}F$ atoms/cell (FIG. 5B). Uptake of FETRIS was evident by the orange color of cell pellets, and optical absorbance in the lysate correlated with the $^{19}F$ content determined by NMR (FIG. 5C). Fluorine-19 relaxometry of labeled cells (FIGS. 19A-E) showed that FETRIS nanoemulsion did not appear to lose $Fe^{3+}$ to the intracellular milieu over time; moreover, in the same nanoemulsion formulated without added $Fe^{3+}$, it did not appear to sequester endogenous $Fe^{3+}$ from the cell's labile iron pool (FIG. 19C). However, $Gd^{3+}$ substituted for $Fe^{3+}$ in the nanoemulsion displayed evidence of some metal leakage upon cell labeling; ca. 25% reduction of $^{19}F$ $R_1$ values after labeling was observed (FIG. 19D).

Magnetic Resonance Imaging with FETRIS

Figure 6:
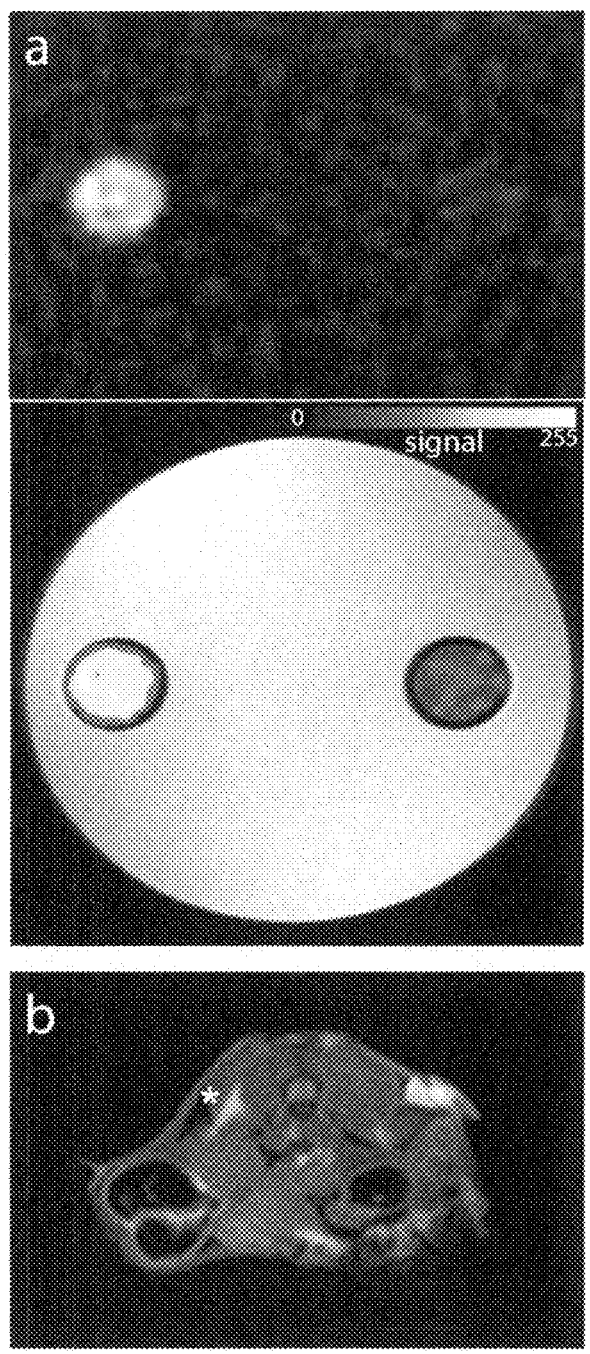
FIGS. 6A-6B. MRI of FETRIS nanoemulsion.
Figure 7:
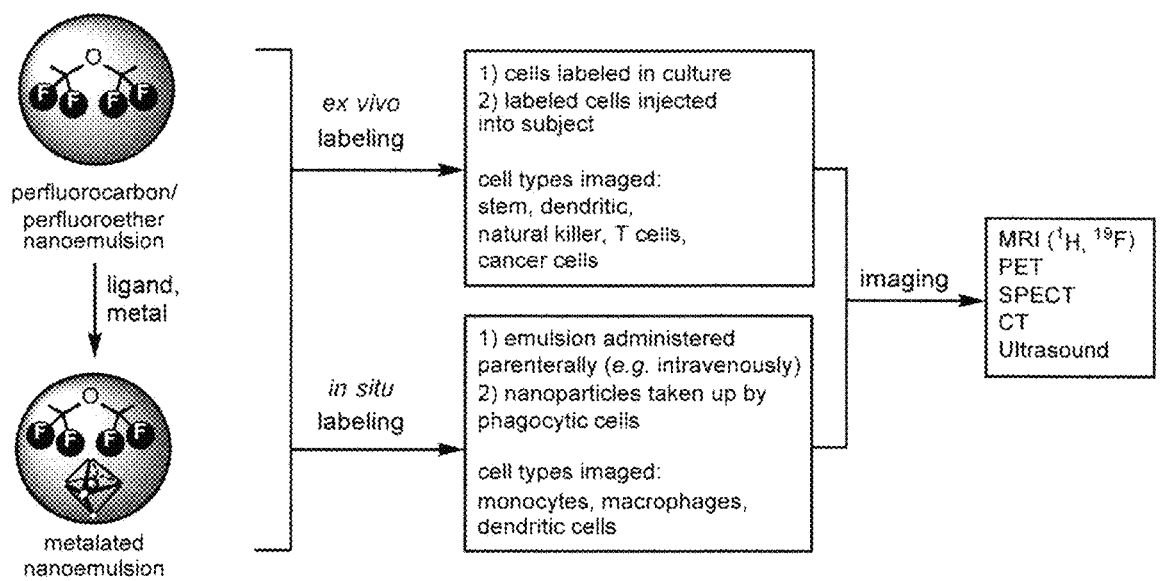
Figure 8:
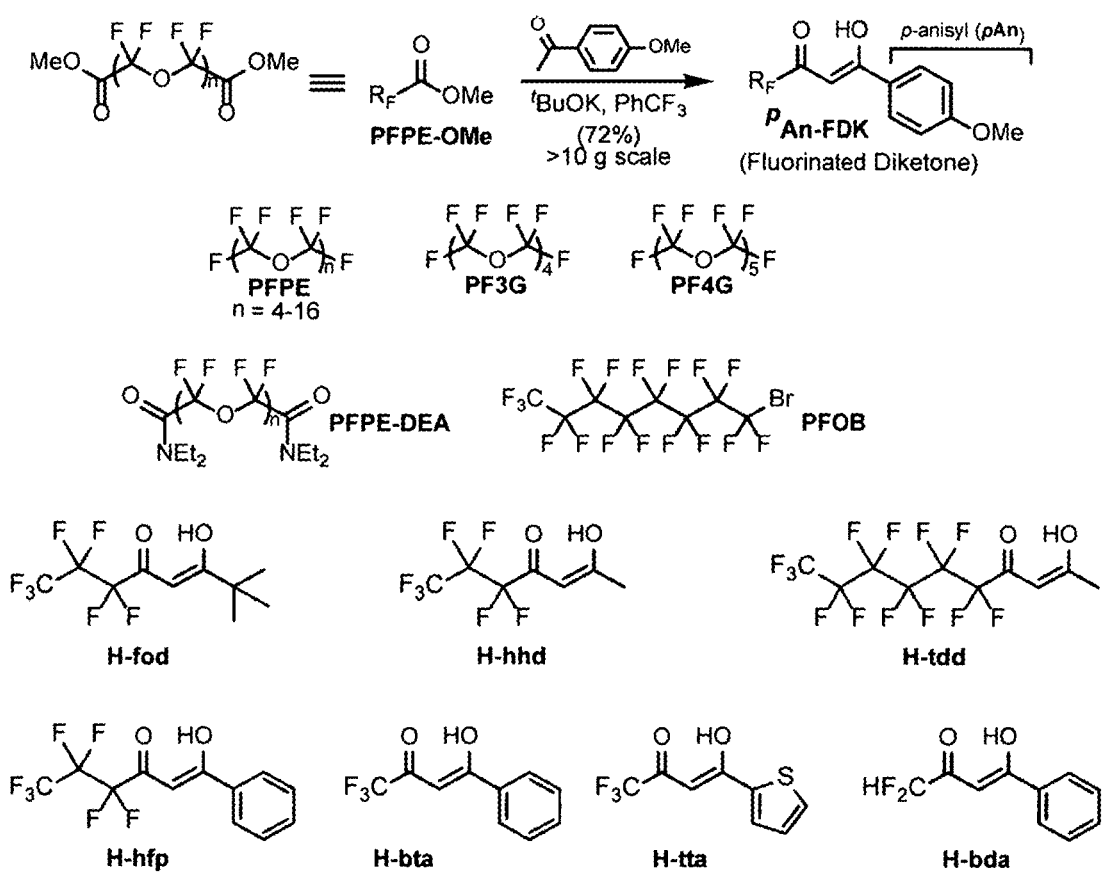
FIG. 8. Metal-binding and inert fluorocarbons used in $^{19}F$ MR imaging formulations.

Phantom $^{19}F$ MRI studies demonstrated the feasibility of imaging FETRIS using conventional MRI methods. A phantom sample was prepared consisting of two NMR tubes containing FETRIS prepared with parameters $R_1/R_2$=32.5/170 $s^{-1}$ and the same emulsion without metal ($R_1/R_2$=2.2/3.7 $s^{-1}$); tubes were embedded in agarose. Images were acquired at 11.7 T using a spin-density weighted gradient echo (GRE) sequence, with scanning parameters set at the Ernst angle condition[9] for optimal imaging of the FETRIS specimen, and a ~4 min image acquisition time. FIG. 6A displays phantom MRI results, where the FETRIS sample appears hyperintense; the measured $^{19}F$ image SNR for FETRIS and Fe-negative specimens were 8.6 and 1.7, respectively, yielding a SNR improvement of ~5 for the FETRIS sample, without Rician correction for low SNR regime[3+]. If each capillary was imaged using its appropriate Ernst angle, the SNR improvement would be ~3.3 (see modeling results and FIG. 20). To further minimize potential $T_2$ signal loss when imaging FETRIS agents, one could potentially use so called Ultrashort TE (UTE) or Zero TE (ZTE) pulse sequences[7]. Pulse sequences like GRE are commonplace on clinical scanners, whereas ZTE is not yet readily provided by MRI vendors.

Preliminary in vivo imaging of FETRIS-labeled cells was performed. Glioma cells were labeled with FETRIS nanoemulsion (50 wt. % pAn-FDK, 50 wt. % PFPE) ex vivo to a level of ~$10^{12}$ $^{19}F$/cell. A second batch of glioma cells was labeled at comparable levels with PFPE emulsion without metal. Cells ($5 \times 10^6$ per side) were injected subcutaneously into left (no metal) and right (FETRIS) flanks in syngeneic C57BL/6 mice (N=3). After 24 hours, mice were imaged with $^1H/^{19}F$ MRI at 11.7 T (FIG. 6B). The $^{19}F$ images were acquired using a three-dimensional ZTE sequence (FIG. 6B). Cells were readily visible (SNR-7) in the right injected flank (FIG. 6B), but not on the left side (no metal). Future in vivo studies will utilize FETRIS to image stem cells and immune cell populations in preclinical models.

Outlook

Figure 20:
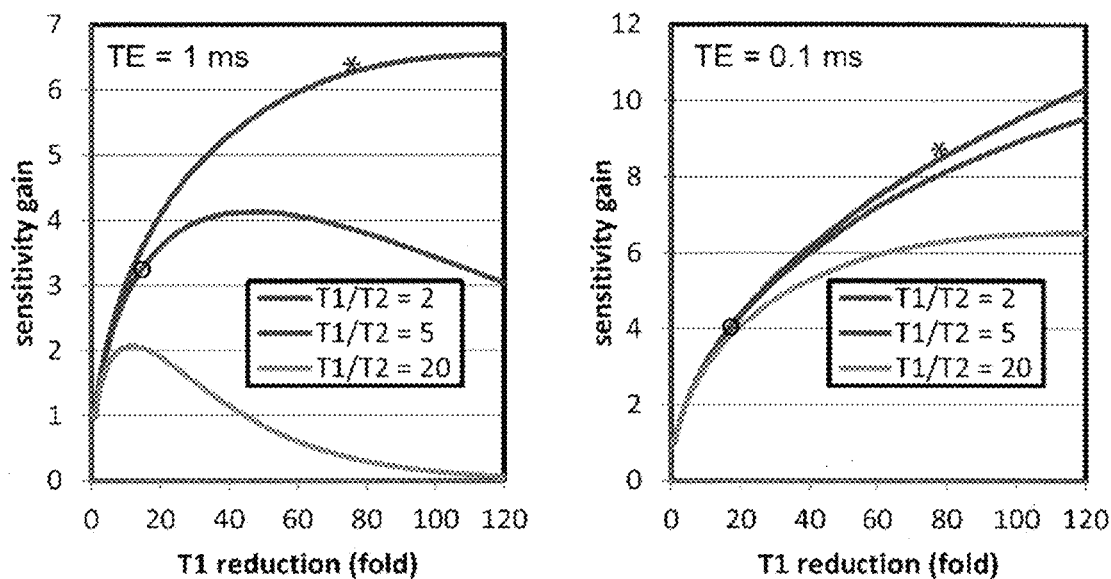
FIG. 20. Simulation results, for GRE sequence, of potential MRI sensitivity improvement using the paramagnetic FETRIS compared to diamagnetic (metal-free) perfluorocarbon, corrected per unit time. Here 'T1 reduction' is the $T_1$ ratio of diamagnetic versus FETRIS perfluorocarbon. Results for TE=1 ms (left) and TE=0.1 ms (right) are shown; the three curves converge as TE→0. The inset legend displays a range of $T_1/T_2$ ratios for FETRIS, which generally depend on both the FETRIS Fe concentration and the magnetic field strength. Symbols 'o' and '*' denote the predicted sensitivity improvements at 11.7 T and 3 T, respectively. The simulation assumes TR=0.5×$T_1$(FETRIS) and Ernst angle excitation for each agent (i.e., FETRIS and diamagnetic, in separate images).
Figure 22:
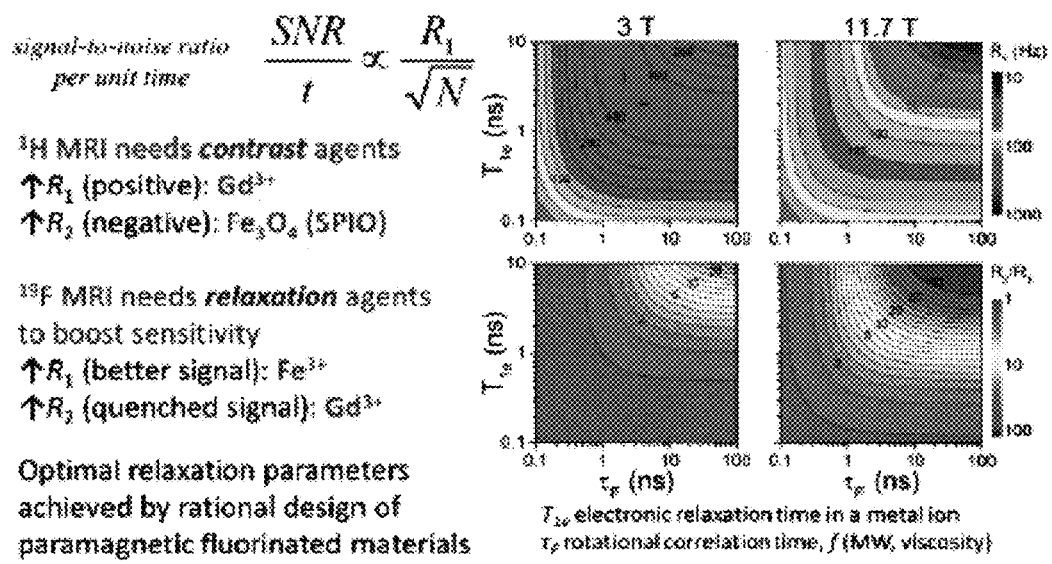
FIG. 22. Boosting sensitivity of $^{19}$F MRI.
Figure 23:
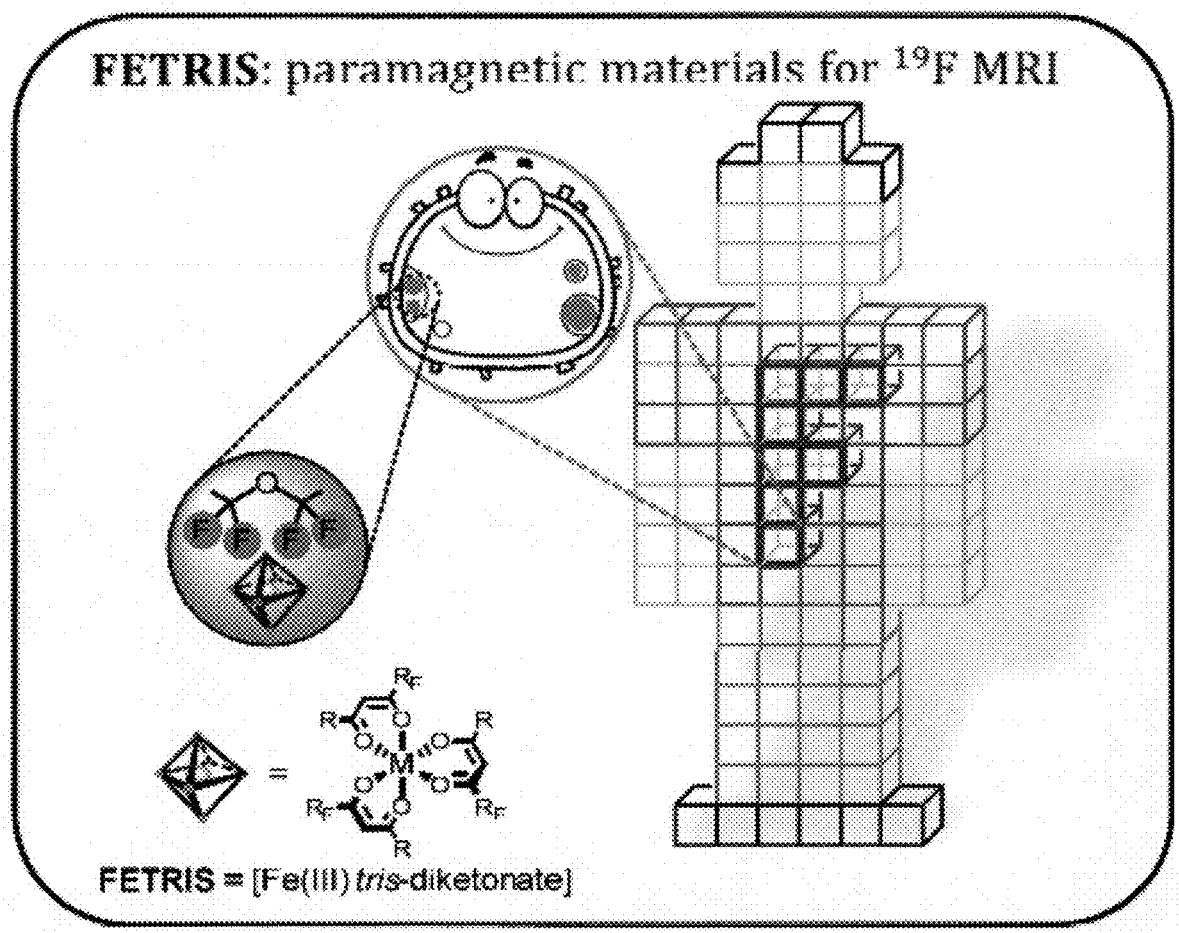
FIG. 23. FETRIS: paramagentic materials for $^{19}$F MRI.
Figure 24:
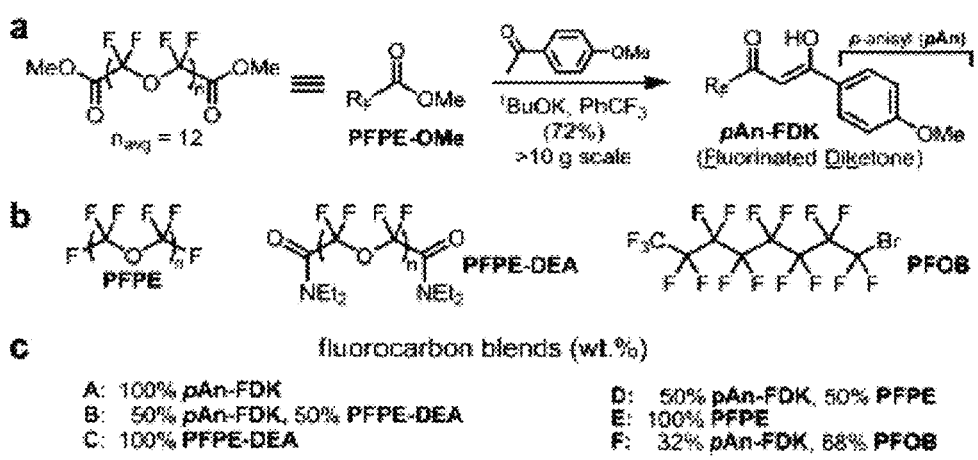
FIG. 24. Synthesis of fluorinated ligands.
Figure 25:
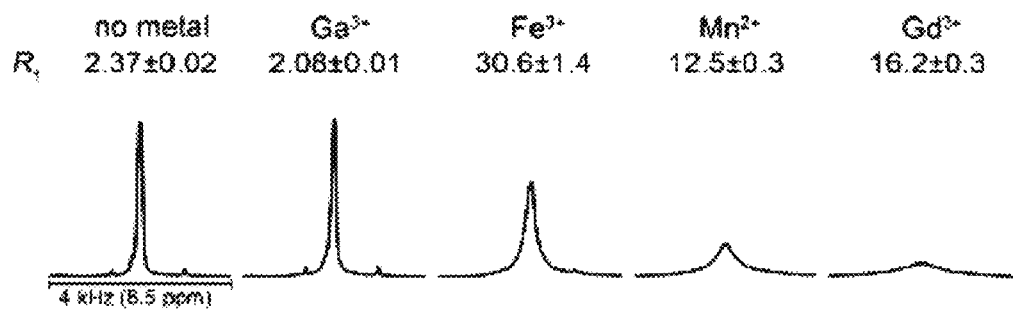
FIG. 25. Choosing the metal for metalation.
Figure 26:
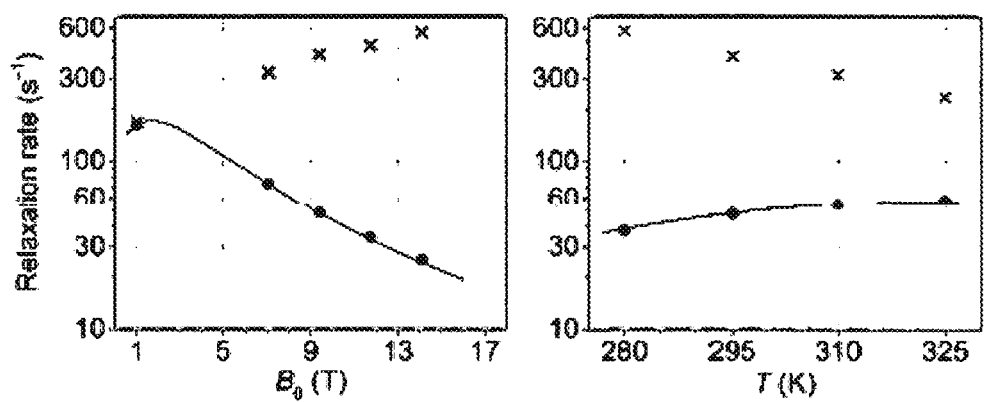
FIG. 26. Variable field and temperature relaxometry.
Figure 27:
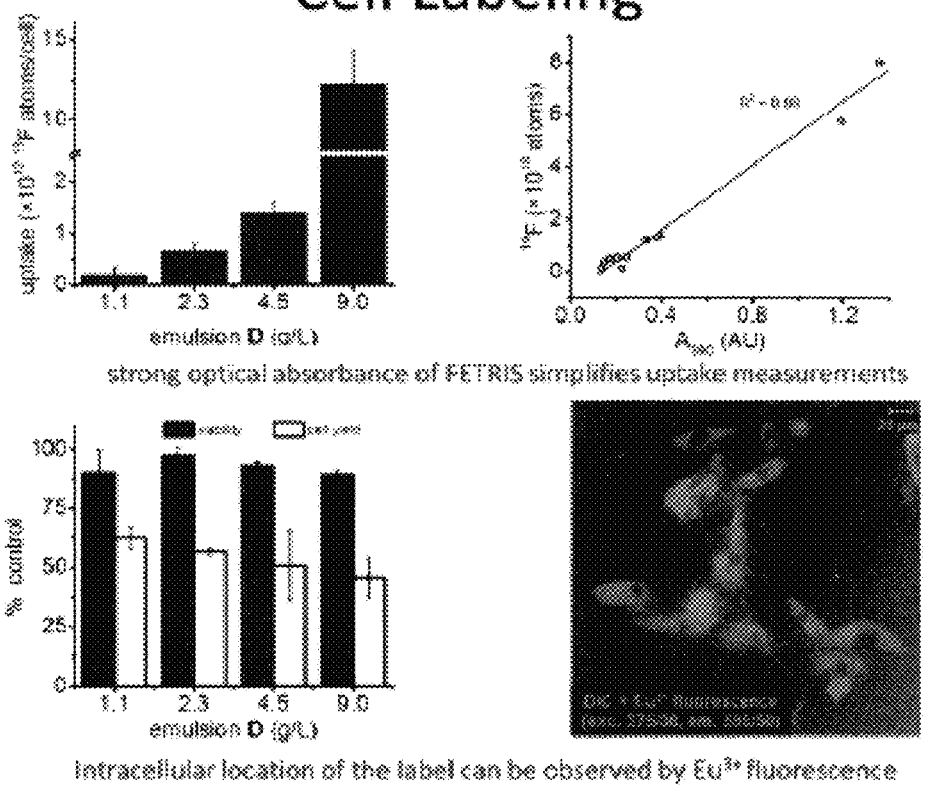
FIG. 27. Cell labeling using FETRIS.

Here we present a unique approach for formulating nanoemulsions using PFPE-based β-diketones (FDK) as metal chelators. These ligands have previously been studied in the context of material science[16], NMR spectroscopy[22], and catalysis[23]. FDK was shown to be well-suited for incorporating large amounts of paramagnetic metal ions into the fluorous liquids. Formulated as stable PFPE-in-water nanoemulsions, FDK efficiently and irreversibly extract $Fe^{3+}$ ions from aqueous solution into the fluorous phase, giving rise to cytocompatible FETRIS agent. These paramagnetic materials are useful for $^{19}F$ MRI with enhanced sensitivity due to a dramatic reduction in $T_1$, a fundamental parameter limiting the speed of MRI data acquisitions. The $^{19}F$ $T_1$ value reduction is magnetic field-strength dependent, but can potentially be accelerated to values approaching 80× at clinical field strengths, yielding a >8-fold sensitivity increase in $^{19}F$ detection (FIG. 20). These sensitivity increases diminish at higher magnetic field strengths (FIG. 20). FETRIS was shown to be effective for $^{19}F$ MRI using conventional MRI pulse sequences.

$Gd^{3+}$ and $Fe^{3+}$ are at the heart of $T_1$- and $T_2$-based $^1H$ contrast agents, respectively, but for $^{19}F$ MRI, the roles of these metal ions are reversed. $Fe^{3+}$ was the optimal $T_1$ enhancer for perfluorocarbons, while analogous gadolinium (and manganese) chelates caused severe line broadening, essentially becoming $^{19}F$ $T_2$ agents. Paramagnetic relaxation enhancement has been previously applied to $^{19}F$ nuclei[7, 20, 24, 25]. $^{19}F$ MR probes based on macrocyclic lanthanide complexes with fluorinated substituents has been described[7, 20]. However, these paramagnetic $^{19}F$ tracers are not ideal for cell detection purposes. The relatively low $^{19}F$ content of osmotically active macrocyclic chelates makes it difficult to reach MR-detectable cell loadings compared to highly-fluorinated PFC oils. In other approaches, Gd macrocyclic chelates bound to nanoemulsion surface can be used to provide a modest enhancement of $^{19}F$ $T_1$, but these are unstable in the intracellular milieu, especially if they traffic to low pH compartments[28], which tends to separate the chelate from nanoemulsion droplet, thereby limiting long-term enhancement. In contrast, FETRIS complexes are characterized by very small rates of metal leakage even in the presence of EDTA in vitro and after cell labelling. The toxicity testing of FETRIS as reported here is viewed as preliminary; more rigorous in vitro cell studies, as well as animal testing, are needed to determine potential suitability for clinical trials. We note that emerging $^1H$ MRI techniques like PARACEST[26] and highly shifted proton MRI[27] have shown promise to detect multiple cell populations on standard MRI instrumentation with high specificity.

Overall, $^{19}F$ MRI cell detection using PFC tracer agents is a rapidly emerging alternative to $^1H$-based approaches using metal-ion-based contrast agents. The technical barriers associated with implementation of $^{19}F$ MRI on a clinical scanner are surmountable, and clinical $^{19}F$ cell detection has recently been demonstrated[5]. Future improvements in sensitivity of the probes will only accelerate adoption of this technology and open up new uses for this technology; towards this goal, the excellent stability and unique magnetic properties of FETRIS should advance this field.

Methods

Emulsion Preparation

The fluorocarbon oil blends were prepared from PFPE, PFPE-DEA (Exfluor, Round Rock, Tex.), PFOB (Acros, Pittsburgh, Pa.), and pAn-FDK (see SI, Supplementary Methods for synthetic procedures) agents. Proportions (FIG. 2) were prepared gravimetrically in a 15 or 50 mL conical Falcon tube (Corning). Per 1 gram of PFC blend, 0.5 mL aqueous solution of Pluronic F68 (100 g/L) was added, and the mixture was vortexed at the highest speed. Water (8.5 mL) was added, followed by brief vortexing and ultrasonication (Omni Ruptor 250 W, 30% power, 2 minutes, Omni International, Kennesaw, Ga.). The crude emulsion thus obtained was passed 4-6 times through LV1 microfluidizer (Microfluidics, Westwood, Mass.) operating at 20,000 psi and filtered through a 0.2 μm Supor membrane (Pall Corp. #4187, Port Washington, N.Y.) into sterile glass vials.

NMR Measurements

NMR spectra were obtained on Magritek Spinsolve (1.0 T), Bruker Avance 300 (7.0 T), Bruker Ascend 400 (9.4 T), Jeol ACA 500 (11.7 T), and Bruker DRX-600 (14.1 T) instruments. $^{19}F$ NMR spectra of aqueous nanoemulsions were referenced to an internal standard (0.1 wt. % $CF_3CO_2Na/D_2O$, −76.00 ppm), which served as integration reference for quantitative NMR (see SI). Relaxation measurements were performed using a standard inversion recovery (with TI from $3^{-2}$ to $3^9$ ms) pulse sequence and a Carr-Purcell-Meiboom-Gill sequence with TE values in 12 linear increments. $R_1$ and $R_2$ were obtained by non-linear fitting in MNova 6.0.2 software (Mestrelab, Escondido, Calif.). Fit errors were less than 5% for $R_1$ and 10% for $R_2$.

Cell Labeling

Rat 9L or mouse GL261 glioma cells ($3-5 \times 10^6$, ATCC, Manassas, Va.) were plated in 10 cm dishes and allowed to attach overnight. Immediately before cell labeling, FDK (B or D) or control (C or E) emulsion (0.5 mL) was mixed with freshly prepared $FeCl_3$ (50 mM in $H_2O$, 0.12 mL), protamine sulfate (1% in $H_2O$, 0.02 mL), and Tris base (1 M in $H_2O$, 0.25 mL). The dark-orange liquid was diluted to the desired PFPE content with DMEM (9L) or RPMI-1640 (GL261) media supplemented with 10% (v/v) fetal bovine serum (FBS). Labeling medium was added to cells at 5 mL/dish. After 16 h incubation at 37° C., the cell labeling medium was removed, and cells were washed three times with phosphate buffered saline (PBS), detached by trypsinization, washed again in PBS, and resuspended in 1 mL of PBS. A portion of the cell suspension (~1/10) was used for cell number estimates by Cell Titer Glo (Promega, Madison, Wis.) or using a Countess II FL Cell Counter (Life Technologies, Carlsbad, Calif.). To assay nanoemulsion uptake, cells were pelleted and resuspended in 0.1 mL of lysis solution (0.5% Triton X, 100 mM NaCl, 20 mM Tris). A portion of this solution (6 μL) was used for absorbance measurements on NanoDrop 2000 spectrophotometer (Thermo Scientific, Pittsburgh, Pa.). The remainder was transferred to a 5 mm NMR tube, mixed with 0.15 mL of 0.1 wt. % $CF_3CO_2Na/D_2O$ reference compound and $^{19}F$ NMR spectra were obtained to measure $^{19}F$ uptake, as previously described[29].

MRI

A phantom sample was prepared using 5 mm NMR tubes containing FETRIS (4.5 g/L $^{19}F$, 0.5 mM $Fe^{3+}$, $R_1/R_2$=32.5/170 $s^{-1}$) and nanoemulsion without metal ($R_1/R_2$=2.2/3.7 $s^{-1}$); tubes were embedded in agarose. All images were acquired using a Bruker 11.7 T BioSpec using a $^{19}F/^1H$ double tuned volume coil. For $^{19}F$, a gradient echo (GRE) pulse sequence was used with parameters: TR/TE=15/0.83 ms (TR=recovery time), NA=256 (NA=number of averages), FOV=4×4 cm (FOV=field of view), 64×64 matrix, 8 mm thick slices, and a ~4 min data acquisition time. In this image, the echo time (TE) parameter was minimized to 0.83 ms, but at this value there is a residual amount of signal attenuation from $T_2$-effects in the FETRIS material (estimated ~12%). The Ernst angle condition[9] for optimal $^{19}F$ imaging of the FETRIS phantom was used. For $^1H$, the GRE parameters were TR/TE=150/2 ms, NA=8, FOV=4×4 cm, 256×256 matrix, and 2 mm slices. The $^{19}F$ image data was rendered in hot-iron pseudo-color using ImageJ software (NIH) and overlaid onto the grayscale $^1H$ image. For in vivo mouse studies, mouse GL261 glioma cells were labeled with FETRIS nanoemulsion (50 wt % pAn-FDK, 50 wt. % PFPE) ex vivo to a level of ~$10^{12}$ $^{19}F$/cell. A second batch of cells was similarly labeled but with unmetalated nanoemulsion. Cells ($5 \times 10^6$ per side) were injected subcutaneously into flanks in female syngeneic C57BL/6 mice (8-10 weeks old, N=3) using a vehicle of 0.2 ml Matrigel (BD Biosciences, Franklin Lakes, N.J.) in PBS. The FETRIS labeled cells, and cells labeled with unmetalated nanoemulsion, were injected into the right and left sides, respectively. After 24 hours, mice were imaged using a three-dimensional ZTE sequence with parameters TR=4 ms, receiver bandwidth 40 kHz, acquisition window 0.8 ms, number of projections 13030, NA=26, acquisition time 23 min, FOV=6×6×6 cm, and matrix size 64×64×64. Proton data were acquired using a two-dimensional spin-echo sequence with TR/TE=1500/14 ms, FOV=6×6 cm, and 256×256 matrix. $^{19}F$ data were imported into Amira software (FEI, Hillsboro, Oreg.) and rendered in color and a grayscale slice from the $^1H$ data was embedded for anatomical display purposes.

REFERENCES

1. Ahrens, E. T. & Bulte, J. W. M. Tracking immune cells in vivo using magnetic resonance imaging. *Nat Rev Immunol* 13, 755-763 (2013).
2. Ahrens, E. T., Flores, R., Xu, H. Y. & Morel, P. A. In vivo imaging platform for tracking immunotherapeutic cells. *Nat Biotechnol* 23, 983-987 (2005).
3. Srinivas, M., Morel, P. A., Ernst, L. A., Laidlaw, D. H. & Ahrens, E. T. Fluorine-19 MRI for visualization and quantification of cell migration in a diabetes model. *Magn Reson Med* 58, 725-734 (2007).
4. Srinivas, M. et al. In vivo cytometry of antigen-specific T cells using $^{19}F$ MRI. *Magn Reson Med* 62, 747-753 (2009).
5. Ahrens, E. T., Helfer, B. M., O'Hanlon, C. F., Schirda, C. Clinical cell therapy imaging using a perfluorocarbon tracer and fluorine-19 MRI. *Magn Reson Med* 72, 1696-1701 (2014).
6. Neubauer, A. M. et al. Gadolinium-modulated F-19 signals from perfluorocarbon nanoparticles as a new strategy for molecular imaging. *Magn Reson Med* 60, 1066-1072 (2008).
7. Schmid, F., Holtke, C., Parker, D. & Faber, C. Boosting $^{19}F$ MRI-SNR efficient detection of paramagnetic contrast agents using ultrafast sequences. *Magn Reson Med* 69, 1056-1062 (2013).
8. de Vries, A. et al. Relaxometric studies of gadolinium-functionalized perfluorocarbon nanoparticles for MR imaging. *Contrast Media Mol* 19, 83-91 (2014).
9. Brown, R. W., Cheng, Y. C. N., Haacke, E. M., Thompson, M. R. & Venkatesan, R. Magnetic Resonance Imaging: Physical Prinicples and Sequence Design, Edn. 2nd Edition. (John Wiley & Sons, Hoboken, N.J.; 2014).
10. Hu, L., Zhang, L., Chen, J., Lanza, G. M. & Wickline, S. A. Diffusional mechanisms augment the fluorine MR relaxation in paramagnetic perfluorocarbon nanoparticles that provides a "relaxation switch" for detecting cellular endosomal activation. *J Magn Reson Imaging* 34, 653-661 (2011).
11. Solomon, I. Relaxation processes in a system of two spins. *Phys Rev* 99, 559-565 (1955).
12. Bloembergen, N. & Morgan, L. O. Proton relaxation times in paramagnetic solutions. Effects of electron spin relaxation. *J Chem Phys* 34, 842-850 (1961).

13. Marchionni, G., Ajroldi, G., Righetti, M. C. & Pezzin, G. Molecular interactions in perfluorinated and hydrogenated compounds: Linear paraffins and ethers. *Macromolecules* 26, 1751-1757 (1993).
14. Lai, C.-Z., Reardon, M. E., Boswell, P. G. & Bühlmann, P. Cation-coordinating properties of perfluoro-15-crown-5. *J Fluor Chem* 131, 42-46 (2010).
15. Shibata, S., Onuma, S. & Inoue, H. Crystal and molecular structure of trimeric bis(acetylacetonato)manganese (II). *Inorg Chem* 24, 1723-1725 (1985).
16. Binnemans, K. in Handbook on the Physics and Chemistry of Rare Earths, Vol. 35. (Eds. J.-C. G. B. Karl A. Gschneidner & K. P. Vitalij) 107-272 (Elsevier, 2005).
17. Barkley, L. B. & Levine, R. The synthesis of certain ketones and α-substituted β-diketones containing perfluoroalkyl groups. *J Am Chem Soc* 75, 2059-2063 (1953).
18. Janjic, J. M. & Ahrens, E. T. Fluorine-containing nanoemulsions for MRI cell tracking. *Wiley Interdisciplinary Reviews. Nanomedicine and Nanobiotechnology* 1, 492-501 (2009).
19. Lintvedt, R. L. & Kernitsky, L. K. Ligand field information from charge-transfer spectra of substituted tris(1,3-diketonato)iron(III) chelates. Spectrochemical series for 1,3-diketones. *Inorg Chem* 9, 491-494 (1970).
20. Funk, A. M., Fries, P. H., Harvey, P., Kenwright, A. M. & Parker, D. Experimental measurement and theoretical assessment of fast lanthanide electronic relaxation in solution with four series of isostructural complexes. *J Phys Chem A* 117, 905-917 (2013).
21. Nash, K. L., Brigham, D., Shehee, T. C. & Martin, A. The kinetics of lanthanide complexation by EDTA and DTPA in lactate media. *Dalton T* 41, 14547-14556 (2012).
22. Sanders, J. K. M., Hanson, S. W. & Williams, D. H. Paramagnetic shift reagents. Nature of the interactions. *J Am Chem Soc* 94, 5325-5335 (1972).
23. Lo, J. C., Gui, J., Yabe, Y, Pan, C.-M. & Baran, P. S. Functionalized olefin cross-coupling to construct carbon-carbon bonds. *Nature* 516, 343-348 (2014).
24. Harvey, P., Kuprov, I. & Parker, D. Lanthanide complexes as paramagnetic probes for $^{19}$F magnetic resonance. *Eur J Inorg Chem*, 2015-2022 (2012).
25. De Luca, E. et al. Characterisation and evaluation of paramagnetic fluorine labelled glycol chitosan conjugates for F-19 and H-1 magnetic resonance imaging. *J Biol Inorg Chem* 19, 215-227 (2014).
26. Ferrauto, G., Castelli, D. D., Terreno, E. & Aime, S. In vivo MRI visualization of different cell populations labeled with PARACEST agents. *Magn Reson Med* 69, 1703-1711 (2013).
27. Schmidt, R. et al. Highly shifted proton MR imaging: Cell tracking by using direct detection of paramagnetic compounds. *Radiology* 272, 785-795 (2014).
28. Kok, M. B. et al. Quantitative H-1 MRI, F-19 MRI, and F-19 MRS of cell-internalized perfluorocarbon paramagnetic nanoparticles. *Contrast Media Mol Imaging* 6, 19-27 (2011).
29. Janjic, J. M., Srinivas, M., Kadayakkara, D. K. K. & Ahrens, E. T. Self-delivering nanoemulsions for dual fluorine-19 MRI and fluorescence detection. *J Am Chem Soc* 130, 2832-2841 (2008).

Example 2: Paramagnetic Fluorinated Nanoemulsions for Sensitive Cellular Fluorine-19 Magnetic Resonance Imaging Theoretical Considerations for Paramagnetic Enhancement of Perfluorocarbons If a metal chelate is dissolved in a liquid fluorocarbon, the distance of closest approach ($r_{min}$) of $^{19}$F nuclei to the metal ion can be approximated by the summation of the van der Waals radius of a fluorine atom ($r_{VDW}$=0.147 nm) and Wigner-Seitz radius ($r_{WS}$) of the chelate, given by $r_{WS}$=(3M/$4\pi dN_A$)$^{1/3}$, where M is molecular weight of the chelate, d is density, and $N_A$ is Avogadro's number. Assuming M≥500 g/mol, and d≥1.5 g/cm$^3$, $r_{min}$ can be estimated to be >0.65 nm. The distance of greatest separation is determined by the concentration of metals in the fluorous phase, where 50 mmol/L (mM) corresponds to 1 atom per sphere of radius 2.0 nm. The concentration of metals in the fluorous phase of the emulsions presented here reaches 200 mM. Thus, the possible range of interatomic distances is very narrow, and is likely to be sampled evenly and rapidly by all $^{19}$F nuclei on the timescale of an NMR experiment. On this basis, we speculate that the translational diffusion invoked in modeling outer sphere relaxation can be neglected. Assuming that the modulation of electron-nuclear dipolar interaction can be described by a single rotational correlation time ($\tau_F$), paramagnetic relaxation enhancement (PRE) of $^{19}$F nuclei can be predicted using the Solomon-Bloembergen-Morgan (SBM) equations[1, 2]:

$$R_1 = \frac{2}{15}\left(\frac{\mu_0}{4\pi}\right)^2 \frac{\gamma_F^2 g^2 \mu_B^2 S(S+1)}{r^6}\left[\frac{3\tau_1}{1+B_0^2\gamma_F^2\tau_1^2} + \frac{7\tau_2}{1+B_0^2\gamma_e^2\tau_2^2}\right] + X_1 \quad (S1)$$

$$R_2 = \frac{1}{15}\left(\frac{\mu_0}{4\pi}\right)^2 \frac{\gamma_F^2 g^2 \mu_B^2 S(S+1)}{r^6}\left[4\tau_1 + \frac{3\tau_1}{1+B_0^2\gamma_F^2\tau_2^2} + \frac{13\tau_2}{1+B_0^2\gamma_e^2\tau_2^2}\right] + X_2 \quad (S2)$$

where $\mu_0$ is vacuum magnetic permeability, $\gamma_e$ and $\gamma_F$ are gyromagnetic ratios of electrons (176.1 GHz·rad/T) and $^{19}$F (0.2517 GHz·rad/T), respectively, g is the electronic spin g-factor, $\mu_B$ is the Bohr magneton, S is the spin of paramagnetic species M$^{n+}$, r is distance between M and F, $\tau_i$= $(\tau_F^{-1}+T_{ie}^{-1})^{-1}$ for i=1, 2, and $T_{1e}$ and $T_{2e}$ are longitudinal and transverse electronic relaxation times given by $$T_{1e}^{-1} = \frac{\Delta^2}{25}(4S(S+1)-3)\tau_v\left[\frac{1}{1+B_0^2\gamma_e^2\tau_v^2} + \frac{4}{1+4B_0^2\gamma_e^2\tau_v^2}\right] \quad (S3)$$

$$T_{2e}^{-1} = \frac{\Delta^2}{50}(4S(S+1)-3)\tau_v\left[3 + \frac{5}{1+B_0^2\gamma_e^2\tau_v^2} + \frac{2}{1+4B_0^2\gamma_e^2\tau_v^2}\right] \quad (S4)$$

where Δ is the amplitude of zero-field splitting fluctuations, $\tau_v$ is their correlation time. The term $X_i$ (i=1, 2) denotes all other contributions to relaxation rates $R_1$, such as susceptibility[3] and Curie[4] effects, both of which have almost no effect on $R_1$ but a significant, field-dependent effect on $R_2$. Neglecting $X_i$, equations (S1-S4) provide estimates of $R_1$ and lower limits on $R_2$.

The moderately-high molecular weight (500-2000 Da) and viscosity[5, 6] of fluorocarbon oils used for $^{19}$F MRI put a lower limit of ~0.1 ns on the correlation time $\tau_F$. Analysis of equations S1-S4 reveal that $R_1$ experiences the most significant enhancement at electronic relaxation times approaching 1 ns. High-spin ions such as Fe$^{3+}$, Mn$^{2+}$, and Gd$^{3+}$ have sufficiently slow electronic relaxation times that are generally assumed to be dominated by the modulation of zero-field splitting interactions[2, 7]. Studies on electronic and nuclear relaxation in aqueous solutions of various complexes of manganese and gadolinium[9, 10] showed that $T_{1e}$ of these ions could exceed 100 ns at moderate to high magnetic field strengths ($B_0$>1 T). The small size of $Fe^{3+}$ ion gives rise to high-frequency ZFS fluctuations (lower $\tau_v$), which leads to faster electronic relaxation (lower $T_{1e}$) than in $Mn^{2+}$ and $Gd^{3+}$.[11,12] As $T_{1e}$ of a paramagnetic species increases beyond 1 ns, line broadening (shown as $R_2/R_1$ ratio) becomes very sensitive to increases in $\tau_F$, due to decreasing $R_1$ and increasing $R_2$, especially at higher magnetic fields (FIG. 9). Thus, it is likely that $Fe^{3+}$ placed in MRI-relevant perfluorocarbons will provide robust enhancement of $^{19}F$ $R_1$, while $Mn^2$ and $Gd^{3+}$ are likely to cause severe line broadening due to a large increase in $R_2$.

To highlight the critical effect of viscosity on relaxation rates, we measured PRE caused by different metal ions in non-viscous organic solutions containing trifluorotoluene ($PhCF_3$) and iron or gadolinium chelates of dipivaloylmethane, $Fe(dpm)_3$ and $Gd(dpm)_3$. Under these conditions, gadolinium provided higher $R_1$ than iron, as expected from the greater spin of $Gd^{3+}$. Temperature increases (decrease in $\tau_F$) resulted in a reduction of both R and $R_2$ (FIG. 10), consistent with the system being in "fast-motion" regime ($1/\tau_F \gg \gamma_F B_0$). In contrast, the divergent temperature dependence of $R_1$ and $R_2$ in FETRIS nanoemulsion (FIG. 3D) is indicative of slow molecular motion in the fluorous phase.

Relaxation rates depend on multiple interdependent parameters. Accurate determination of these parameters requires the measurement of relaxation rates over a wider range of conditions, more than presented here. Thus, the parameters obtained from curve-fitting to variable field and variable temperature data in FIGS. 3C and 3D should be treated as only approximations. Nonetheless, they serve well to explain the trends observed, and form a basis for future investigations.

Simulation of $^{19}F$ MRI Sensitivity Gain from PRE

Numerical simulation can be used to predict the approximate $^{19}F$ MRI sensitivity gain from PRE of perfluorocarbon imaging agents. We assume a conventional spoiled gradient-echo (GRE) imaging sequence.[13] The signal detected after each excitation is given by $$S_\perp = \frac{(1-e^{-n})e^{-TE/T_2} \sin \alpha}{1-e^{-n} \cos \alpha} \quad (S5)$$

where n=$TR/T_1$, and we assume that n<1, $T_2 \approx T_2^*$, and Ernst angle ($\alpha$) excitation for each agent given by $\alpha = \cos^{-1}(e^{-n})$. The sensitivity gain realized by the reduced $T_1$ of FETRIS can be expressed as $$\text{gain} = \frac{S_\perp(\text{FETRIS})}{S_\perp(\text{diamagnetic})} \quad (S6)$$

were 'diamagnetic' denotes metal-free perfluorocarbon. Simulation results are displayed in FIG. 20, which use Eqs. S5-S6 and the relaxation rate curves in FIG. 3c, where values at 3 T were estimated by interpolation. Overall, the potential sensitivity gains are at least factors of eight and four at 3 T and 11.7 T, respectively. Sensitivity gains improve as TE→0. Cell detectability scales linearly with sensitivity gains.

Supplementary Methods

Synthesis of PAn-FDK Ligand

Unless otherwise noted, all solvents and reagents were obtained from commercial sources and used without further purification. PFPE-OMe (Exfluor Research, Round Rock, Tex.), a fluorinated derivative of polyethyleneglycol with $M_n$=600 (PEG-600) terminated with reactive ester groups, is a mixture of oligomers represented by a formula R'O ($CF_2CF_2O)_n CF_2CO_2Me$, where n=4-16, $M_n$=1750 g/mol, and R' represents $CF_2CO_2Me$, $CF_3$, or $CF_2CF_3$. The latter two functionalities originate from the cleavage of polymer backbone during fluorination, giving rise to minor peaks at −58, −90, and −93 ppm in $^{19}F$ NMR, and are chemically inert[14]. PFPE-OMe oil was determined to be ca. 80% bifunctional; the balance was considered monofunctional. $PhCF_3$ (Sigma-Aldrich, St. Louis, Mo., anhydrous, >99%) was stored over activated 4 Å molecular sieves. In a 100 mL round-bottom flask, PFPE-OMe (1.14 mmol reactive ester groups per gram, 13.36 g, 15.23 mmol), p-methoxyacetophenone (2.86 g, 19.04 mmol, 1.25 equiv), and dry $PhCF_3$ (20 g) were combined. This colorless, homogeneous mixture was vigorously stirred, and solid potassium t-butoxide (2.14 g, 19.04 mmol, 1.25 equiv) was added portionwise over 5 min. The resulting warm orange heterogeneous mixture was immersed into a 50° C. oil bath for 30 min, until a deep red homogenous solution was obtained. Crude $^{19}F$ NMR of the reaction mixture (25 µL aliquot in 450 µL $CD_3OD$, homogeneous solution) reveals complete conversion of the starting $R_FOCF_2CO_2Me$ ($\delta_F$—78.33, ref. $PhCF_3$ at −64.00 ppm) to product diketonate ($\delta_F$—79.01). The warm reaction mixture was poured into a 40:1 hexanes:acetic acid solution (120 mL), providing a yellow-brown suspension. The suspension was filtered, and volatiles were removed in vacuo. The resulting orange-brown oil was washed with MeOH (3×20 mL) and dried under high vacuum to a constant mass, yielding 10.92 g (72%) of yellow oil containing <1 wt. % of starting acetophenone by $^1H$ NMR. No $CF_2CO_2Me$/ $CF_2CO_2K$ signals (−78.9 ppm) were observed by $^{19}F$ NMR in $CDCl_3$.

During the addition of t-BuOK, an insoluble paste of solids consisting of t-BuOK and potassium diketonate (product) is formed preventing stirring. The complete conversion of the starting material, as judged from crude $^{19}F$ NMR in $CD_3OD$, is achieved only after homogenous solution is obtained by heating the reaction mixture. Because p-methoxyacetophenone is deactivated towards nucleophilic attack by the p-methoxy substituent, it is not very prone to base-promoted self-condensation. However, self-condensation proceeds to a significant extent when other ketones are used, including hindered pinacolone (tert-butyl methyl ketone). The phase separation of metal diketonates can be prevented by using lithium or sodium alkoxide or hydride bases.

Quantitative $^{19}F$ NMR

NMR spectra were acquired using calibrated 900 pulses, 32,000 complex points, spectral window −20 to −120 ppm, relaxation delay 2.5 s, and 128 averages. Spectra were processed in MNova with exponential line broadening (5 Hz), manual phase correction, and Whittaker smoother baseline correction (filter=1 ppm). Integral regions were 7 ppm for PFPE (−91 ppm) and 2 ppm for the reference and terminal groups ($CF_2$ in FDK and PFPE-DEA, $CF_3$ in PFOB). Incomplete relaxation of the reference, as $R_1^{TFA}$=0.32$s^{-1}$ at 11.7 T, was accounted for using a correction factor of $[(1-e(-TR \times R_1^{TFA})/(1-e(-TR \times R_1^{PFPE})]$.[15] With very low amounts of paramagnetic analytes, up to 20,000 scans with a relaxation delay of 0 (2,000 complex points, TR=78 ms, 26 min total time) were acquired, and the relaxation correction was determined empirically using a more concentrated sample with matching $R_1$. Occasionally, heterogeneous samples such as cell lysates with high FETRIS loadings presented very broad signals with severely distorted baseline. Quantitative analysis of these samples was performed after treatment with 25 µL of 10 M NaOH, which decomposed the ligand but not the backbone of PFPE, yielding colorless solutions that stayed homogenous for several hours.

REFERENCES

1. Solomon, I. Relaxation processes in a system of two spins. *Phys Rev* 99, 559-565 (1955).
2. Bloembergen, N. & Morgan, L. O. Proton relaxation times in paramagnetic solutions. Effects of electron spin relaxation. *J Chem Phys* 34, 842-850 (1961).
3. Gillis, P., Roch, A. & Brooks, R. A. Corrected equations for susceptibility-induced $T_2$-shortening. *J Magn Reson* 137, 402-407 (1999).
4. Gueron, M. Nuclear relaxation in macromolecules by paramagnetic ions: A novel mechanism. *J Magn Reson (1969)* 19, 58-66 (1975).
5. Freire, M. G., Ferreira, A. G. M., Fonseca, I. M. A., Marrucho, I. M. & Coutinho, J. A. P. Viscosities of liquid fluorocompounds. *J Chem EngData* 53, 538-542 (2008).
6. Kadayakkara, D. K., Damodaran, K., Hitchens, T. K., Bulte, J. W. M. & Ahrens, E. T. F-19 spin-lattice relaxation of perfluoropolyethers: Dependence on temperature and magnetic field strength (7.0-14.1 T). *J Magn Reson* 242, 18-22 (2014).
7. Rubinstein, M., Baram, A. & Luz, Z. Electronic and nuclear relaxation in solutions of transition metal ions with spin S=3/2 and 5/2. *Molecul Phys* 20, 67-80 (1971).
8. Aime, S. et al. Relaxometric evaluation of novel manganese(II) complexes for application as contrast agents in magnetic resonance imaging. *J Bio Inorg Chem* 7, 58-67 (2002).
9. Powell, D. H. et al. Magnetic-field-dependent electronic relaxation of Gd3+ in aqueous solutions of the complexes [Gd(H2O)8]3+, [Gd(propane-1,3-diamine-N,N,N',N'-tetraacetate)(H2O)2]-, and [Gd(N,N'-bis[(N-methylcarbamoyl)methyl]-3-azapentane-1,5-diamine-3,N,N'-triacetate)(H2O)] of interest in magnetic-resonance imaging. *Helv Chim Acta* 76, 2129-2146 (1993).
10. Vigouroux, C., Bardet, M., Belorizky, E., Fries, P. H. & Guillermo, A. Nuclear and electronic relaxation in lanthanide solutions: (CH3)4N+/Gd3+ repulsive ion pair in D2O. *Chem Phys Lett* 286, 93-100 (1998).
11. Bertini, I., Galas, O., Luchinat, C., Messori, L. & Parigi, G. A theoretical analysis of the 1H nuclear magnetic relaxation dispersion profiles of diferric transferrin. *J Phys Chem* 99, 14217-14222 (1995).
12. Sur, S. K. & Bryant, R. G. Nuclear- and electron-spin relaxation rates in symmetrical iron, manganese, and gadolinium ions. *J Phys Chem* 99, 6301-6308 (1995).
13. Haase, A., Fralu, J. & Matthaei, D. FLASH imaging: Rapid NMR imaging using low flip-angle pulses. *J. Magn Reson.* 67, 258 (1986).
14. Gerhardt, G. E. & Lagow, R. J. Synthesis of the perfluoropoly(ethylene glycol) ethers by direct fluorination. *J Org Chem* 43, 4505-4509 (1978).
15. Bharti, S. et al. Improved quantification from $^1$H-NMR spectra using reduced repetition times. *Metabolomics* 4, 367-376 (2008).

Example 3: Compositions and Methods for Imaging Cell Populations

The invention enables clinical non-invasive imaging methods, particularly magnetic resonance imaging (MRI), to visualize the locations and numbers of specific cell populations in the body. The invention describes several novel compositions of perfluorinated compounds that can bind and tightly retain metal ions, for the purpose of producing sensitive cellular labels for tracking cells by fluorine-19 ($^{19}$F) MRI (FIGS. 21-28). Exemplary applications include the diagnostic detection of immune cells that accumulate at tissue sites as part of an inflammatory response and cells that are grafted into the body in order to treat a disease or condition, i.e., cytotherapy. Cells can be endogenous cells in the body, for example, various immune cells (T cells, B cells, macrophages, NK cells, DCs, etc.), various stem cells, progenitor cells, cancer cells, as well as engineered cells, which are often used in cytotherapy in its various forms. Non-invasive imaging of immune cells in the body is useful because it can aid in the diagnosis and monitoring of inflammation. In the field of cytotherapy, the ability to image the cell graft provides valuable feedback about the persistence of the graft, potential cell migration, and improves safety surveillance. Many experimental cell therapies that are in clinical trials, e.g., stem cells and immunotherapeutic cells, could benefit from the use of this technology.

Other embodiments of the present invention are metalated perfluorinated probes that can be detected by positron emission tomography (PET), single-photon emission coherent tomography (SPECT), ultrasonograpy, or computed tomography (CT), all of which are commonly used medical imaging modalities. The invention enables new uses for these imaging modalities by providing a means to detect inflammatory cells and track cytotherapy non-invasively. Also, so called 'dual-mode' agents are envisioned, which can be detected by more than one imaging modality (e.g., MRI-PET), thereby maximizing the utility of new generations of clinical imaging apparatus that integrate two (or more) detection modalities.

The invention describes multiple nanoemulsion formulations of metalated perfluorinated compounds (i.e., 'imaging probes") to render the molecules compatible for in vivo applications. The formulations can be used to determine the biodistribution (e.g., the accumulation and/or location of the labelled cells in a subject after administration) and the level or amount of cellular uptake of the nanoemulsion by the cells.

Additionally, ex vivo or in vivo "targeted" imaging and theranostic agents are described using the molecular platform that provide imaging of cells, tissues, and/or lesions having selected and prevalent molecular epitopes. For example targeting moieties can include antibodies (or fragments), peptides, arginine-rich domains, cationic lipids, aptamers, etc. The targeted agents can specifically bind to a particular cell type, tissue, organ, lesion, and the like.

Moreover, formulations of metalated fluorocarbons are envisioned that have a distinct signatures in MRI that can be used to image multiple cell types, the same cell type at different time points, or multiple molecular epitopes (e.g., multiple cell surface epitopes) within a subject.

Other variants of the inventive composition include "theranostic" agents which can serve both as a therapeutic agent (or drug delivery vehicle) and an imaging probe. Such theranostic agents can help visualize the accurate delivery and dose of the therapy within the body.

The invention also describes novel in vitro methods to assay the degree of cell labeling with the imaging probe, for example, as represented by the average total intracellular probe mass following labeling.

Overall, this invention describes imaging probes that dramatically improve the speed of data acquisition and sensitivity of $^{19}$F-based MRI cell tracking and related applications. $^{19}$F MRI using perfluorocarbons has previously been demonstrated by others, including for clinical cell tracking applications, but adoption has been limited in part because of the low sensitivity of the $^{19}$F-based imaging probes. The described compositions help to overcome this sensitivity limitation. This disclosure describes the first formulation of metal chelates that are soluble in the fluorous phase of the fluorocarbon-in-water emulsions used for fluorine-19 MRI. The metal ions tethered by the dissolved chelates dramatically improves the sensitivity (at least 5×) and reduction in imaging time (up to 70×) by reducing the $^{19}$F spin-lattice relaxation time ($T_1$) of the tracer agent. References have focused on optimizing the structure of fluorocarbon molecules or by placing paramagnetic metal chelates on the surface of fluorous nanoemulsion droplets. These prior formulations are incompatible with cell tracking applications because the metal-fluorocarbon complex is unstable inside the intracellular milieu, are difficult to deliver intracellularly in non-phagocytic cells, are not retained by the cells long-term, and/or are cytotoxic.

Moreover, in some embodiments, iron ions are used and highly efficacious in terms of $^{19}$F $T_1$ enhancement. This was a serendipitous and unexpected finding, as Fe is one of the most common metal ions in the body, and is well tolerated in case there is any leakage from the nanoemulsion, which is expected to be de minimis and supported by our data. Clinical $^1$H contrast agents rely on $Gd^{3+}$, but this has been recently shown to have renal toxicities in certain patients and tends to accumulate in the brain long-term; these safety concerns, in practical terms, make it challenging to get new Gd-based agents into the clinic from a regulatory standpoint.

Additionally, multiple formulations of metalated fluorocarbons are envisioned that have discrete $^{19}$F $T_1$ values; $T_1$ can be easily 'tuned', for example, by stoichiometric blending of metalated fluorocarbons with non-metal bearing fluorocarbons. The discrete $T_1$ values within labelled cell populations can be used to simultaneously image multiple cell types or temporal patterning of the same cell types within a single subject. In some embodiments, this approach could be used with targeted agents where different epitopes are targeted with imaging probes having different T1's, thereby enabling multiplexed imaging of the pattern of multiple molecular targets within the same subject in vivo.

Metalated fluorocarbons of this invention can be used for radiographic imaging (e.g, PET, SPECT) by introducing radioactive isotopes into the fluorous phase, e.g., $^{89}$Zr or $^{64}$Cu for PET, or $^{111}$In or $^{99}$Tc for SPECT Such nanoemulsion formulations will ready load these isotopes immediately prior to use by simple co-mixing (FIGS. 24-27). The emulsion is "self-delivering", to viable cells only, either ex vivo or in vivo; once a cell is labelled it is tightly held within the cell with no leakage thereby eliminating false positive signals, and the fluorocarbon carrier is non-toxic.

The chemical synthesis and purification scheme for the novel metalated fluorocarbons has been worked out. These methods are scalable to batch sizes appropriate for clinical trial testing. As described in Example 1, ex vivo cell labeling, followed by in vivo cell imaging using $^{19}$F MRI, has been demonstrated in rodents (FIG. 28). The formulation of the metalated fluorocarbons can be modified into IV-injectable inflammation MRI agents, as well as PET inflammation agents that incorporate $^{89}$Zr.

Example 4: Compositions and Methods for Imaging Cell Populations

Synthesis of Fluorinated β-diketones (FDK): Optimization and Purification

The overall procedure for the synthesis of fluorinated D-diketones (FDK) is given in the scheme below.

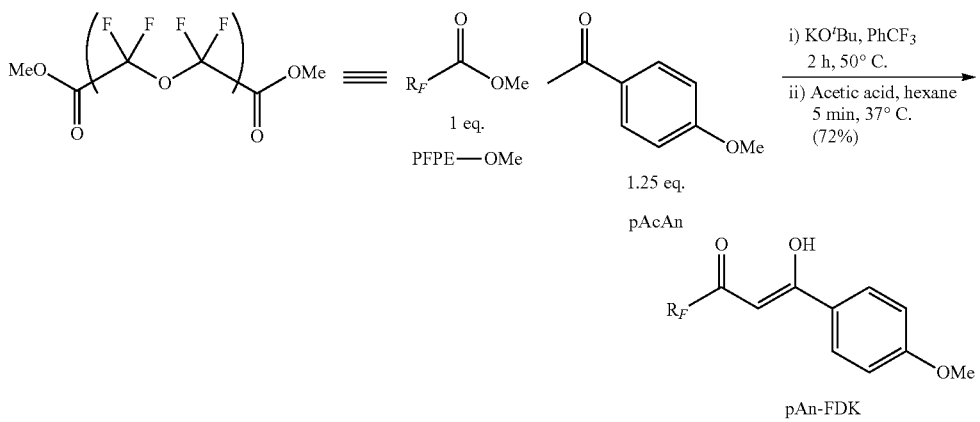

Methods to improve the product purity and increase the reaction yield are described herein.

Purification Methods

For purification, methods for the complete removal of side products and unreacted starting materials are described. The unwanted species may be classified as fluorous, organic, or inorganic:

|  | Starting materials | Side products |
|---|---|---|
| Fluorous | PFPE methyl ester (limiting; consumed) | / |
| Organic | p-Acetanisole (in excess) | / |
| Inorganic | Potassium tert-butoxide (in excess) | Potassium methoxide, potassium acetate |

A rudimentary purification procedure involves a filtration step to remove the bulk of the inorganics, followed by a washing step with methanol to remove remaining inorganics as well as organic species. ($^{19}$F NMR can be used to confirm that all PFPE methyl ester is consumed, so there is essentially de minimis fluorous species to remove.) This purification method is simple, however, residual p-acetanisole (pAcAn) starting material may be observed, evidenced by a residual peak on the $^1$H NMR spectrum at 2.56 ppm (e.g., <1% pAcAn remaining). Purification methods for the more complete removal of pAcAn have been investigated.

Silica Chromatography

Silica chromatography was unsuccessful as a purification method. The solvent system hexane/ethyl acetate (75:25) was used, in which the components of pAn-FDK have desirable RF values of 0.34-0.75. The less polar components of pAn-FDK contained a mixture of mono and bifunctional diketone species, along with p-acetanisole (RF=0.70). The most polar component (RF=0.34) was isolated and was determined by $^{19}$F NMR to be solely bifunctional pAn-FDK. Promisingly, the $^1$H NMR spectrum showed no p-AcAn. However, bifunctional FDK was a solid and no longer soluble in PFPE, which is a required property.

Neutral Aluminum Oxide Chromatography

Due to the higher polarity of aluminium oxide in comparison to silica, pAn-FDK moves slowly through this stationary phase for this method of purification and thus may not be a desired method for larger production batches.

Fluorous Silica (Fluorous Solid Phase Extraction, F-SPE)$^2$

The use of fluorous silica is an alternative and efficient means for separating the components of the crude product based on fluorine content, rather than polarity. For example, fluorous silica were purchased pre-packed into cartridges (e.g., FluoroFlash Solid Phase Extraction cartridges, 10 g, 60 cc), and the following method parameters were employed:

Activation: DMF (5 mL)

Equilibration: MeOH/H2O (8:2, 50 mL)

Loading: crude pAn-FDK (0.5 mL, approx. 0.8 g) in ethanol (1 mL)

Fluorophobic wash: MeOH/H2O (8:2, 300 mL); elutes all organic species, i.e. pAcAn Fluorophilic wash: acetone (300 m); elutes all fluorous species, i.e. pAn-FDK Cleaning: acetone (300 mL)

Figure 29:
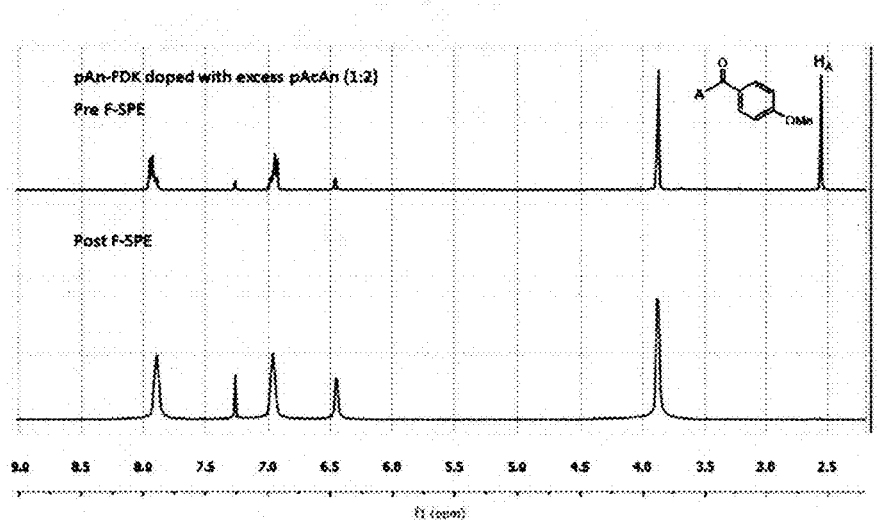
FIG. 29. $^1$H NMR spectra of pAn-FDK doped with p-acetanisole (pAcAn) before (top) and after (bottom) purification by fluorous SPE.

The results showed that fluorous SPE allowed for the efficient removal of pAcAn from pAn-FDK samples. To test the limits of the technique, a pAn-FDK sample was doped with an excess of pAcAn (2:1) and subjected to fluorous SPE. The sample was successfully purified (FIG. 29). Thus, successful purification of pAn-FDK by removal of pAcAn to below the detection limits of the NMR and GC-MS (see Characterization section below) was achieved. FIG. 29 shows $^1$H NMR spectra of pAn-FDK doped with pAcAn before (top) and after (bottom) purification by fluorous SPE.

Yield

It is desirable to minimize product loss during initial synthesis of pAn-FDK. Preliminary procedures (described in Kislukhin et al., Nat Mater, 2016, 15(6): 662-668) gave an overall yield of often <70%. $^1$H NMR shows that the reaction goes to completion so the mass loss is not due to reaction inefficiency. The >30% loss is primarily due to the partial solubility of pAn-FDK in methanol during the washing step. pAn-FDK oil is viscous and only partially soluble in the pre-filtration PhCF3/hexane/acetic acid (10:40:1) solvent mixture, so there is often loss during transfer between glassware prior to filtration.

In order to optimize the pre-chromatography yield of pAn-FDK, the following steps were taken (i) ethanol, rather than hexane, was added after the reaction was quenched with acetic acid. FDK has limited solubility in hexane but high solubility in ethanol, minimizing loss during transfer, and (ii) the methanol washing step was omitted, and inorganics were removed by Buchner filtration, washing with water and brine, and celite filtration. Subsequently, the pre-chromatography yield of pAn-FDK was measured to be 83%.

Alternatively, the reaction was performed in methyl-tert-butyl ether (MTBE) rather than trifluorotoluene. The reagents and product are highly soluble in both solvents, but MTBE offers the advantage of a much lower boiling point for easier vacuum removal (55° C. versus 102° C., respectively). Sodium tert-butoxide was used interchangeably with potassium tert-butoxide as the base. Both alkoxide salts allow the reaction to reach completion within 2 hours, and have similar safety profiles.

These purification experiments, and the methods used, provide some purification approaches, and show that increasing yield is certainly feasible using methods known in the art. Other purification methods can be used to increase yield of the desired product.

Characterization and Analytical Methods Development

The following characterization data were gathered on purified pAn-FDK.

Figure 30:
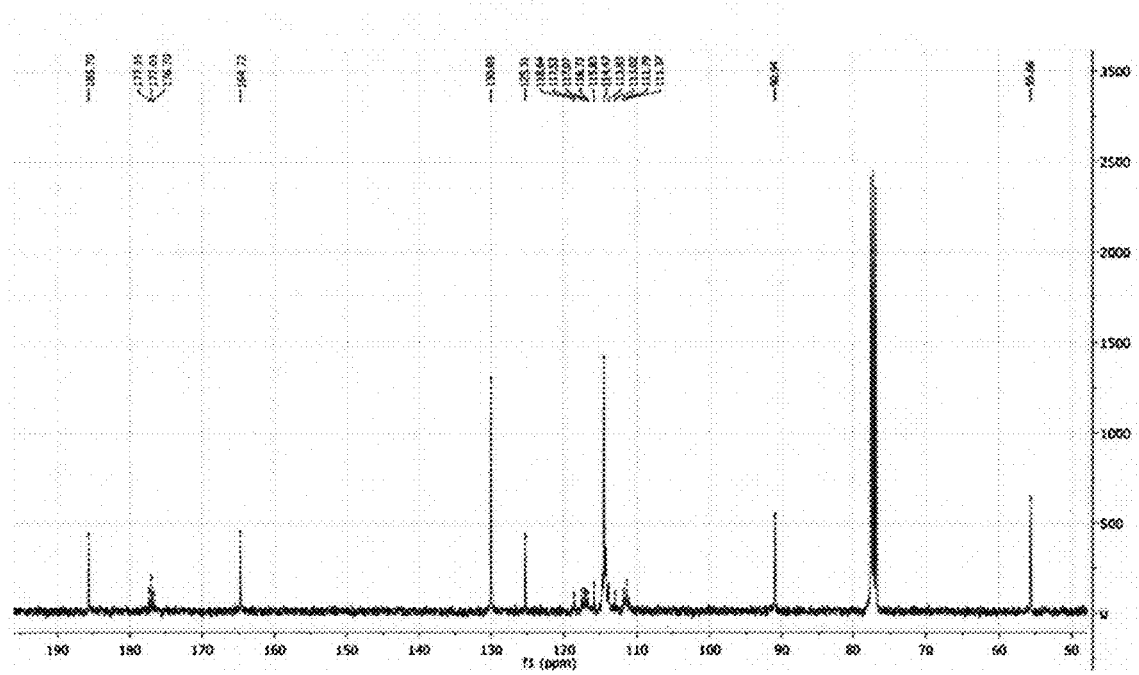
FIG. 30. $^{13}$C NMR spectrum of pAn-FDK.

NMR Spectroscopy. Data (FIG. 30) were acquired using a Bruker Ascend 400 MHz NMR spectrometer.

Figure 31:
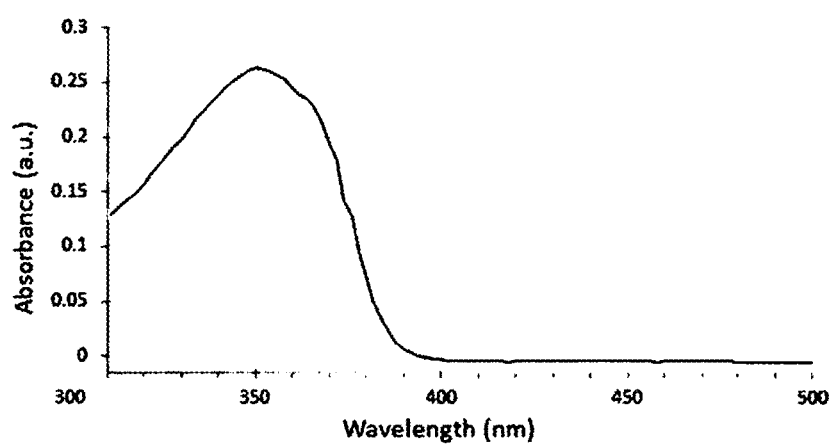
FIG. 31. UV-vis spectrum of non-emulsified pAn-FDK in MeOH (40 μM), where λmax=350 nm.

UV-vis Spectroscopy. Data (FIG. 31) were acquired using a Tecan Infinite M200 PRO instrument.

Figure 32:
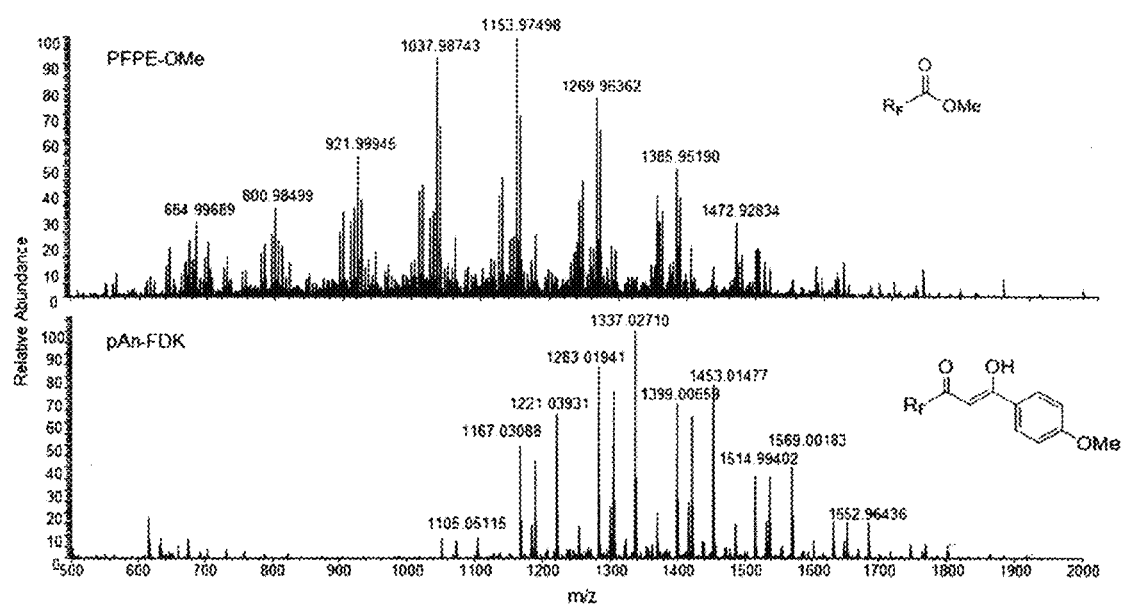
FIG. 32. Ultra high resolution mass spectra of PFPE-OMe (top) and pAn-FDK (bottom).

Mass Spectrometry. Data (FIG. 32) were acquired using a Thermo Scientific Orbitrap Elite, HESI-LIT, set a resolution=240,000, mass range m/z=100-2000, injection temp=50° C., direct infusion, and concentration=10 ppm in MeOH.

Gas chromatography-mass spectrometry (GC-MS). GC-MS data (FIGS. 32-36) were acquired using a Thermo Scientific Trace 1310 GC instrument coupled to TSQ 8999 Evo MS (EI) Column with parameters set at: TG-wax ms, 30 m×20 mm×0.25 μm, gas flow rate 20.0 mL/min, injection temperature 250° C., split injection type, and concentration 10 ppm in DCM.

Figure 33:
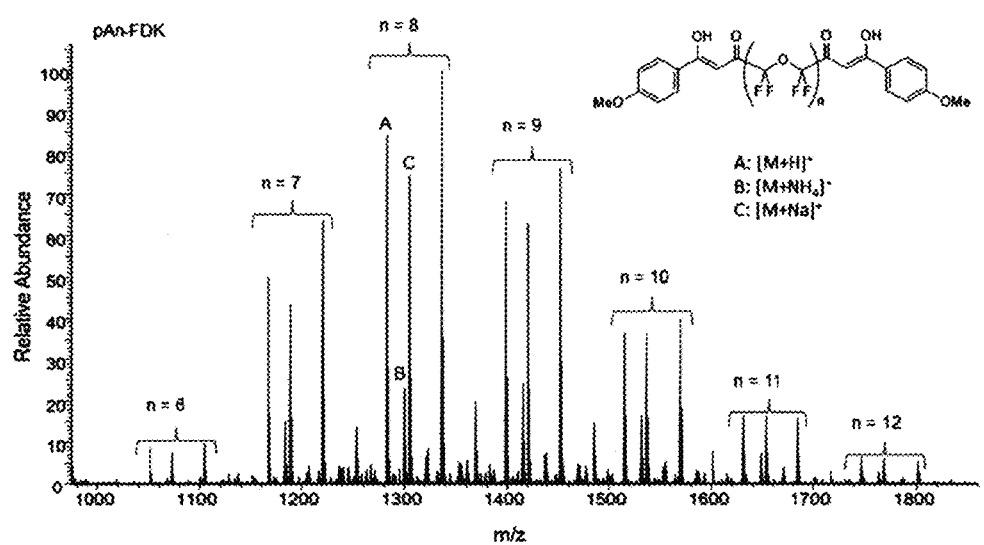
FIG. 33. Mass spectrum of pAn-FDK.

FIG. 33 shows mass spectrum of pAn-FDK The size distribution of the pAn-FDK product is readily visualized. High resolution MS data show that the PFPE-OMe starting material was completely consumed during the reaction, within the detection limit of the MS.

Figure 34:
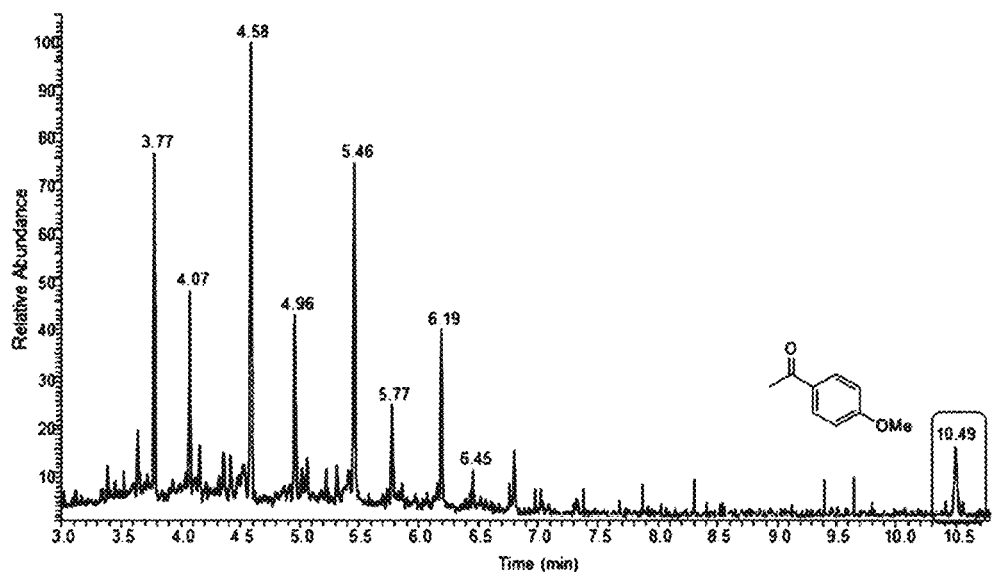
FIG. 34. Total Ion Chromatogram (TIC) for pAn-FDK sample after MeOH washing, but prior to fluorous SPE purification.

FIG. 34 shows Total Ion Chromatogram (TIC) for pAn-FDK sample after MeOH washing, but prior to fluorous SPE purification.

Figure 35:
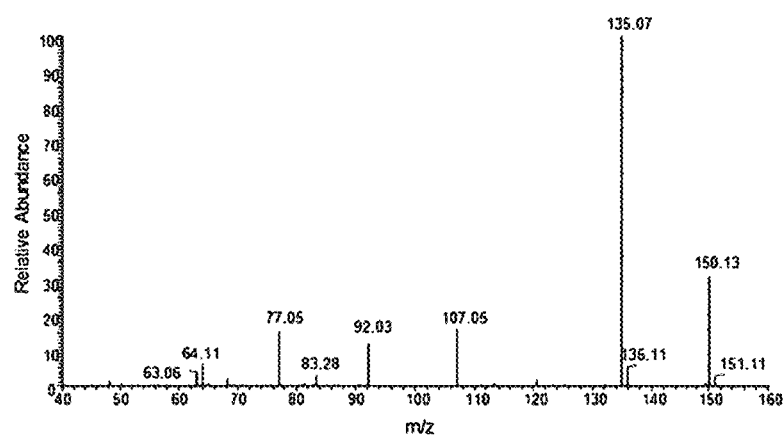
FIG. 35. Displays TIC fragmentation pattern of peak at T=10.49 min.

FIG. 35 provides Displays TIC fragmentation pattern of peak at T=10.49 min.

Figure 36:
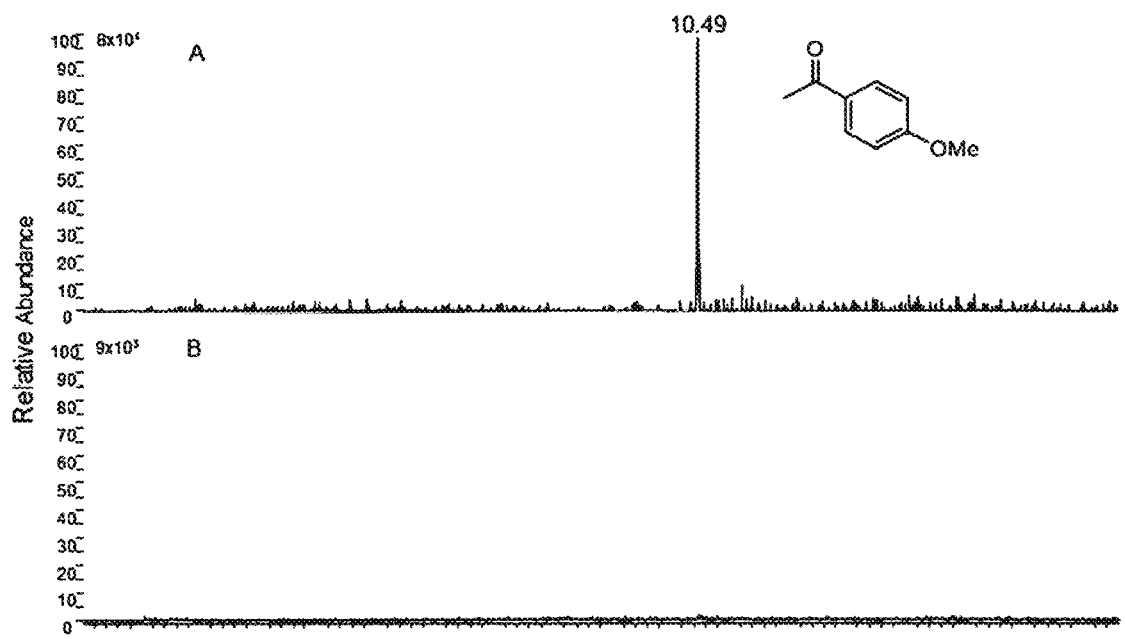
FIGS. 36A and 36B. Displays Extracted Ion Chromatogram (EIC) for m/z=150 (M+• of pAcAn).

FIG. 36 shows Displays Extracted Ion Chromatogram (EIC) for m/z=150 (M+• of pAcAn). FIG. 36A shows pAn-FDK sample after MeOH washing, but prior to fluorous SPE purification. FIG. 36B displays the same sample after fluorous SPE. Overall, GC-MS data shows that fluorous SPE is an effective method for purifying pAn-FDK by removing pAcAn.

REFERENCES

Kislukhin, A. A. et al. Paramagnetic fluorinated nanoemulsions for sensitive cellular fluorine-19 magnetic resonance imaging. Nat. Mater. (2016).

Zhang, W. & Curran, D. P. Synthetic applications of fluorous solid-phase extraction (F-SPE). Tetrahedron 62, 11837-11865, doi:10.1016/j.tet.2006.08.051 (2006).

The examples set forth above are provided to give those of ordinary skill in the art a complete disclosure and description of how to make and use the embodiments of the compositions, systems and methods of the invention, and are not intended to limit the scope of what the inventors regard as their invention. Modifications of the above-described modes for carrying out the invention that are obvious to persons of skill in the art are intended to be within the scope of the following claims. All patents and publications mentioned in the specification are indicative of the levels of skill of those skilled in the art to which the invention pertains. All references cited in this disclosure are incorporated by reference to the same extent as if each reference had been incorporated by reference in its entirety individually.

All headings and section designations are used for clarity and reference purposes only and are not to be considered limiting in any way. For example, those of skill in the art will appreciate the usefulness of combining various aspects from different headings and sections as appropriate according to the spirit and scope of the invention described herein.

All references cited herein are hereby incorporated by reference herein in their entireties and for all purposes to the same extent as if each individual publication or patent or patent application was specifically and individually indicated to be incorporated by reference in its entirety for all purposes.

Many modifications and variations of this application can be made without departing from its spirit and scope, as will be apparent to those skilled in the art. The specific embodiments and examples described herein are offered by way of example only, and the application is to be limited only by the terms of the appended claims, along with the full scope of equivalents to which the claims are entitled.

What is claimed is:

1. A non-invasive imaging method comprising:
   a) administering to a subject a cellular labelling composition comprising a perfluorinated compound comprising fluorine-19($^{19}$F), wherein said compound comprising fluorine-19($^{19}$F) associates with one or more cells; and
   b) detecting said association using an imaging modality, wherein said association can include cellular binding or cellular uptake, wherein said perfluorinated compound is formula (i):

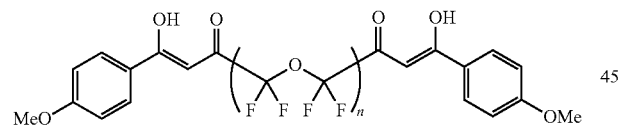

(i)

wherein n is 4 to 20, or 4 to 16.

2. The method of claim 1, wherein said imaging modality is selected from the group consisting of magnetic resonance imaging (MRI), positron emission tomography (PET), single-photon emission coherent tomography (SPECT), ultrasonography (US), and computed tomography (CT).

3. The method of claim 1, wherein said perfluorinated compound binds and tightly retains metal ions in the fluorous phase.

4. The method of claim 3, wherein said metal ions are selected from the group consisting of $VO^{2+}$, $Cr^{3+}$, $Mn^{2+}$, $Mn^{3+}$, $Fe^{3+}$, $Ni^{2+}$, $Cu^{2+}$, $Ce^{3+}$, $Pr^{3+}$, $Nd_{3+}$, $Sm^{3+}$, $Eu^{3+}$, $Gd^{3+}$, $Tb^{3+}$, $Dy^{3+}$, $Ho^{3+}$, $Er^{3+}$, $Tm^{3+}$, $Yb^{3+}$, $^{44}Sc^{3+}$, $^{52}Mn^{2+}$, $^{61}Cu^{2+}$, $^{64}Cu^{2+}$, $^{66}Ga^{3+}$, $^{68}Ga^{3+}$, $^{86}Y^{3+}$, $^{89}Zr^{4+}$, $^{67}Ga^{3+}$, $^{99m}Tc^{4+}$, $^{111}In^{3+}$ and $^{177}L^{3+}$.

5. The method of claim 1, wherein said perfluorinated compound is formulated as a nanoemulsion.

6. The method of claim 5, wherein said nanoemulsion further comprises a perfluorocarbon.

7. The method of claim 6, wherein said perfluorocarbon is a compound of any one of formulas (ii)-(vi):

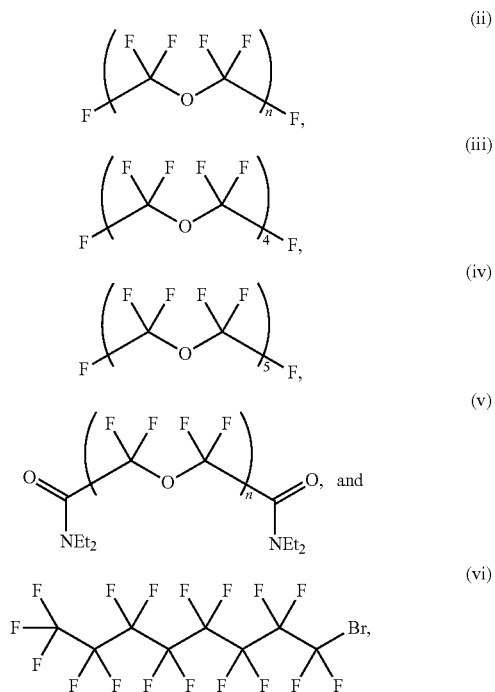

wherein n is 4 to 20, or 4 to 16.

8. The method of claim 1, wherein said composition comprises a perfluorocarbon of any one of formulas (ii)-(vi):

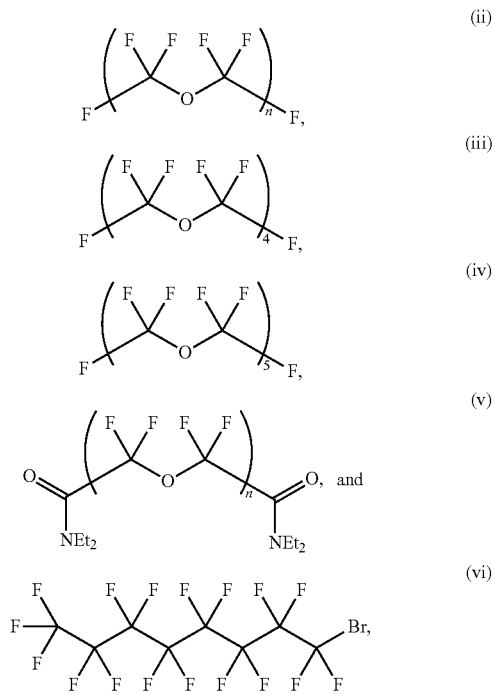

wherein n is 4 to 20, or 4 to 16.

9. The method of claim 1, wherein said composition allows tracking cells by Mill, wherein said method comprises detecting the cells associated with at least one component of the composition comprising fluorine-19 ($^{19}$F).

10. An in vivo imaging method, comprising
   a) ex vivo labeling cells with a cellular labeling composition comprising a perfluorinated compound comprising fluorine-19 ($^{19}$F) under such conditions that said compound comprising fluorine-19 ($^{19}$F) is internalized by the cells;
   b) administering the labeled cells to a subject;
   c) detecting said labeled cells in said subject using an imaging modality, and
   d) assaying for the degree of cell accumulation in one or more tissues in said subject, wherein said perfluorinated compound is formula (i):

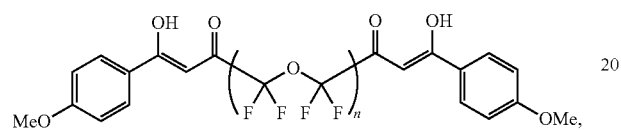

(i)

wherein n is 4 to 20, or 4 to 16.

11. The method of claim 10, wherein said perfluorinated compound is formulated as a nanoemulsion.

* * * * *